(12) United States Patent
Bierlmaier et al.

(10) Patent No.: US 10,150,772 B2
(45) Date of Patent: Dec. 11, 2018

(54) CRYSTALLINE FORMS OF PARP INHIBITORS

(71) Applicant: CEPHALON, INC., Frazer, PA (US)

(72) Inventors: Stephen J. Bierlmaier, Thorndale, PA (US); Ralph C. Haltiwanger, West Chester, PA (US); Martin J. Jacobs, Versailles, KY (US)

(73) Assignee: CEPHALON, INC., Frazer, PA (US)

( * ) Notice: Subject to any disclaimer, the term of this patent is extended or adjusted under 35 U.S.C. 154(b) by 0 days.

(21) Appl. No.: 15/529,883

(22) PCT Filed: Nov. 25, 2015

(86) PCT No.: PCT/US2015/062572
§ 371 (c)(1),
(2) Date: May 25, 2017

(87) PCT Pub. No.: WO2016/086080
PCT Pub. Date: Jun. 2, 2016

(65) Prior Publication Data
US 2017/0267683 A1    Sep. 21, 2017

Related U.S. Application Data

(60) Provisional application No. 62/084,652, filed on Nov. 26, 2014.

(51) Int. Cl.
| | | |
|---|---|---|
| *C07D 487/04* | (2006.01) | |
| *C07C 59/06* | (2006.01) | |
| *C07C 53/10* | (2006.01) | |
| *C07C 59/245* | (2006.01) | |
| *C07D 207/28* | (2006.01) | |
| *C07C 57/15* | (2006.01) | |

(52) U.S. Cl.
CPC ............ *C07D 487/04* (2013.01); *C07C 53/10* (2013.01); *C07C 57/15* (2013.01); *C07C 59/06* (2013.01); *C07C 59/245* (2013.01); *C07D 207/28* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 7,122,679 B2 | 10/2006 | Ator et al. | |
| 8,633,314 B2 * | 1/2014 | Bierlmaier | ........... C07D 487/04 544/372 |
| 8,716,493 B2 | 5/2014 | Chatterjee et al. | |

FOREIGN PATENT DOCUMENTS

| | | | |
|---|---|---|---|
| WO | WO 2008/063644 A1 | | 5/2008 |
| WO | WO 2008/063644 | * | 5/2017 |

OTHER PUBLICATIONS

Morissette et al. in Drug Delivery Reviews, 56 (2004) 275-300 (Year: 2004).*
Fong et al. in Journal of Clinical Oncology, 28(15), 2512-2519 (2010) (Year: 2010).*
Tutt et al. in Journal of Clinical Oncology, 27(18) (2009) (Abstract) (Year: 2009).*
International Preliminary Report on Patentability issued in related International Patent Application No. PCT/US2015/062572, dated Jun. 8, 2017.
Griffin et al., "The role of inhibitors of poly(ADP-ribose) polymerase as resistance-modifying agents in cancer therapy," vol. 77, No. 6, pp. 408-422 (1995). [Abstract].
P.H. Stahl et al., "Electronic Supplementary Material for CrytEngComm," CrytEngComm, Jan. 1, 2005, 8 pages.
International Search Report and Written Opinion issued in related International Patent Application No. PCT/US2015/062572, dated Apr. 26, 2016.

* cited by examiner

*Primary Examiner* — Dennis Heyer
(74) *Attorney, Agent, or Firm* — Gilberto M. Villacorta; Foley & Lardner LLP

(57) ABSTRACT

The present disclosure relates to crystalline forms of 4,5,6,7-tetrahydro-11-methoxy-2-[(4-methyl-1-piperazinyl)methyl]-1H-cyclopenta[a]pyrrolo[3,4-c]carbazole-1,3(2H)-dione, including salts forms and free base forms.

18 Claims, 38 Drawing Sheets

XRPD PATTERN FOR A COMPOUND A FREE BASE, FORM A₀

DSC/TGA OVERLAY FOR COMPOUND A FREE BASE, FORM A0

XRPD PATTERN OF COMPOUND A ACETATE SALT, FORM A$_{1.5}$

DVS OVERLAY OF COMPOUND A ACETATE SALT, FORM A$_{1.5}$

PHOTOMICROGRAPH OF COMPOUND A ACETATE SALT, FORM $A_{1.5}$

XRPD PATTERN OF COMPOUND A GLYCOLATE SALT HYDRATE, FORM A$_1$

DSC AND TGA OVERLAY FOR A COMPOUND A GLYCOLATE HYDRATE SALT, FORM A₁

PHOTOMICROGRAPH OF COMPOUND A GLYCOLATE HYDRATE SALT, FORM A$_1$

XRPD PATTERN OF COMPOUND A L-MALATE SALT, FORM A₁

VT-XRPD PATTERNS OF COMPOUND A MALATE SALT, FORM A1

DSC AND TGA OVERLAY OF COMPOUND A L-MALATE SALT, FORM A1

PHOTOMICROGRAPH OF COMPOUND A L-MALATE SALT, FORM $A_1$

XRPD PATTERN OF COMPOUND A MALATE SALT, FORM A$_{1.5}$

DSC AND TGA OVERLAY OF COMPOUND A L-MALATE SALT, FORM A$_{1.5}$

XRPD PATTERN OF COMPOUND A L-PYROGLUTAMATE SALT, FORM A₁

DSC AND TGA OVERLAY OF COMPOUND A L-PYROGLUTAMATE SALT, FORM A1

PHOTOMICROGRAPH OF COMPOUND A L-PYROGLUTAMATE SALT, FORM $A_1$

DSC AND TGA OVERLAY OF COMPOUND A FREE BASE, FORM $C_0$

PHOTOMICROGRAPH OF COMPOUND A FREE BASE, FORM $C_0$

XRPD PATTERN OF COMPOUND A HYDROCHLORIDE SALT, FORM A

DSC AND TGA OVERLAY OF COMPOUND A HYDROCHLORIDE SALT, FORM A

XRPD PATTERN OF COMPOUND A FUMARATE SALT, FORM A

DSC AND TGA OVERLAY OF COMPOUND A FUMARATE SALT, FORM A

DSC AND TGA OVERLAY OF COMPOUND A p-TOLUENESULFONATE SALT, FORM A

PLASMA LEVELS OF COMPOUND B, 1 mg/kg INTRAVENOUS, COMPOUND A, ASCORBIC ACID SALT, 30 mg/kg ORAL, AND COMPOUND A, GLYCOLATE HYDRATE SALT, 30 mg/kg ORAL IN RAT.

SINGLE CRYSTAL STRUCTURE OF COMPOUND A, GLYCOLATE HYDRATE SALT

CRYSTALLINE FORMS OF PARP INHIBITORS

CROSS REFERENCE TO RELATED APPLICATION

This application is the National Phase of International Patent Application No. PCT/US2015/062572, filed on Nov. 25, 2015, which claims priority from U.S. Provisional Patent Application No. 62/084,652, filed on Nov. 26, 2014, all of which are incorporated herein by reference in their entirety.

TECHNICAL FIELD

The present disclosure relates to crystalline forms of 4,5,6,7-tetrahydro-11-methoxy-2-[(4-methyl-1-piperazinyl)methyl]-1H-cyclopenta[a]pyrrolo[3,4-c]carbazole-1,3(2H)-dione and salts thereof.

BACKGROUND

Compound A (4,5,6,7-Tetrahydro-11-methoxy-2-[(4-methyl-1-piperazinyl)methyl]-1H-cyclopenta[a]pyrrolo[3,4-c]carbazole-1,3(2H)-dione) is a PARP (poly ADP-ribose polymerase) inhibitor for use in the treatment of breast, ovarian, and other cancers, either alone or in conjunction with chemotherapy or radiotherapy. See, e.g., U.S. Pat. Nos. 7,122,679; 8,716,493; and 8,633,314.

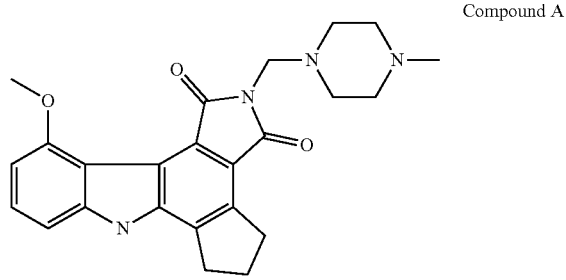 [SMILES: COc1cccc2[nH]c3c4c(c5c(c3c12)C(=O)N(CN1CCN(C)CC1)C5=O)CCC4]

Compound A

Compound A is a prodrug of Compound B:

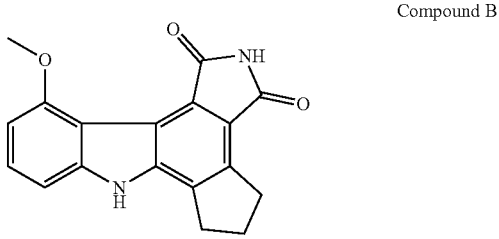 [SMILES: COc1cccc2[nH]c3c4c(c5c(c3c12)C(=O)NC5=O)CCC4]

Compound B

The free base form of Compound A forms hydrates, which are undesirable. In addition, the free base form of Compound A has a low bulk density, impeding manufacturing. Alternative forms of Compound A are needed.

SUMMARY

The disclosure is directed to Compound A, acetate salt Form $A_{1.5}$; Compound A, glycolate salt hydrate Form $A_1$; Compound A, L-malate salt Form $A_1$; Compound A, L-malate salt Form $A_{1.5}$; Compound A, L-pyroglutamate salt Form $A_1$; Compound A, free base Form $C_0$; Compound A, hydrochloride salt Form A; Compound A, fumarate salt Form A; and Compound A, p-toluenesulfonate salt Form A. Pharmaceutical compositions comprising one or more of these forms are also described. Methods of using these forms is described, as well.

DETAILED DESCRIPTION OF ILLUSTRATIVE EMBODIMENTS

The present disclosure addresses a need in the art by providing new forms of Compound A, including new crystalline free base forms of Compound A and new crystalline salt forms of Compound A.

The disclosure is directed to, among other things, Compound A, acetate salt Form $A_{1.5}$; Compound A, glycolate salt hydrate Form $A_1$; Compound A, L-malate salt Form $A_1$; Compound A, L-malate salt Form $A_{1.5}$; Compound A, L-pyroglutamate salt Form $A_1$; Compound A, free base Form $C_0$; Compound A, hydrochloride salt Form A; Compound A, fumarate salt Form A; and Compound A, p-toluenesulfonate salt Form A. Pharmaceutical compositions comprising one or more of these forms are also described.

Figure 3:
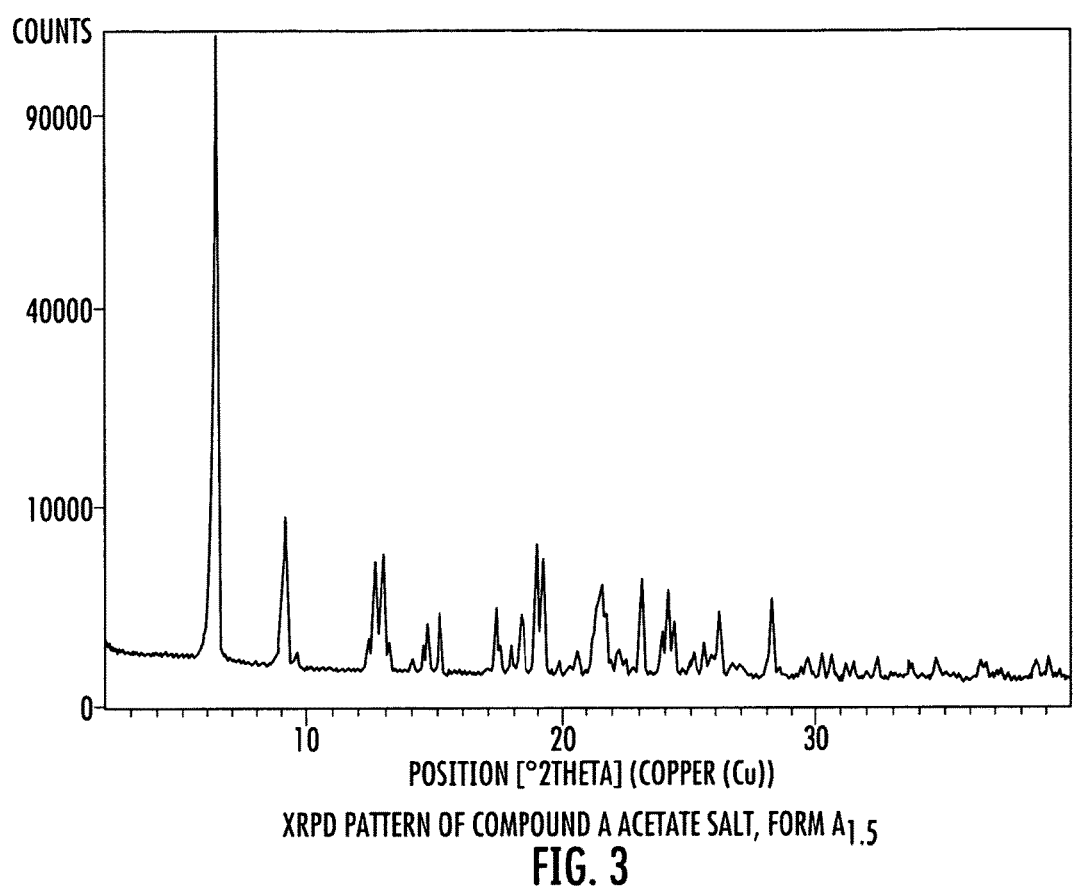
FIG. 3 shows an XRPD Pattern of Compound A Acetate Salt, Form $A_{1.5}$.

In one embodiment, the present disclosure pertains to Compound A, acetate salt Form $A_{1.5}$. In one aspect, this crystalline form is characterized by an X-ray diffraction pattern comprising one or more of the following peaks: 6.4, 9.2, 12.7, 13.0, 15.2, 17.4, 18.4, 19.0, 19.3, 21.3, 21.5, 23.1, 24.1, 24.2, and/or 28.2±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 3.

The disclosure is also directed to Compound A, glycolate hydrate salts. These salts can have varying amounts of water within the crystal structure. For example, the ratio of Compound A to water can be from about 1:0.1 to about 1:1. In other embodiments, the ratio of Compound A to water is 1:0.1; 1:0.2; 1:0.3; 1:0.4; 1:0.5; 1:0.6; 1:0.7; 1:0.8; 1:0.9 or 1:1.

Figure 9:
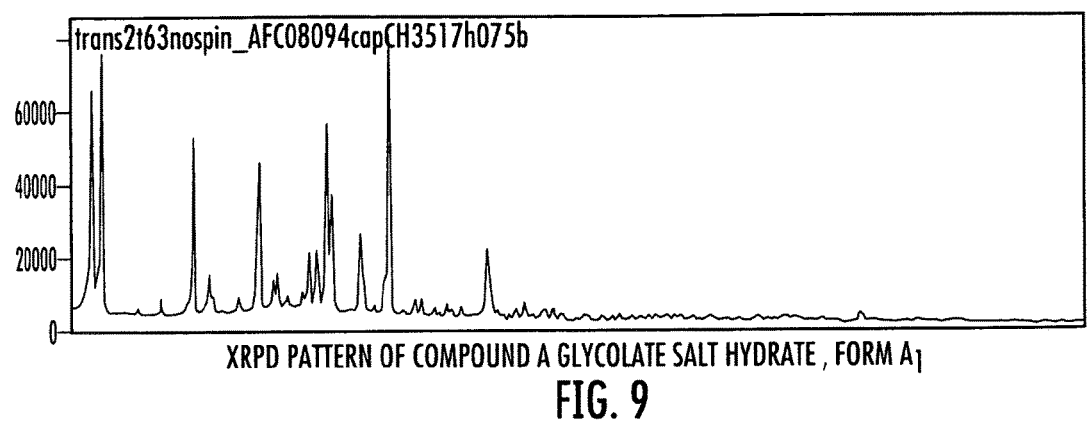
FIG. 9 shows an XRPD Pattern of Compound A Glycolate Salt Hydrate, Form $A_1$.

Another embodiment of the present disclosure pertains to Compound A, glycolate hydrate salt Form $A_1$. In one aspect, this crystalline form is characterized by an X-ray diffraction pattern comprising one or more of the following peaks: 8.1, 8.2, 8.7, 13.9, 14.7, 14.9, 16.3, 17.4, 17.6, 18.2, 18.5, 19.0, 20.2, 20.6, 21.2, 21.4, 23.0, 24.5, 24.7, 26.1, 26.3, 28.0, 30.0, 30.1, 30.2, and/or 32.8±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 9.

Figure 14:
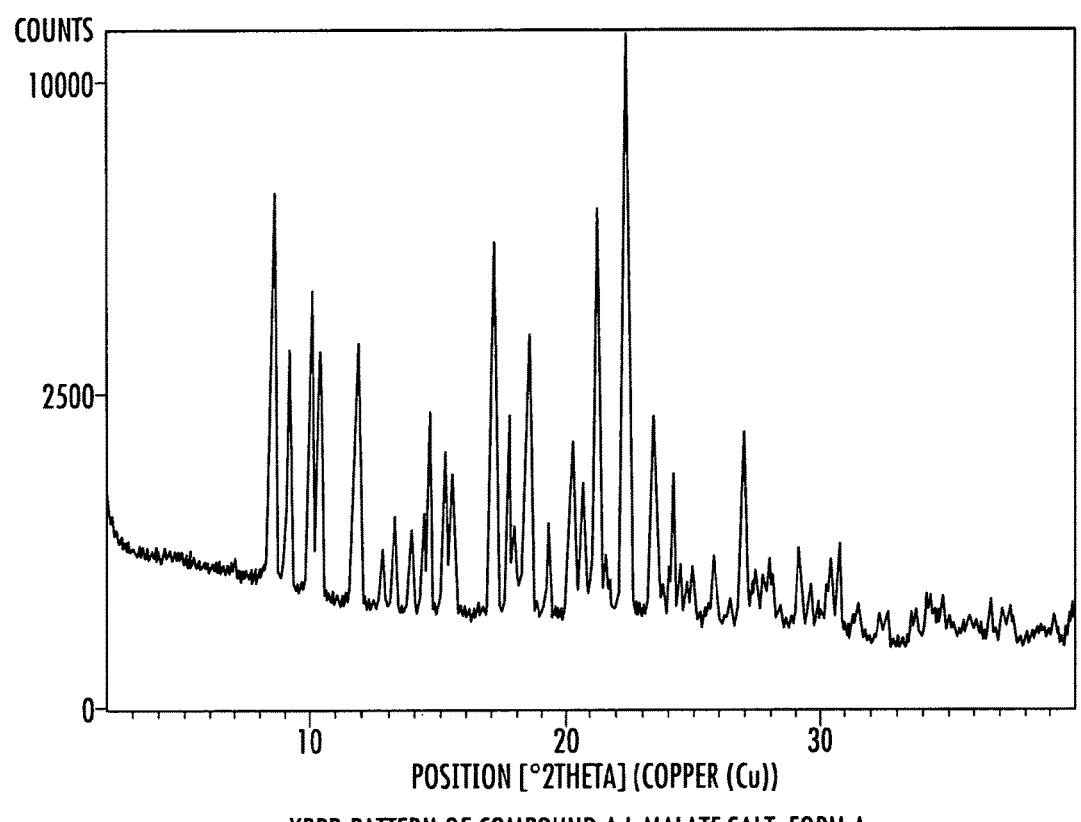
FIG. 14 shows an XRPD Pattern of Compound A L-Malate Salt, Form $A_1$.

Yet another embodiment of the disclosure pertains to Compound A, L-malate salt Form $A_1$. In one aspect, this crystalline form is characterized by an X-ray diffraction pattern comprising one or more of the following peaks: 8.6, 9.2, 10.1, 10.4, 11.7, 11.9, 14.7, 15.3, 15.6, 17.2, 17.8, 18.5, 20.3, 20.7, 21.2, 22.4, 23.5, 24.3, and/or 27.0±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 14.

Figure 19:
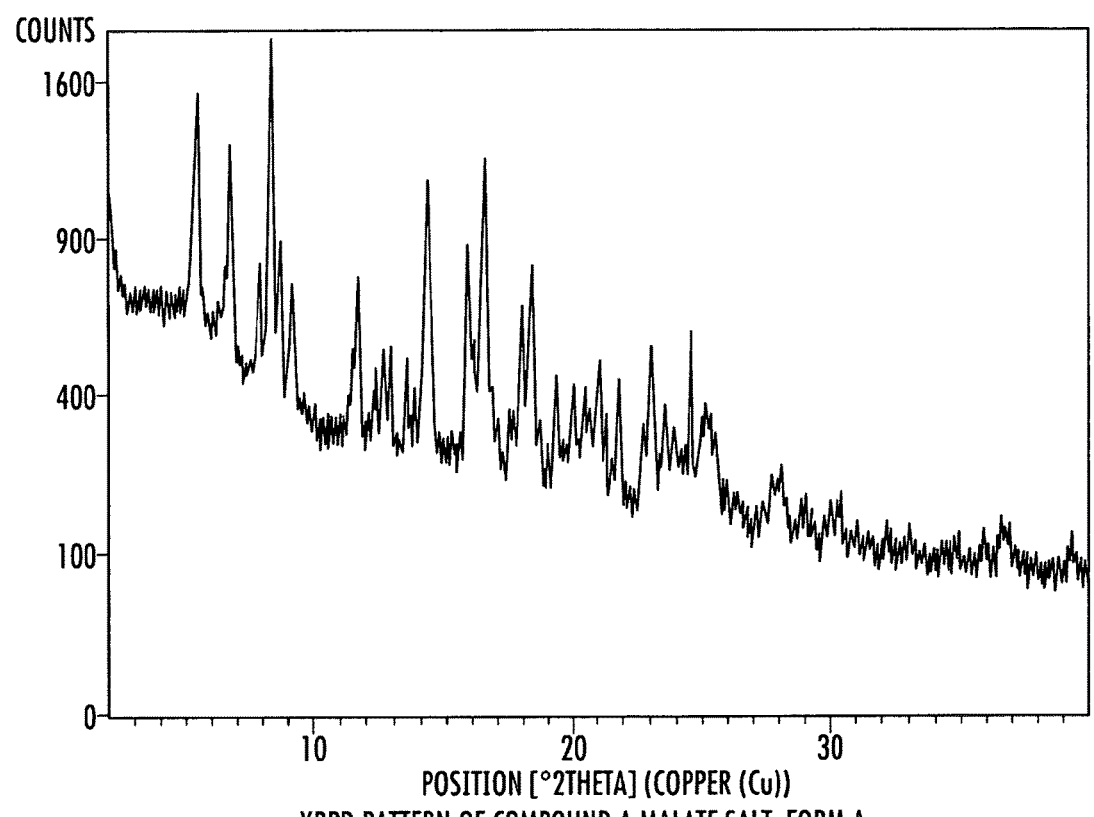
FIG. 19 shows an XRPD Pattern of Compound A L-Malate Salt, Form $A_{1.5}$.

In another embodiment, the disclosure pertains to Compound A, L-malate salt Form $A_{1.5}$. In one aspect, this crystalline form is characterized by an X-ray diffraction pattern comprising one or more of the following peaks: 5.5, 6.8, 8.0, 8.4, 8.8, 9.2, 11.8, 12.8, 13.1, 13.6, 14.4, 16.0, 16.7, 18.1, 18.5, 19.4, 20.2, 20.5, 21.1, 21.9, 23.4, and/or 24.6±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 19.

Figure 21:
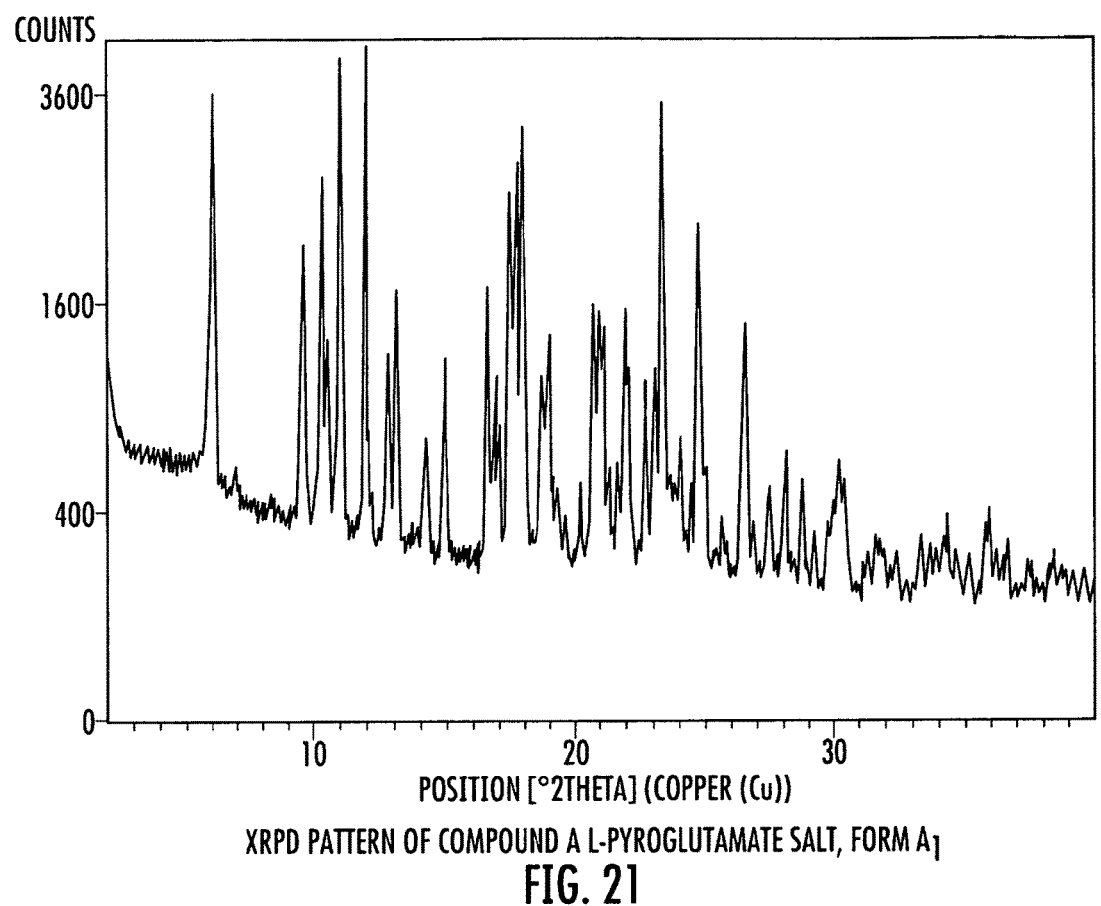
FIG. 21 shows an XRPD Pattern of Compound A L-Pyroglutamate Salt, Form $A_1$.

Also described herein is Compound A, L-pyroglutamate salt Form $A_1$. In one aspect, this crystalline form is characterized by an X-ray diffraction pattern comprising one or more of the following peaks: 6.0, 9.6, 10.3, 10.5, 11.0, 12.0, 13.2, 15.0, 16.7, 17.5, 17.8, 18.0, 19.0, 20.8, 21.0, 21.1, 22.0, 22.1, 23.1, 23.4, 23.5, 24.8, and/or 26.6±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 21.

Figure 27:
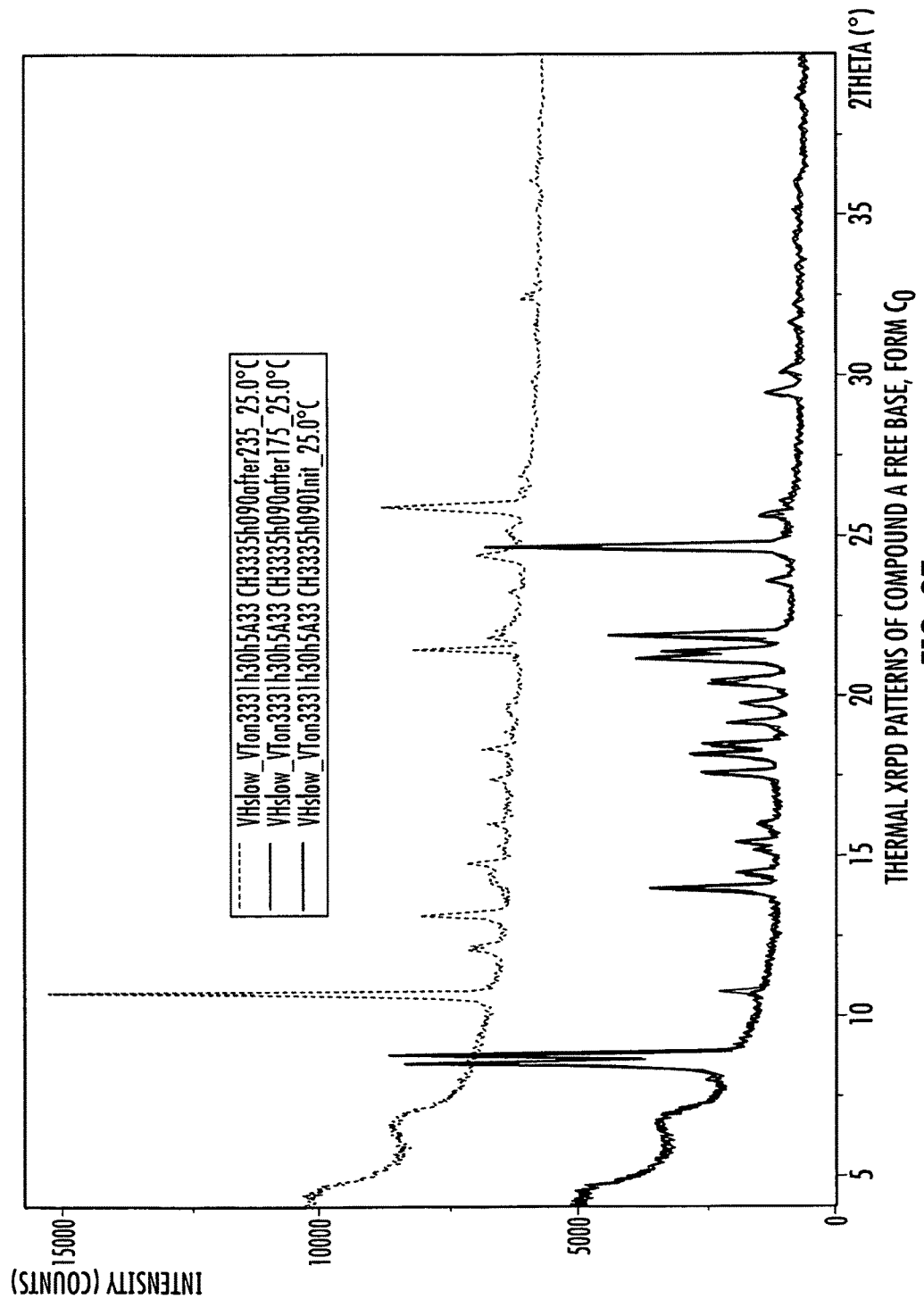
FIG. 27 shows thermal XRPD Patterns of Compound A Free Base, Form $C_0$.

The present disclosure also pertains to Compound A, free base Form $C_0$. In one aspect, this crystalline form is characterized by an X-ray diffraction pattern comprising one or more of the following peaks: 8.5, 8.8, 13.9, 14.4, 15.4, 17.6, 18.1, 18.5, 19.2, 19.7, 20.4, 21.1, 21.4, 21.9, 23.6, 24.6, 29.4 and/or 30.1±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 27.

Figure 30:
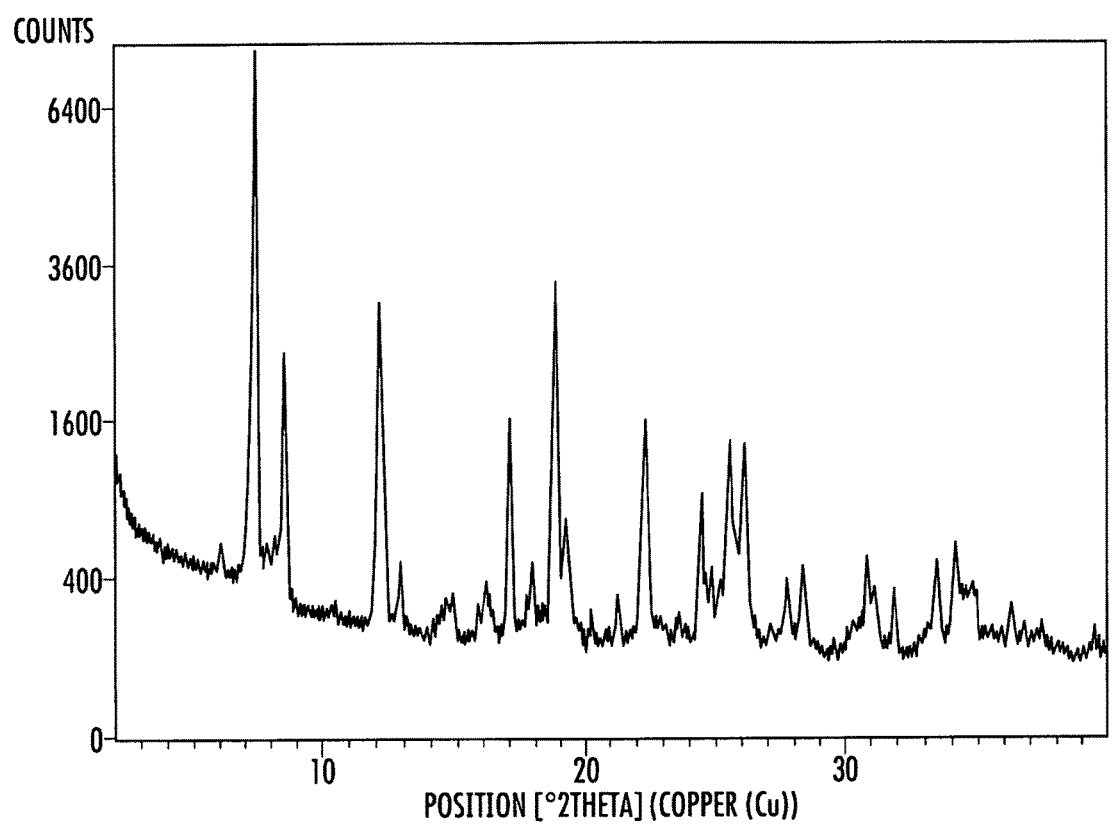
FIG. 30 shows an XRPD Pattern of Compound A Hydrochloride Salt, Form A.

Another embodiment of the present disclosure pertains to Compound A, hydrochloride salt Form A. In one aspect, this crystalline form is characterized by an X-ray diffraction pattern comprising one or more of the following peaks: 7.5, 8.6, 12.2, 17.1, 18.8, 18.9, 22.3, 24.5, 25.6, 26.1, 33.5, and/or 34.1±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 30.

Yet another embodiment of the present disclosure pertains to Compound A, fumarate salt Form A. In one aspect, this crystalline form is characterized by an X-ray diffraction pattern comprising one or more of the following peaks: 9.0, 10.5, 11.1, 14.9, 17.1, 17.7, 19.3, 21.1, 22.3, 22.9, 23.5, 24.0, 24.2, 25.7, 25.9, 27.3, 29.0, and/or 31.1±0.2 degrees 2-theta.

Figure 33:
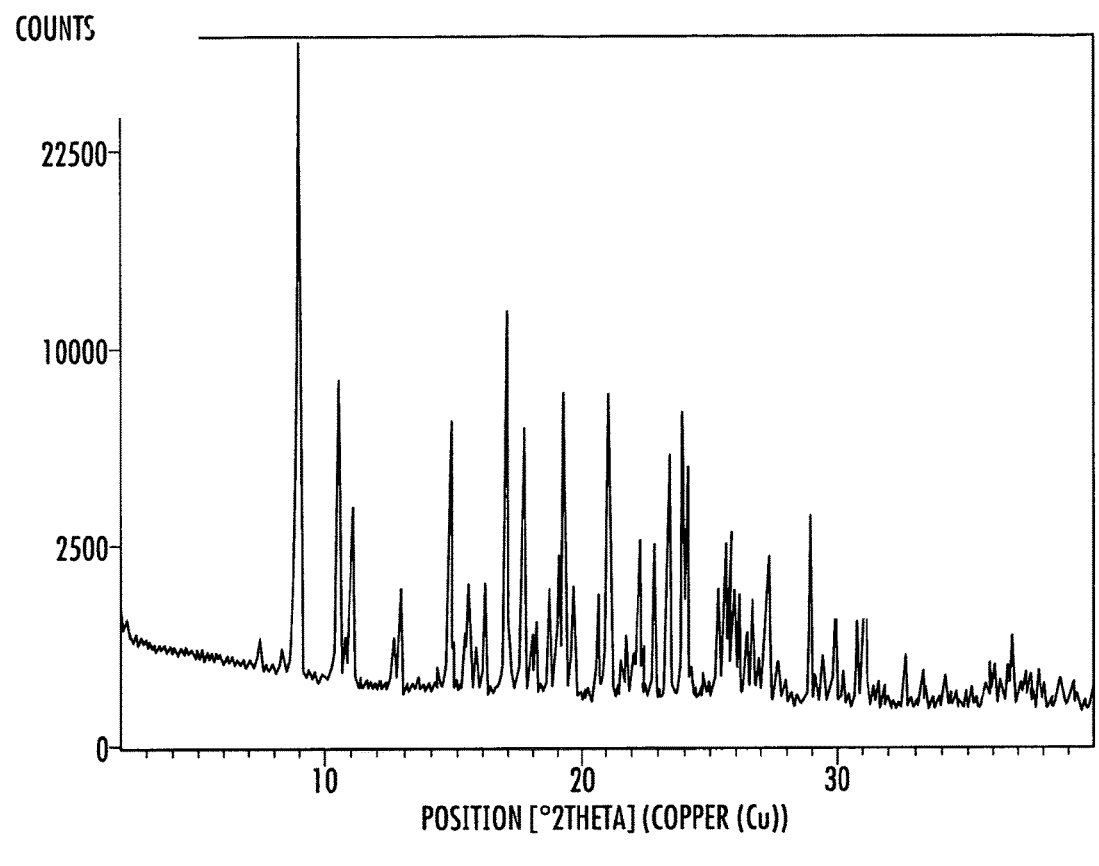
FIG. 33 shows an XRPD Pattern of Compound A Fumarate Salt, Form A.

In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 33.

Figure 35:
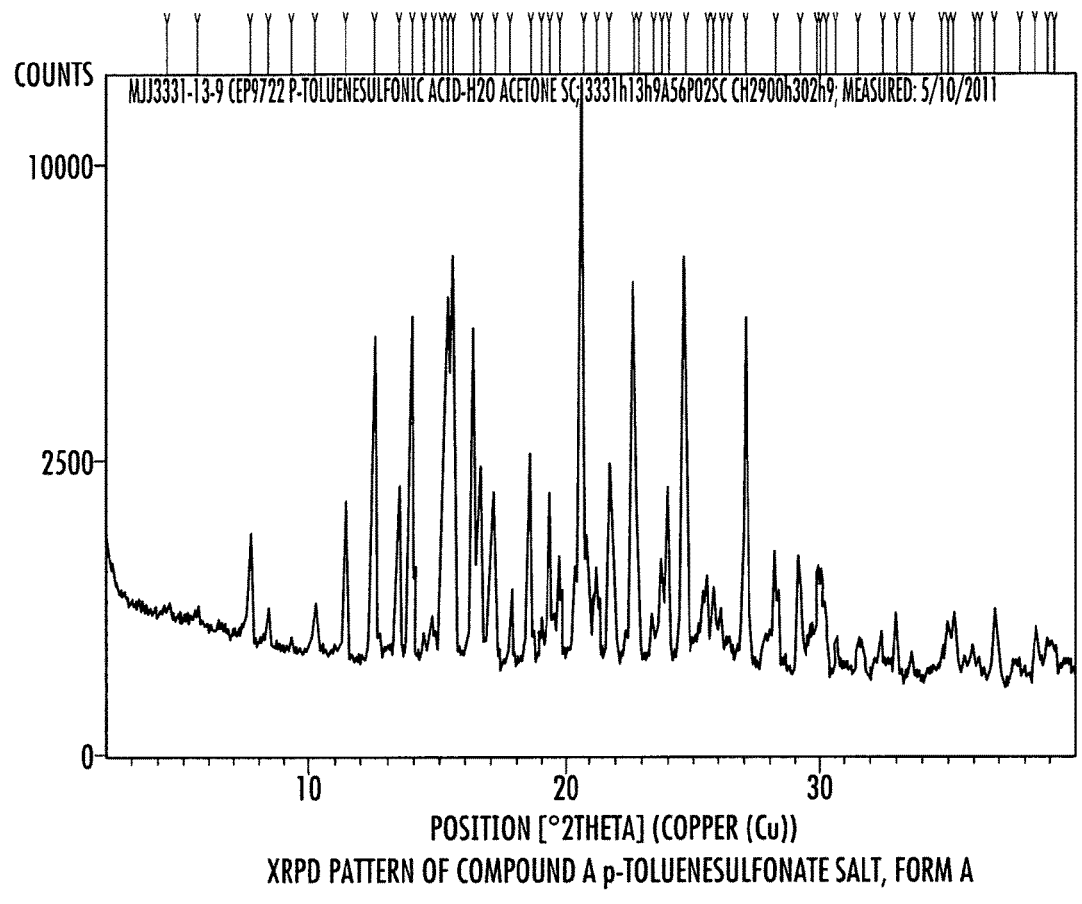
FIG. 35 shows a XRPD Pattern of Compound A p-Toluenesulfonate Salt, Form A.

And yet another embodiment of the present disclosure pertains to Compound A, p-toluenesulfonate salt Form A. In one aspect, this crystalline form is characterized by an X-ray diffraction pattern comprising one or more of the following peaks: 6.0, 9.6, 10.3, 10.5, 11.0, 12.0, 12.9, 13.2, 15.0, 16.7, 17.0, 17.5, 17.8, 18.0, 19.0, 20.8, 21.0, 21.1, 22.1, 22.7, 23.1, 23.4, 23.5, 24.8, and/or 26.6±0.2 degrees 2-theta. In another aspect, this crystalline form comprises at least 3 of the foregoing peaks. In yet another aspect, this crystalline for comprises at least 4, 5, 6, 7, 8, 9, or 10 of the foregoing peaks. In another aspect, this crystalline form has an X-ray powder diffraction pattern substantially as depicted in FIG. 35.

In some embodiments, the polymorphic forms of the disclosure are substantially free of any other polymorphic forms, or of specified polymorphic forms. In any embodiment of the present invention, by "substantially free" is meant that the forms of the present invention contain 20% (w/w) or less, 10% (w/w) or less, 5% (w/w) or less, 2% (w/w) or less, particularly 1% (w/w) or less, more particularly 0.5% (w/w) or less, and most particularly 0.2% (w/w) or less of either any other polymorphs, or of a specified polymorph or polymorphs. In other embodiments, the polymorphs of the disclosure contain from 1% to 20% (w/w), from 5% to 20% (w/w), or from 5% to 10% (w/w) of any other polymorphs or of a specified polymorph or polymorphs.

The salts and solid state forms of the present invention have advantageous properties including at least one of: high crystallinity, solubility, dissolution rate, morphology, thermal and mechanical stability to polymorphic conversion and/or to dehydration, storage stability, low content of residual solvent, a lower degree of hygroscopicity, flowability, and advantageous processing and handling characteristics such as compressibility, and bulk density.

A crystal form may be referred to herein as being characterized by graphical data "as substantially depicted in" a Figure. Such data include, for example, powder X-ray diffractograms. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

The term "amorphous," as used herein, means lacking a characteristic crystal shape or crystalline structure.

The term "crystalline," as used herein, means having a regularly repeating arrangement of molecules or external face planes.

The term "crystalline form," as used in herein, refers to a solid chemical compound or mixture of compounds that provides a characteristic pattern of peaks when analyzed by x-ray powder diffraction; this includes, but is not limited to, polymorphs, solvates, hydrates, co-crystals, and de-solvated solvates.

The term "polymorphic" or "polymorphism" is defined as the possibility of at least two different crystalline arrangements for the same chemical molecule.

The term "solution," as used herein, refers to a mixture containing at least one solvent and at least one compound at least partially dissolved in the solvent.

The term "pharmaceutically acceptable excipients," as used herein, includes any and all solvents, dispersion media, coatings, antibacterial and antifungal agents, isotonic and absorption delaying agents and the like. The use of such media and agents for pharmaceutical active substances is well known in the art, such as in Remington: The Science and Practice of Pharmacy, 20th ed.; Gennaro, A. R., Ed.; Lippincott Williams & Wilkins: Philadelphia, Pa., 2000. Except insofar as any conventional media or agent is incompatible with the active ingredient, its use in the therapeutic compositions is contemplated. Supplementary active ingredients can also be incorporated into the compositions.

The pharmaceutical compositions of the present invention may be used in a variety of ways, including but not limited to the enhancement of the anti-tumor activity of radiation or DNA-damaging chemotherapeutic agents (Griffin, R. J.; Curtin, N. J.; Newell, D. R.; Golding, B. T.; Durkacz. B. W.; Calvert, A. H. The role of inhibitors of poly(ADP-ribose) polymerase as resistance-modifying agents in cancer therapy. Biochemie 1995, 77, 408).

For therapeutic purposes, the crystalline forms of the present invention can be administered by any means that results in the contact of the active agent with the agent's site of action in the body of the subject. The crystalline forms may be administered by any conventional means available for use in conjunction with pharmaceuticals, either as individual therapeutic agents or in combination with other therapeutic agents, such as, for example, analgesics. The crystalline forms of the present invention are preferably administered in therapeutically effective amounts for the treatment of the diseases and disorders described herein to a subject in need thereof.

In therapeutic or prophylactic use, the crystalline forms of the present invention may be administered by any route that drugs are conventionally administered. Such routes of administration include intraperitoneal, intravenous, intramuscular, subcutaneous, intrathecal, intracheal, intraventricular, oral, buccal, rectal, parenteral, intranasal, transdermal or intradermal. Administration may be systemic or localized.

The crystalline forms described herein may be administered in pure form, combined with other active ingredients, or combined with pharmaceutically acceptable nontoxic excipients or carriers. Oral compositions will generally include an inert diluent carrier or an edible carrier. Pharmaceutically compatible binding agents, and/or adjuvant materials can be included as part of the composition. Tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. Further, a syrup may contain, in addition to the active compounds, sucrose as a sweetening agent and certain preservatives, dyes, colorings, and flavorings.

Alternative preparations for administration include sterile aqueous or nonaqueous solutions, suspensions, and emulsions. Examples of nonaqueous solvents are dimethylsulfoxide, alcohols, propylene glycol, polyethylene glycol, vegetable oils such as olive oil and injectable organic esters such as ethyl oleate. Aqueous carriers include mixtures of alcohols and water, buffered media, and saline. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

Preferred methods of administration of the crystalline forms to mammals include intraperitoneal injection, intramuscular injection, and intravenous infusion. Various liquid formulations are possible for these delivery methods, including saline, alcohol, DMSO, and water based solutions. The concentration may vary according to dose and volume to be delivered and can range from about 1 to about 1000 mg/mL. Other constituents of the liquid formulations can include preservatives, inorganic salts, acids, bases, buffers, nutrients, vitamins, or other pharmaceuticals such as analgesics or additional PARP and kinase inhibitors.

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to limit its scope in any way.

EXAMPLES

Solvents used in the following examples were of reagent-grade quality and were used without further purification. Known forms of Compound A are indicated by $A_0$ and $B_0$ for anhydrous material and $H_d$ for hydrate.

X-Ray Powder Diffraction (XRPD).

Standard Reflection Mode Measurements:

Powder X-ray diffraction patterns were recorded on a PANalytical X Pert Pro diffractometer equipped with an X'celerator detector using $CuK_\alpha$ radiation at 45 kV and 40 mA. $K_{\alpha 1}$ radiation was obtained with a highly oriented crystal (Ge111) incident beam monochromator. A 10 mm beam mask, and fixed (¼°) divergence and anti-scatter (⅛°) slits were inserted on the incident beam side. A fixed 5 mm receiving slit and a 0.04 radian Soller block were inserted on the diffracted beam side. The X-ray powder pattern scan was collected from ca. 2 to 40° 2θ with a 0.0080° step size and 96.06 sec counting time which resulted in a scan rate of approximately 0.5°/min. The sample was spread on silicon zero background (ZBG) plate for the measurement. The sample was rotated using a PANalytical PW3064 Spinner (15 revolutions/min.).

Measurement of the Si reference standard before the data collection resulted in values for 2θ and intensity that were well within the tolerances of 28.44<2θ<28.50 and significantly greater than the minimum peak height of 150 cps.

SCXRD—Single Crystal X-ray Diffraction:

For data collection, a piece (0.12×0.04×0.03 mm3) was broken from a clump of about three or four separate pieces to give an apparently single crystal. The crystal was mounted on a fine glass fiber with the aid of polyisobutene oil (also known as PARATONE) onto a Bruker-Nonius X8 Proteum diffractometer attached to a Nonius FR-591 rotating anode (CuKa) with 'Helios' focusing optics. The crystal was maintained at 90K throughout with a CryoCool LT2 from CryoIndustries of America. Diffraction images for indexing clearly showed split reflections, consistent with either cracking or twinning, but with spot components that were close enough to be integrated together. The relative intensities of pairs of split reflections suggested that cracking was more likely than twinning.

The crystal was indexed from the reflections found in 72 diffraction images (six sets of twelve 0.5° frames). Data collection consisted of 1485 2° frames in 15 scans at three detector swing angles (two 360° φ-scans at −40° in 2θ, three 90° ω-scans at −45° in 2θ, four 360° φ-scans at −96° in 2θ and six 90° ω-scans at −96° in 2θ) sufficient to cover reciprocal space for an arbitrarily oriented triclinic crystal to a resolution of 0.83 Å with four-fold redundancy. Data were integrated, scaled, averaged and merged using the programs in the APEX2 package from Bruker-AXS. Final cell parameters were derived from the output diagnostics of the integration process. The structure was solved by standard direct methods using SHELXS and refined using SHELXL, both from the SHELX97 package. Diagrams were drawn using XP from the SHELXTL suite and with Mercury from the CCDC. Additional molecular graphics and void calculation were done with Platon.

Positional and anisotropic displacement parameters of all non-hydrogen atoms were refined. The H atoms were located in a difference Fourier's map, but those attached to carbon atoms were repositioned geometrically. The H atoms were initially refined with soft restraints on the bond lengths and angles to regularize their geometry (C—H in the range 0.93-0.98 and N—H to 0.86 Å) and Uiso(H) (in the range 1.2-1.5 times Ueq of the parent atom), after which the positions were refined with riding constraints.

Default Reitveld refinement of the single crystal unit cell parameters against the measured XRPD pattern gave a good fit with no unexplained peaks.

Variable Temperature X-Ray Powder Diffraction (VT-XRPD):

Variable temperature studies were performed with an Anton Paar CHC temperature/humidity chamber under computer control through an Anton Paar TCU110 temperature control unit.

Typically the measurements were done with a nitrogen flow through the camera. Two measurement schemes were used, restricted and continuous. In the restricted mode, measurements were made, only after the CHC chamber reached the requested temperature. In the continuous mode, the sample was heated at 10° C./minute and fast scans were measured as the temperature changed. In both cases, after the requested temperature was reached, the sample was cooled at 35° C./minute and a slow scan was measured at 25° C. The slow 2θ scans were collected from ca. 3 to 30° or 40° with a 0.0080° step size and 100.97 sec counting time which resulted in a scan rate of approximately 0.5°/min. The fast scans were collected from ca. 3 to 30° 2θ with a 0.0167° step size and 1.905 sec counting time which resulted in a scan rate of approximately 44°/min.

The temperatures chosen were based on DSC results.

For the diffractometer set-up a 10 mm beam mask, 0.04 radian Soller slits, and fixed (¼°) divergence and anti-scatter (⅛°) slits were inserted on the incident beam side. A fixed 5 mm receiving slit, 0.04 radian Soller slits and a 0.02 mm Nickel filter were inserted on the diffracted beam side.

Differential Scanning Calorimetry (DSC):

Thermal curves were acquired using a Perkin-Elmer Sapphire DSC unit equipped with an autosampler running Pyris software version 6.0 calibrated with Indium prior to analysis. Solid samples of 1-10 mg were weighed into 20 µL aluminum pin hole sample pans. The DSC cell was then purged with nitrogen and the temperature heated from 0 to 270° C. at 10° C./min. Indium ($T_m$=156.6° C.; $\Delta H_{FUS}$=28.45 J g$^{-1}$) was used for calibration.

Modulated Differential Scanning Calorimetry (MDSC):

Thermal curves were acquired using a TA Q200 Modulated DSC unit. Solid samples of 5-20 mg were weighed into 50 µL aluminum pinhole hermetically sealed pans. The MDSC cell was then purged with nitrogen and the temperature heated at 2° C./min from 0° C. to 350° C. at 2° C./min with a modulation amplitude of +/−1° C. over a 60 second period.

Thermogravimetric Mass Spectrometry (TGA/MS):

Thermal curves were acquired using a Perkin-Elmer Pyris 1 TGA unit running Pyris software version 6.0 calibrated with alumel (95% nickel, 2% manganese, 2% aluminum and 1% silicon), nickel and calcium oxalate monohydrate. TGA samples between 1-5 mg were monitored for percent weight loss as heated from 25 to 250° C. at 10° C./min in a furnace purged with Helium at ca. 50 mL/min. To simultaneously follow the evolution of the gaseous decomposition products over the temperature range investigated, the thermobalance was connected to a ThermoStar Quadrupole Mass Spectrometer (Asslar, Germany). The transfer line to introduce gaseous decomposition products into the mass spectrometer was a deactivated fused silica capillary (SGE Analytical science, Fused Silica (100% Methyl Deactivated), 220 mm OD, 150 mm ID, Australia) temperature controlled to 200° C. to avoid possible condensation of the evolved gases. In this way the TGA weight loss and the mass spectrometric ion intensity curves of the selected ionic species could be recorded simultaneously.

Dynamic Vapor Sorption (DVS):

DVS experiments have been carried out using the DVS-HT instrument (Surface Measurement Systems, London, UK). This instrument measures the uptake and loss of vapor gravimetrically using a recording ultra-microbalance with a mass resolution of ±0.1 µg. The vapor partial pressure (±1.0%) around the sample is controlled by mixing saturated and dry carrier gas streams using electronic mass flow controllers. The desired temperature is maintained at ±0.1° C. The samples (1-10 mg) were placed into the DVS-HT and DVS-1 instruments at the desired temperature.

The sample was loaded and unloaded at 40% RH and 25° C. (typical room conditions). A moisture sorption isotherm was performed as outlined below (2 scans giving 1 complete cycle). The software uses a least squares minimization procedure together with a model of the mass relaxation, to predict an asymptotic value. The measured mass equilibration value must be within 2% of that predicted by the software before proceeding to the next % RH value. The minimum equilibration time was set to 1 hour and the maximum to 4 hours.

Optical Microscopy:

Microscopic observation of the sample morphology was performed using an Olympus B60 polarized light microscope. Samples were suspended in mineral oil and compressed on a glass slide with a cover slip prior to observation. Images were taken with a FW-24 (PAX CAM) camera. A 10× objective coupled with an additional 10× magnification from the microscope optics gave a total magnification of 100×. PAX-it software (Version 6.2) was used to capture and analyze the images.

Nuclear Magnetic Resonance Spectroscopy ($^1$H-NMR):

The stoichiometry of the salts were determined by $^1$H-NMR spectroscopy using a Bruker DPX400 instrument running under conditions optimized to give the best available spectrum for each sample. Each sample (2-4 mg) was dissolved in 0.75 mL DMSO-d6 and spectrum obtained in thin walled glass tubes (4×14 mm).

Identity, Assay, and Purity by HPLC

Equipment:

Testing was performed on a calibrated and validated Agilent 1200 Rapid Resolution High Performance Liquid Chromatography (HPLC) system designated LC-0430-AD or LC-418-1D. The system comprises a binary SL pump, degasser, high performance autosampler SL with a fraction collector, thermostated column compartment with a 2 valve column switcher, and a DAD SL detector. All standard solutions and samples were prepared in Class A glass volumetric flasks and were placed in autosampler vials. Standard weighings were done using a calibrated Mettler analytical balance. The sample preparations were centrifuged using an Eppendorf microcentrifuge. The primary chromatography data was acquired and integrated using Empower 2 software. Microsoft Office Excel 2003 was used for the calculation of results.

Reagents:

Acetonitrile was obtained from CCI. Trifluoroacetic acid was obtained from EMD. HPLC grade water (18 MΩ·cm) was obtained from the laboratory Barnstead Nanopure system UPW-0403-AD located in laboratory A211. Compounds A and B were prepared as previously described.

Instrument Parameters:

Column: Zorbax Eclipse XDB-C18, 100 × 3.0 mm ID, 1.8µ packing
Detector: UV/vis @ 290 nm
Column Temperature: 25° C.
Flow Rate: 0.64 mL/min
Mobile Phase A: 0.1% TFA in water
Mobile Phase B: 0.1% TFA in ACN

| Gradient: | | |
|---|---|---|
| Time (min) | Mobile Phase A (%) | Mobile Phase B (%) |
| 0 | 75 | 25 |
| 10 | 55 | 45 |
| 12 | 5 | 95 |
| 13 | 5 | 95 |
| 13.1 | 75 | 25 |
| 16.7 | 75 | 25 |

Solid State Stability of Salts at 40° C. and 75% Humidity:

Samples of the form to be studied (15-20 mg) were weighed into standard 1.5 mL HPLC vials (32×11.6 mm) and stored uncapped for 0, 7, 14 and 28 days in a 40° C. and 75% RH stability chamber. Samples were removed on the indicated day and capped. Measurements of XRPD, DSC, TGA and HPLC Identity by Purity and Assay measurements were completed on each time point sample.

Estimation of Water Solubility:

Ten mg portions of the salt forms to be studied were weighed into a standard 1.5 mL HPLC vial (32×11.6 mm). A stir bar and 100 µL of water were added to each vial. The samples were capped and stirred for 5-10 minutes. If a clear solution was not obtained by visual inspection, an additional 100-300 µL portion of water was added and stirred. This process was repeated until the sample dissolved or until 1000 µL of water was added. An estimation of solubility was based on the volume of water necessary to dissolve the known weight of sample. The results from these measurements are presented in Table 11.

TABLE 1

Estimated Water Solubility and HPLC analyses of Salts with One Equivalent of Acid in Acetone by Slow Cooling

| Sample | Acid | Estimated Water Solubility | Measured COMPOUND A, % | Calculated Di Salt, % | Calculated Mono Salt, % |
|---|---|---|---|---|---|
| 13-3 | Acetic | 50-100 mg/mL | 72.2 | 77.0 | 87.5 |
| 13-4 | Fumaric | <10 mg/mL | 1.9 | | |
| 13-5 | Glycolic | <10 mg/mL[1] | 72.0 | 73.2 | 84.5 |
| 13-6 | L-Malic | >100 mg/mL | 68.3 | 61.0 | 75.8 |
| 13-7 | Phosphoric | 50-100 mg/mL | 5.9 | 68.4 | 81.2 |
| 13-8 | L-Pyroglutamic | >100 mg/mL | 56.0 | 61.8 | 76.4 |
| 13-9 | p-Toluenesulfonic | <10 mg/mL | 42.7 | 54.9 | 70.8 |
| 13-10 | Hydrochloric | 10-20 mg/mL | 39.8 | 85.1 | 92.0 |

Example 1. Salts with Two Equivalents of Acid in Acetone by Maturation 200 mg of Compound A (0.478 mmoles) was dissolved with warming and stirring in each of five-20 mL scintillation vials in 15 mL of acetone. 1.95 equivalents of acetic, glycolic, L-malic, or L-malic (1 Eq., 0.48 mmoles) acids were added to the clear Compound A solutions. As soon as these acids were added, the clear solutions became cloudy and began crystallizing. The vials were subject to two cycles of maturation on the HEL unit. Each cycle of maturation consisted of heating to 50° C. over a period of one hour, holding at 50° C. for four hours, cooling over a period of one hour to 5° C., and holding at 5° C. for four hours. The solid was isolated by suction filtration and solid dried overnight at 50° C. and house vacuum (~200 mm) to give yellow solids. The results are presented in Table 2.

TABLE 2

| Sample | Acid | XRPD | DSC, ° C. | TGA, % | Estimated Water Solubility |
|---|---|---|---|---|---|
| 39-1(2) | Acetic | $A_{1.5}$ | 185.2 | 24.4 | ~25 mg/mL |
| 39-2(2) | Glycolic | $A_1$ | 68.9, 205.4 | 4.8 | >100 mg/mL |
| 39-3(2) | L-Malic | $A_1$ | 186.4 | 3.6 | >100 mg/mL |
| 39-5(2) | L-Malic (1 eq.) | $A_1 + C_0$ | 186.5 | 1.0 | >100 mg/mL |

Example 2. Acid Screening (Two Equivalents) in Acetone Using Quick Cooling

To seven HPLC vials containing a stirring bar and 1.5 mL of Compound A solution (13.3 mg/mL), the quantities of acids to give two equivalents (0.096 mmoles) were weighed or added by pipette. The samples were capped and heated to the boiling point and then chilled overnight in the refrigerator at 2-8° C. The solid was isolated by suction filtration and solid dried overnight at 50° C. and house vacuum (~200 mm) to give yellow solids. The results are presented in Table 3.

TABLE 3

| Sample | Acid | XRPD | DSC, ° C. | TGA, % | Estimated Water Solubility |
|---|---|---|---|---|---|
| 31-1 | Acetic | $A_{1.5}$ | 181.3 | 22.6 | ~25 mg/mL |
| 31-2 | Glycolic | $A_1$ | 205.4 | 4.8 | >100 mg/mL |
| 31-3 | L-Malic | $A_{1.5}$ | 160.4 | 3.6 | >100 mg/mL |
| 31-4 | L-Pyroglutamic | $A_1$ | 196.4 | 4.4 | >100 mg/mL |
| 31-5 | L-Malic(1 eq.) | $C_0$ | 206.4 | 2.7 | ~25 mg/mL |

Example 3. Salts with Two Equivalents of Acid in Acetone by Slurry Conversion 400 mg of Compound A (0.956 mmoles) was slurried with warming and stirring in each of five 20 mL glass scintillation vials with 18 mL of acetone. Two equivalents of acetic, glycolic, L-malic, L-pyroglutamic or L-malic (1 Eq. (0.956 mmoles) acids were added to the COMPOUND A suspension in each vial. These mixtures were capped and warmed to near the boiling point. In all cases a heavy yellow solid was noted. The samples were allowed to cool to ambient temperature on the laboratory bench and chilled overnight in the refrigerator at 2-8° C. The solid was isolated by suction filtration and the product dried overnight at 50° C. and house vacuum (~200 mm) to give yellow solids. The results are presented in Table 4.

TABLE 4

| Sample | Acid | XRPD | DSC, ° C. | TGA, % | Estimated Water Solubility |
|---|---|---|---|---|---|
| 39-1 | Acetic | $A_{1.5}$ | 185.4, split peak | 2.1 | ~50 mg/mL |
| 39-2 | Glycolic | $A_1$ | 77.4, 209.0 | 1.9 | <10 mg/mL |
| 39-3 | L-Malic | $A_1$ | 193.3 | 3.6 | >100 mg/mL |
| 39-4 | L-Pyroglutamic | $A_1$ | 50.4, 198.2 | 3.5 | >100 mg/mL |
| 39-5 | L-Malic (1 eq.) | $A_1 + C_0$ | 192.2 | 1.0 | >100 mg/mL |

Example 4. Acid Screening (Two Equivalents) in Acetone-Maturation 240 mg of Compound A (0.574 mmoles) in 18 mL of acetone and warmed with stirring by a magnetic stirring bar to dissolve. This solution was dispensed equally to 12 1.5 mL HPLC vials.

To each of 5 vials containing an aliquot of the Compound A solution and a stirring bar, the quantities of acid to give two equivalents (0.096 mmoles) were weighed or added by pipette. The samples were capped and subject to two cycles of maturation on the HEL unit. Each cycle of maturation consisted of heating to 50° C. over a period of one hour, holding at 50° C. for four hours, cooling over a period of one hour to 5° C., and holding at 5° C. for four hours. The solid was isolated by suction filtration and solid dried overnight at 50° C. and house vacuum (~200 mm) to give yellow solids. The results are presented in Table 5.

TABLE 5

| Sample | Acid | XRPD | DSC, ° C. | TGA, % | Estimated Water Solubility. |
|---|---|---|---|---|---|
| 30-1 | Acetic | $A_{1.5}$ | 187.7, 334.1 | 21.7 | ~20 mg/mL |
| 30-2 | Glycolic | $A_1$ | 206.6 | 3.2 | >100 mg/mL |
| 30-3 | L-Malic | $A_1$ | 190.2 | 1.5 | >100 mg/mL |
| 30-4 | L-Pyroglutamic | $A_1$ | 197.5 | 1.8 | >100 mg/mL |
| 30-5 | L-Malic (1 eq.) | $C_0$ | 207.3 | 2.2 | ~25 mg/mL |

Example 5. One Equivalent in Acetone-Slow Cooling

A solution of 240 mg of Compound A (0.57 mmoles) was prepared in 12 mL of acetone and warmed with stirring to dissolve. Twelve equal aliquots of this solution will give 20 mg (0.0478 mmoles) of Compound A in 1 mL of acetone in each vial. The weight of acid corresponding to 1.05 equivalents (0.06 mmoles) of acid was weighed or added by pipette if liquid to 12 1.5 mL HPLC vials. To each vial one of the aliquots of Compound A was added. The vials were capped and warmed with stirring to mix and subject to 2 cycles of slow cooling on the HEL unit. Each cycle of slow cooling on the HEL unit consisted of heating over a period of 1 hour to 80° C. holding for 1 hour at 80° C. and then cooling over a period of 5 hours to 5° C. and holding at 5° C. for 16-18 hours. Solid was isolated by suction filtration and samples were dried at 50° C. overnight at house vacuum (~200 mm). The results are presented in Table 6.

TABLE 6

| Sample | Acid | DSC ° C. | TGA % |
|---|---|---|---|
| 1 | Acetic | 171.6 | 9.9 |
| 2 | L-Aspartic | 145.8, 191.2, 219.8, 240.5, 258.5 | 1.3 |
| 3 | Ethanesulfonic | 61.2, 193.6, EXO 199.8, 258.7 | 0.2 |
| 4 | Fumaric | 177.1 | 0.4 |
| 5 | Glycolic | 207.0 | 0.4 |
| 6 | L-Malic | 63.1, 198.6 | 1.5 |
| 7 | Phosphoric | 54.4 | 3.6 |
| 8 | L-Pyroglutamic | 199.6 | 0.4 |
| 9 | Sulfuric (0.5 eq) | 69.5, 201.0 | 3.7 |
| 10 | L-Tartaric | 66.0, 162.4 | 3.2 |
| 11 | p-Toluenesulfonic | 205.9 | 0.3 |
| 12 | Hydrochloric (EtOH) | 67.0, 234.3 | 0.9 |

*EXO = exotherm

Example 6. Preparation of Ascorbate Salt 200 mg of Compound A (0.478 mmoles) was weighed into a 20 mL glass scintillation vial with a stirring bar followed by 88.4 mg (0.503 mmoles, 1.05 equivalents) of ascorbic acid (J.T. Baker Anhydrous Lot B36597). 2.5 ml of 2,2,2-trifluoroethanol was added by pipette and the sample was warmed. The slurry that formed was subject to 2 cycles of slow cooling on the HEL unit. Each cycle of slow cooling on the HEL unit consisted of heating over a period of 1 hour to 80° C., holding for 1 hour at 80° C., and then cooling over a period of 5 hours to 5° C. and holding at 5° C. for 16-18 hours. Solid was isolated by suction filtration and samples were dried at 50° C. overnight at house vacuum (~200 mm) to give 142 mg of yellow solid (49% yield). The crystalline product was analyzed by HPLC and gave 96.2% of Compound B and 0.8% of Compound A. The structure of the Compound B salt was confirmed by $^1$H-NMR.

Compound A, Free Base, Form $A_0$

XRPD

Figure 1:
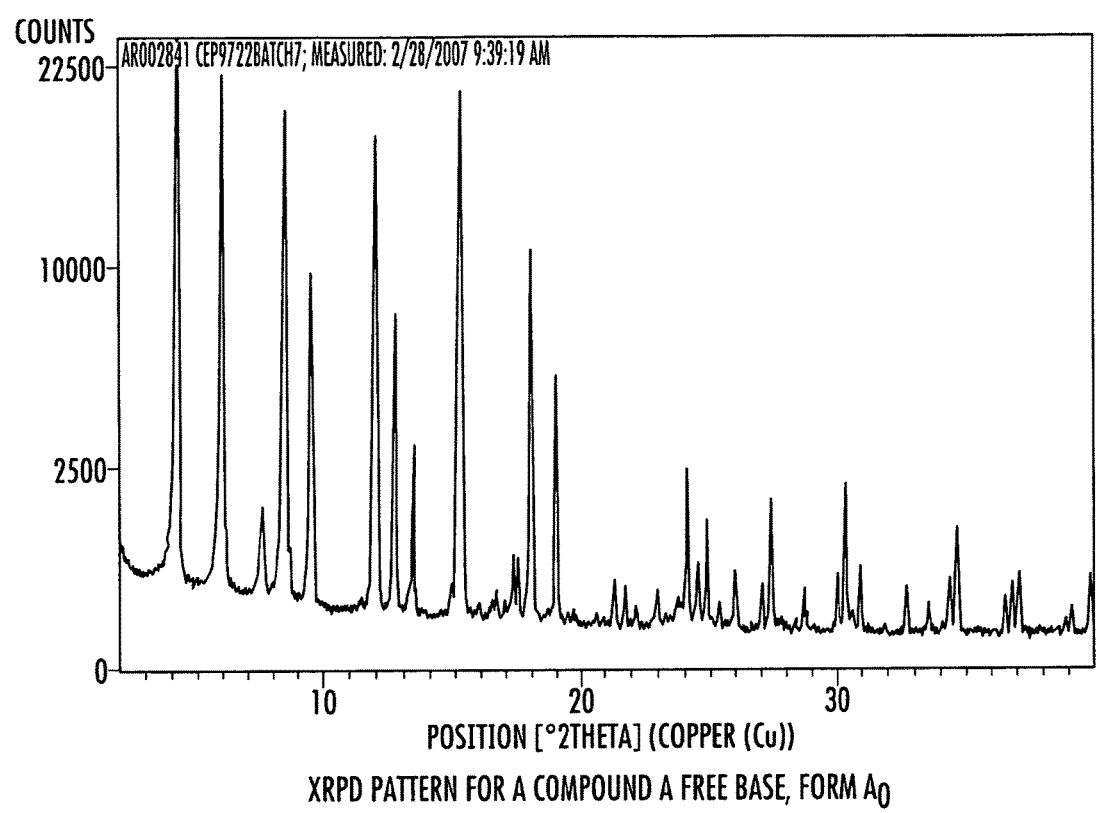
FIG. 1 shows an XRPD Pattern for Compound A Free Base, Form $A_0$.

The XRPD is depicted in FIG. 1.

Thermal Analysis

Figure 2:
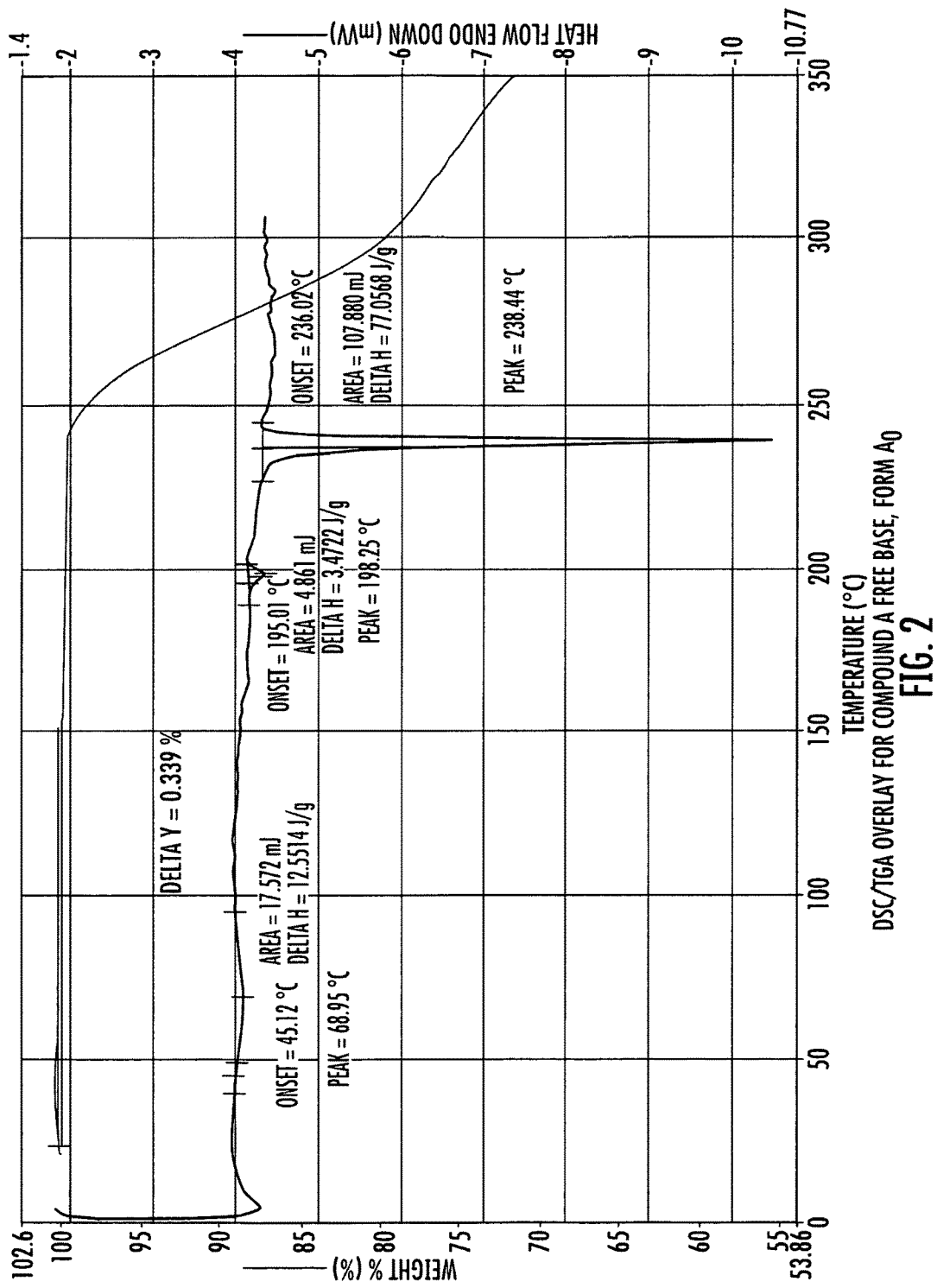
FIG. 2 shows a DSC/TGA Overlay for Compound A Free Base, Form $A_0$.

Thermal data is depicted in FIG. 2.

Compound A, Acetate Salt, Form $A_{1.5}$

Preparation

The salt was prepared according to the procedure in Example 1.

XRPD

Figure 4:
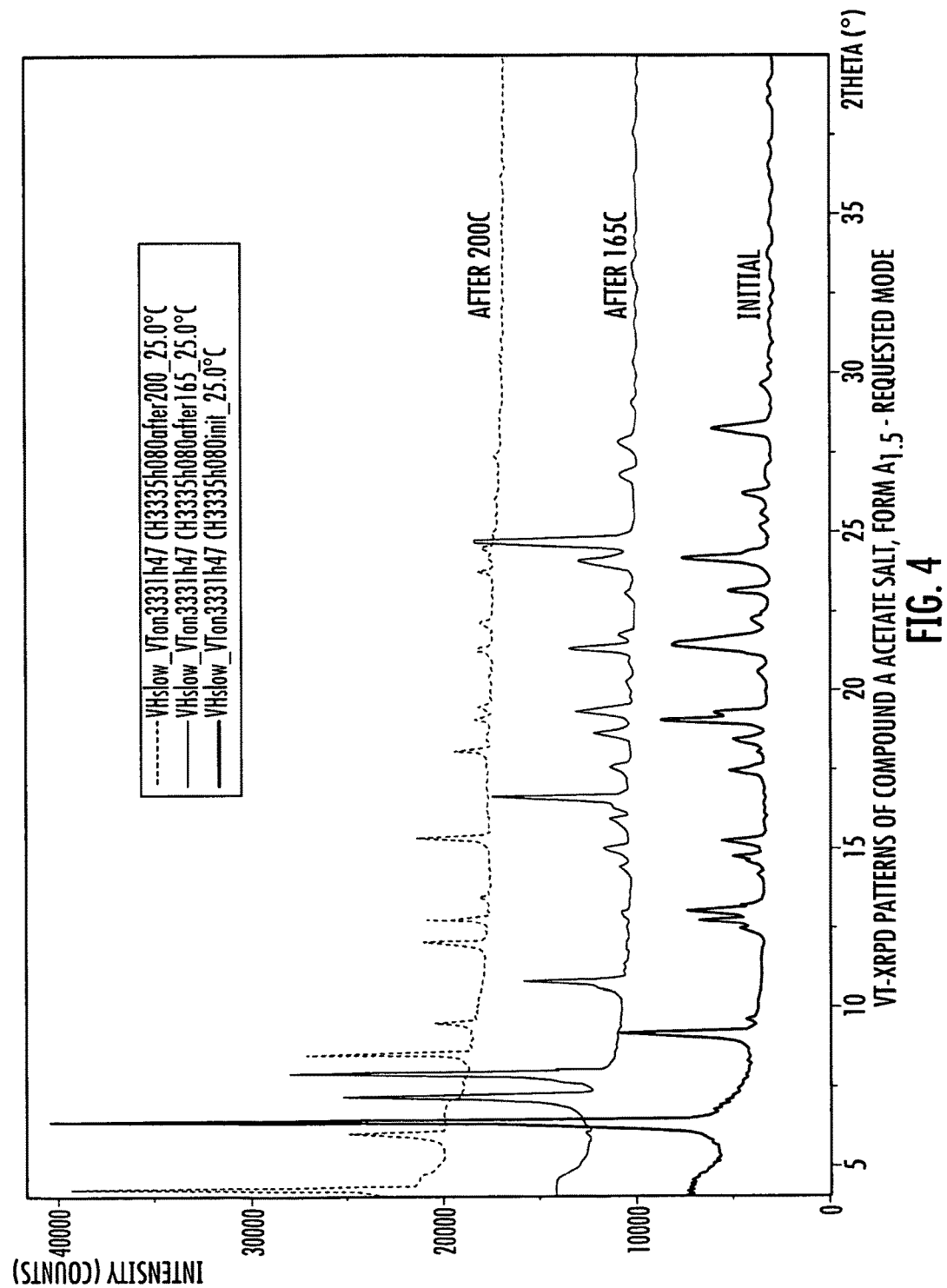
FIG. 4 shows VT-XRPD Patterns of Compound A Acetate Salt, Form $A_{1.5}$—Requested Mode.
Figure 5:
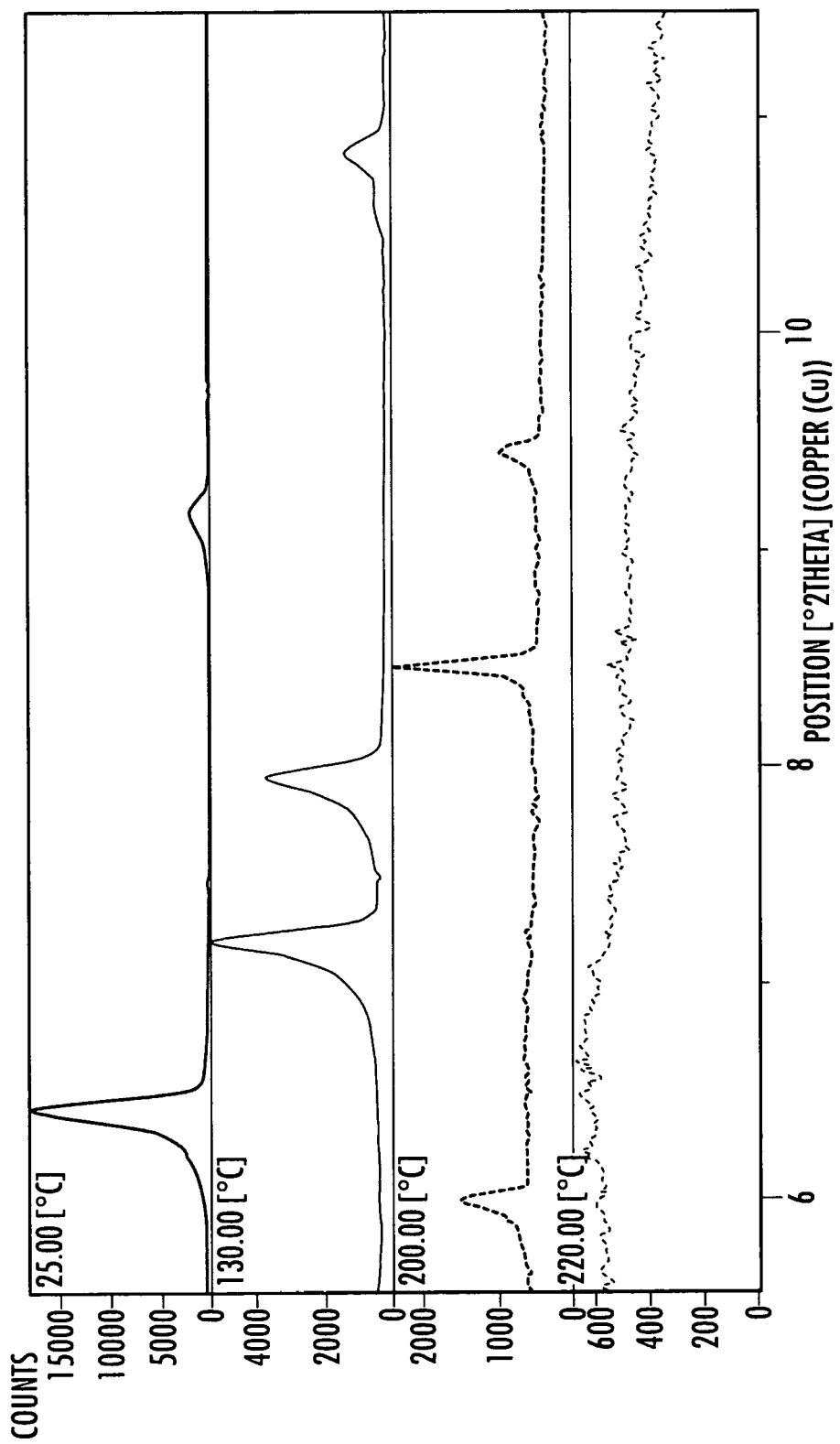
FIG. 5 shows VT-XRPD Patterns of Compound A Acetate Salt, Form $A_{1.5}$—Continuous Mode.

The X-ray diffraction data for the acetate salt, Form $A_{1.5}$, is given in FIG. 3 and Table 7. Variable temperature XRPD measurements in requested mode (165° C. and 200° C.) showed two changes in Form—from the acetate to Form $B_0$ and then conversion to Form $A_0$. In continuous mode, using one minute scans from 5.5° to 11.5° and a 1° C./minute temperature ramp, three changes in form were noted, acetate to Freebase $B_0$, $B_0$ to $A_0$ and $A_0$ to amorphous (FIG. 4). The acetate slowly converts to freebase Form $B_0$ over the temperature range 91° C. to 130° C. The form changes from $B_0$ to $A_0$ between 197° C. and 200° C. (FIG. 5).

TABLE 7

XRPD Peaks for the Acetate Salt, Form $A_{1.5}$

| No. | Pos. [2θ°]* | d-spacing [Å] | Rel. Int.[%] |
|---|---|---|---|
| 1 | 6.41 | 13.777 | 100 |
| 2 | 9.21 | 9.599 | 6 |
| 3 | 12.42 | 7.123 | 1 |
| 4 | 12.71 | 6.961 | 4 |
| 5 | 13.02 | 6.796 | 4 |
| 6 | 13.22 | 6.694 | 1 |
| 7 | 14.72 | 6.012 | 1 |
| 8 | 15.22 | 5.817 | 2 |
| 9 | 17.41 | 5.089 | 2 |
| 10 | 18.00 | 4.924 | 1 |
| 11 | 18.36 | 4.828 | 2 |
| 12 | 18.47 | 4.799 | 1 |
| 13 | 19.02 | 4.661 | 6 |
| 14 | 19.26 | 4.605 | 5 |
| 15 | 21.11 | 4.205 | 1 |
| 16 | 21.30 | 4.169 | 2 |
| 17 | 21.53 | 4.124 | 3 |
| 18 | 21.70 | 4.092 | 1 |
| 19 | 23.10 | 3.847 | 3 |
| 20 | 23.90 | 3.720 | 1 |
| 21 | 24.07 | 3.694 | 2 |
| 22 | 24.18 | 3.678 | 2 |
| 23 | 24.33 | 3.655 | 1 |
| 24 | 25.50 | 3.490 | 1 |
| 25 | 26.09 | 3.412 | 1 |
| 26 | 26.21 | 3.397 | 1 |
| 27 | 28.15 | 3.167 | 2 |
| 28 | 28.25 | 3.157 | 1 |

*The use of ZBG or glass plates typically introduces a positive sample height displacement and results in small (0.05° to 0.2°) offset in 2θ values. The highest peak (intensity 100%) is set in bold letters.

Thermal Analysis

Figure 6:
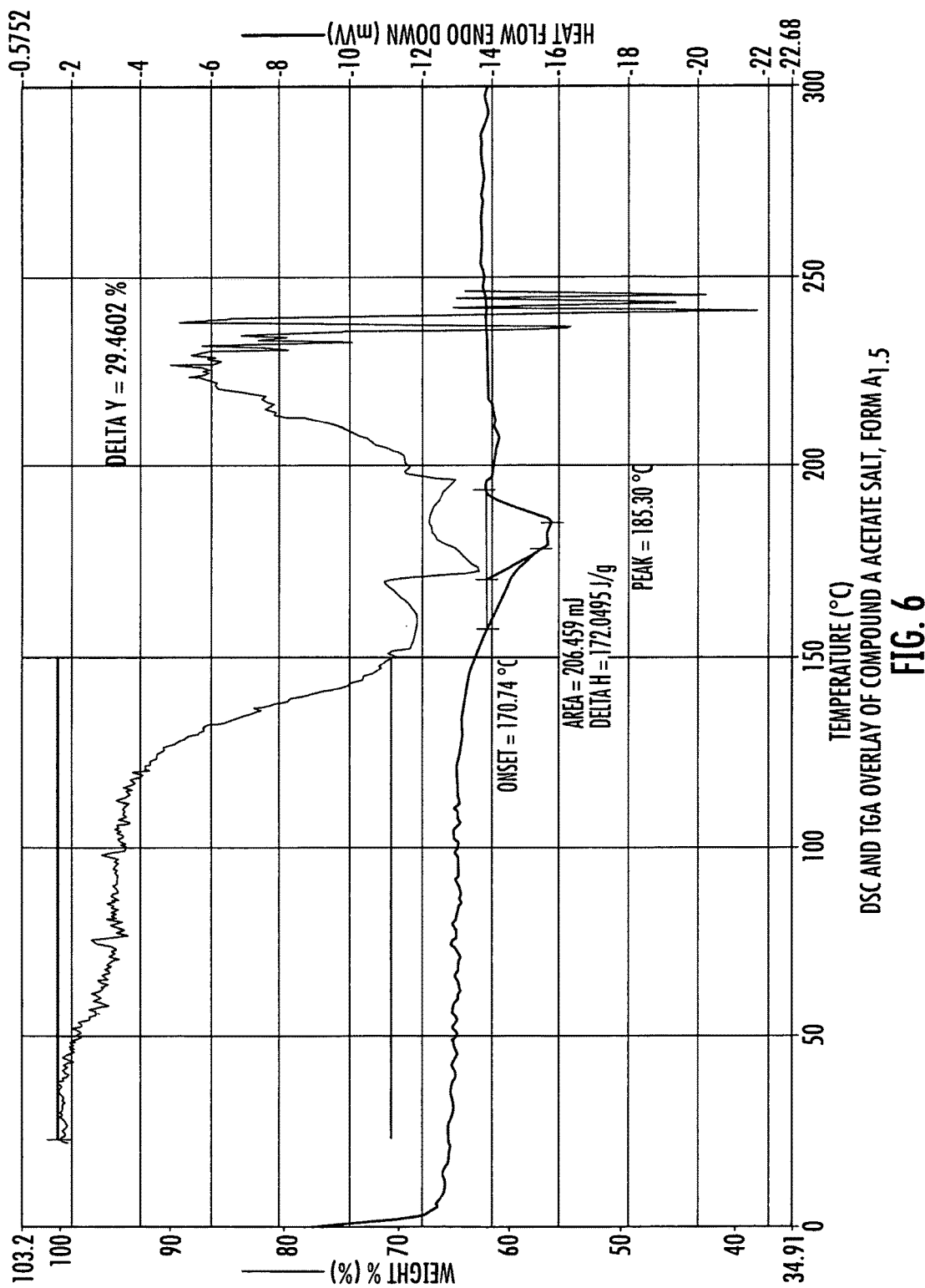
FIG. 6 shows a DSC and TGA Overlay of Compound A Acetate Salt, Form $A_{1.5}$.

The DSC curve of the acetate salt, Form $A_{1.5}$, shows the presence of one endothermic/degradation peak; at 185.4° C. having a $\Delta H_{Fus}$ of 172.0 J/g (FIG. 6). The acetate salt had a weight loss of 29.5% between 25 and 150° C.

Water Sorption

Figure 7:
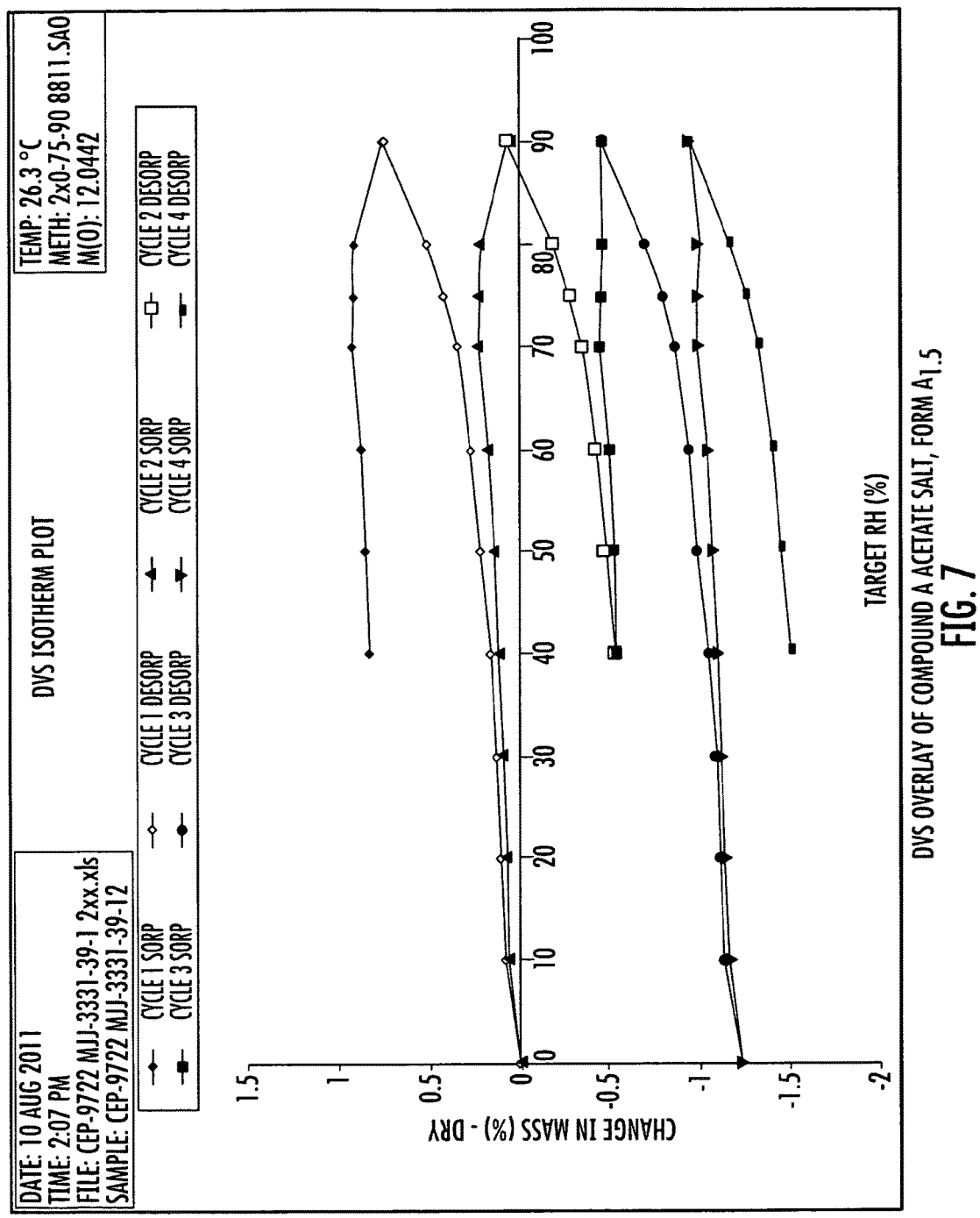
FIG. 7 shows a DVS Overlay of Compound A Acetate Salt, Form $A_{1.5}$.

The DVS plot in FIG. 7 indicates that the sample appears to be saturated from the onset. There is a steady weight loss during the drying curves with no equilibration reached. The sample was dried at 0% RH for 4 hours for each cycle. There were 4 cycles run, showing a continuing weight loss. The experiment was repeated on another DVS unit and showed similar results.

$^1$H-NMR Spectroscopy

The $^1$H-NMR spectrum showed all of the peaks expected for Compound A. The peak at about 7.5 ppm was normalized to the one aromatic proton expected to absorb in this region. The remainder of the peaks associated with Compound A then followed in the proper ratio. For the acetate salt, only one peak is expected at 1.9-2.0 ppm. This peak should integrate for 3 protons. Instead, it showed about 4.5 protons, about 1.5 acetic acid molecules per Compound A molecule.

Stability

The data is given in Table 8 for the aging of the acetate salt, Form $A_{1.5}$, at 40° C. and 75% RH. The XRPD, changes throughout the 28 day test period. The TGA and Compound A Assay values are probably reflecting loss of acetic acid as seen in the thermal and XRPD work cited above. DSC, HPLC Purity and Compound B assay are relatively constant during the study. A monoacetate salt should assay as 87.5% Compound A. A diacetate salt should Assay as 77.7% Compound A. The values in Table 8, suggest that the salt is changing composition as it aged. The $^1$H-NMR measured 1.5 molecules of acetic acid per molecule of Compound A. The XRPD pattern showed peaks for a hydrate Compound A Free Base, Form $H_d$. Possibly as the sample aged the excess acetic acid volatilized. The volatility of acetic acid and the changing XRPD pattern suggest that another candidate be chosen.

TABLE 8

Stability at 40° C. and 75% RH of the Acetate Salt, Form $A_{1.5}$

| Day | XRPD | DSC, ° C. | TGA, % | COM-POUND A Assay, % | COM-POUND B Assay, % | HPLC Purity, % |
|---|---|---|---|---|---|---|
| 0 | $A_{1.5}$ | 54.7, 180.3 Split Peak | 21.5 | 78.1 | 0.2 | 99.7 |
| 7 | Shows hydrate forming | 117.4° 179.9 | 20.0 | 70.2 | 0.1 | 99.6 |
| 14 | Shows hydrate forming | 132.6, 181.5 | 16.1 | 84.2 | 0.2 | 99.5 |
| 28 | Shows hydrate, $H_d$ forming | 126.4, 163.6, 197.9 | 9.6 | 90.9 | 0.3 | 99.6 |

Optical Microscopy

Figure 8:
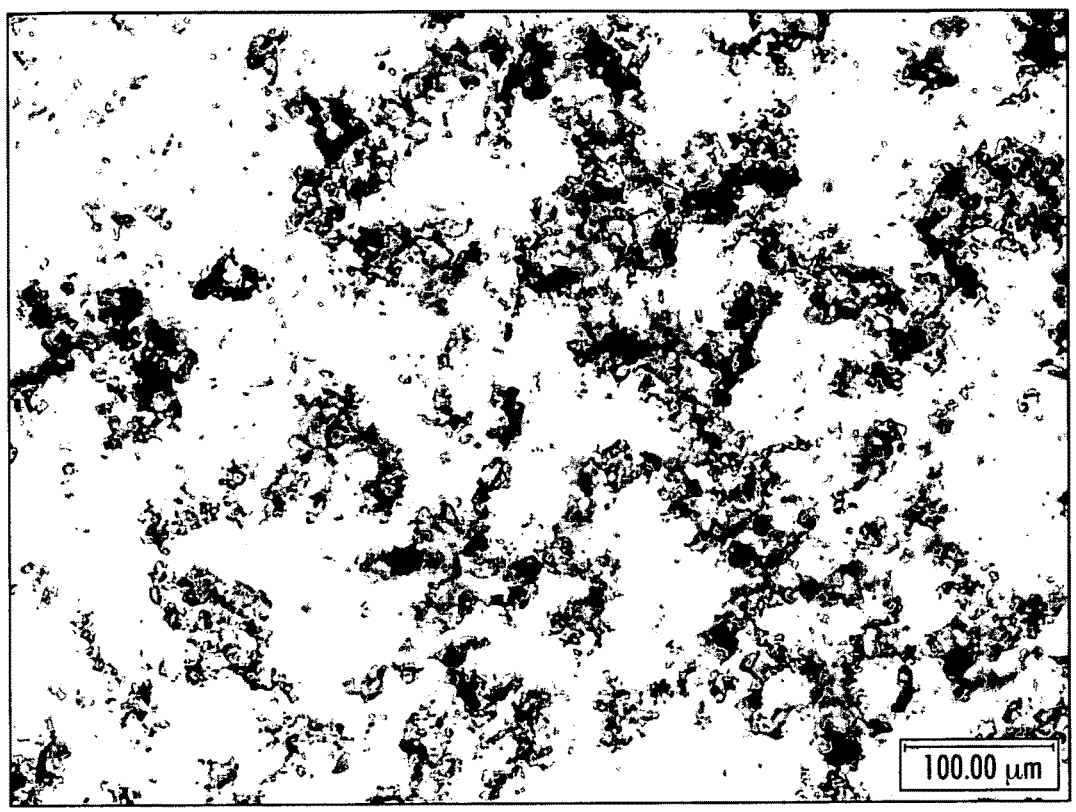
FIG. 8 shows a photomicrograph of Compound A Acetate Salt, Form $A_{1.5}$.

The sample as shown in FIG. 8 presented agglomerates of irregular shaped crystals. The sampled showed birefringence under plane-polarized light.

Compound A, Glycolate Salt Hydrate, Form $A_1$

Preparation

The salt was prepared according to Example 1.

XRPD

Figure 10:
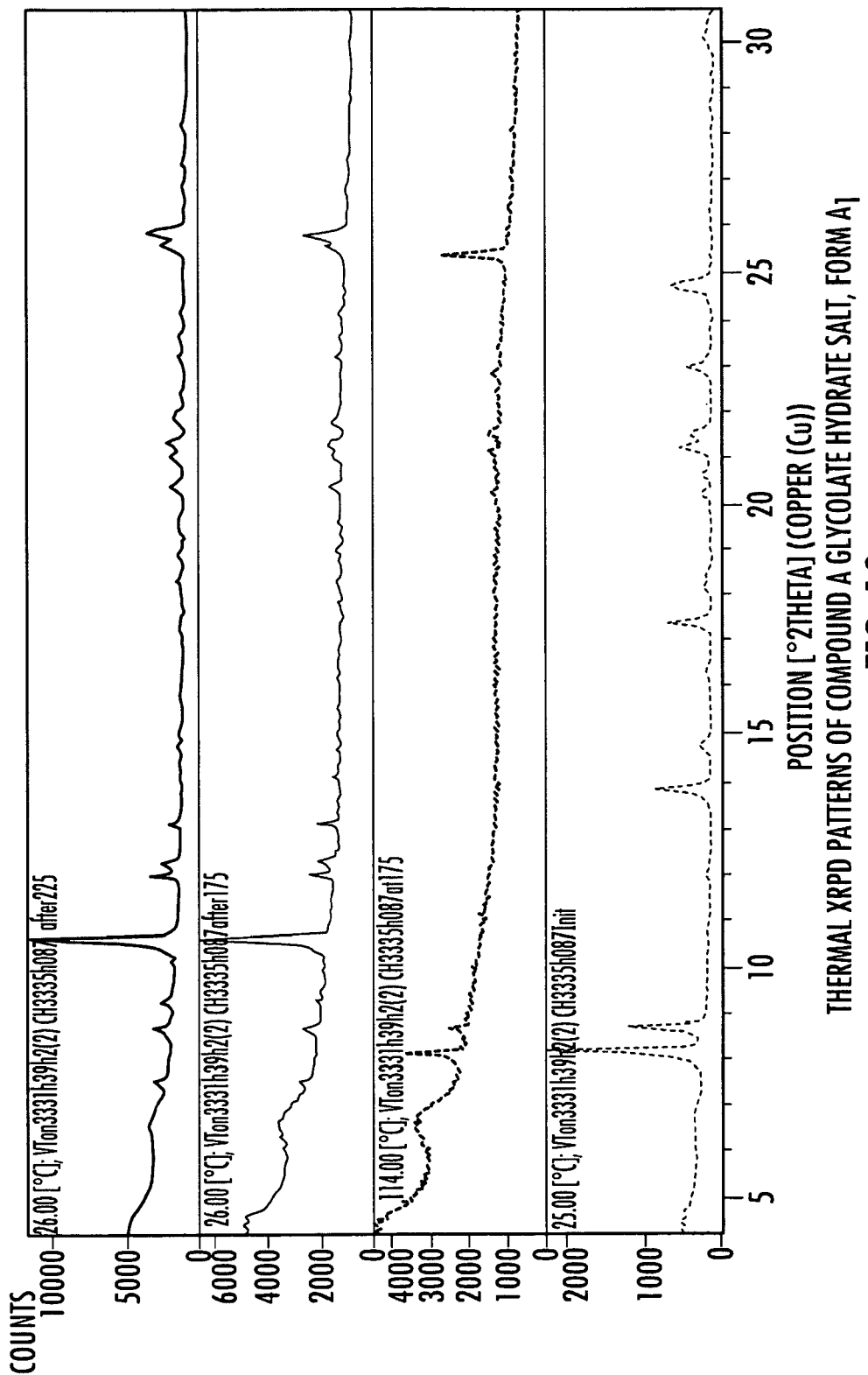
FIG. 10 shows thermal XRPD Patterns of Compound A Glycolate Salt Hydrate, Form $A_1$.

The X-ray diffraction data for the glycolate hydrate salt, Form $A_1$, is given in FIG. 9 and Table 9. Overlaid scans for variable temperature XRPD measurements are shown in FIG. 10. The initial XRPD pattern compared to glycolate hydrate Form $A_1$. There was no change on exposure to a dry $N_2$ atmosphere. During the one hour slow scan measurement at 175° C., the pattern changed. There is an increase in peak intensities on heating from 175° C. to 225° C. It did not compare to known Compound A freebase patterns. The sample on the plate at the end of the measurements was a dark brown powder which did not have the appearance of passing through a melt. The patterns observed after heating to 175° C. and 225° C. partially compares to Compound B. This is consistent with the DSC which shows changes after 130° C. and a melt at 205° C. Both the VT-XRPD and the DSC were consistent with the loss of glycolic acid and conversion to Compound B.

TABLE 9

XRPD Peaks for the Glycolate Hydrate Salt, Form $A_1$

| Pos. [°2θ] | Position calc. | h | k | l | d-spacing [Å] | Height [cts] | Rel. Int. [%] |
|---|---|---|---|---|---|---|---|
| 8.12 | 8.13 | 0 | 0 | 1 | 10.8850 | 781 | 8.7 |
| 8.24 | 8.25 | 0 | 1 | 0 | 10.7261 | 5010 | 55.9 |
| 8.68 | 8.69 | 0 | 1 | 1 | 10.1821 | 6898 | 77.0 |
| 11.96 | 11.98 | 1 | 1 | 1 | 7.3925 | 501 | 5.6 |
| 13.62 | 13.63 | 1 | 1 | 0 | 6.4987 | 275 | 3.1 |
| 13.90 | 13.91 | 0 | 1 | −1 | 6.3683 | 4729 | 52.8 |
| 14.62 | 14.63 | 1 | 0 | −1 | 6.0549 | 581 | 6.5 |
| 14.68 | 14.70 | 0 | 1 | 2 | 6.0279 | 692 | 7.7 |
| 14.89 | 14.90 | 0 | 2 | 1 | 5.9468 | 456 | 5.1 |
| 16.29 | 16.30 | 0 | 0 | 2 | 5.4374 | 321 | 3.6 |
| 17.42 | 17.44 | 0 | 2 | 2 | 5.0866 | 3502 | 39.1 |
| 17.59 | 17.61 | 1 | 2 | 1 | 5.0367 | 994 | 11.1 |
| 18.20 | 18.22 | 1 | −2 | −1 | 4.8706 | 557 | 6.2 |
| 18.48 | 18.50 | 1 | 2 | 2 | 4.7970 | 927 | 10.3 |
| 18.98 | 18.99 | 2 | 0 | 1 | 4.6728 | 252 | 2.8 |
| 19.84 | 19.85 | 2 | 0 | 0 | 4.4719 | 328 | 3.7 |
| 20.23 | 20.24 | 2 | 1 | 1 | 4.3864 | 1426 | 15.9 |
| 20.58 | 20.59 | 2 | −1 | 0 | 4.3131 | 1969 | 22.0 |
| 21.21 | 21.22 | 2 | −1 | 1 | 4.1864 | 3681 | 41.1 |
| 21.30 | 21.32 | 0 | 1 | −2 | 4.1681 | 1097 | 12.2 |
| 21.44 | 21.46 | 1 | 1 | 3 | 4.1409 | 926 | 10.3 |
| 21.48 | 21.49 | 2 | 0 | 2 | 4.1337 | 2196 | 24.5 |
| 21.54 | 21.56 | 1 | −2 | −2 | 4.1216 | 273 | 3.0 |
| 21.66 | 21.68 | 1 | −2 | 1 | 4.0988 | 240 | 2.7 |
| 22.82 | 22.84 | 0 | 2 | 3 | 3.8938 | 297 | 3.3 |
| 23.04 | 23.06 | 0 | 3 | 2 | 3.8571 | 2250 | 25.1 |
| 23.07 | 23.08 | 2 | −1 | −1 | 3.8523 | 1182 | 13.2 |
| 23.71 | 23.73 | 2 | 0 | −1 | 3.7491 | 239 | 2.7 |
| 24.45 | 24.47 | 2 | 2 | 1 | 3.6373 | 464 | 5.2 |
| 24.73 | 24.75 | 2 | −1 | 2 | 3.5969 | 8960 | 100.0 |
| 25.95 | 25.96 | 1 | −3 | −2 | 3.4310 | 312 | 3.5 |
| 26.07 | 26.09 | 2 | −2 | 1 | 3.4148 | 209 | 2.3 |
| 26.27 | 26.28 | 0 | 3 | 3 | 3.3900 | 267 | 3.0 |
| 26.41 | 26.43 | 1 | 3 | 3 | 3.3716 | 308 | 3.4 |
| 27.08 | 27.09 | 2 | 1 | −1 | 3.2907 | 249 | 2.8 |
| 27.90 | 27.92 | 2 | −1 | −2 | 3.1952 | 271 | 3.0 |
| 27.96 | 27.98 | 1 | 3 | 0 | 3.1881 | 219 | 2.4 |
| 28.53 | 28.55 | 1 | 2 | 4 | 3.1260 | 206 | 2.3 |
| 29.96 | 29.97 | 3 | 0 | 0 | 2.9805 | 486 | 5.4 |
| 30.05 | 30.06 | 0 | 4 | 2 | 2.9718 | 224 | 2.5 |
| 30.08 | 30.10 | 2 | −2 | 2 | 2.9682 | 1322 | 14.7 |
| 30.13 | 30.14 | 3 | −1 | 0 | 2.9639 | 546 | 6.1 |
| 30.21 | 30.23 | 2 | −1 | 3 | 2.9557 | 1534 | 17.1 |
| 31.57 | 31.58 | 3 | −1 | 2 | 2.8318 | 240 | 2.7 |
| 32.01 | 32.03 | 3 | 2 | 2 | 2.7934 | 298 | 3.3 |
| 32.76 | 32.77 | 1 | 4 | 1 | 2.7319 | 202 | 2.3 |
| 33.11 | 33.12 | 3 | 2 | 1 | 2.7038 | 276 | 3.1 |
| 33.51 | 33.53 | 3 | 0 | −1 | 2.6721 | 371 | 4.1 |
| 34.01 | 34.02 | 2 | −2 | −3 | 2.6343 | 249 | 2.8 |
| 37.51 | 37.52 | 0 | 1 | −4 | 2.3960 | 240 | 2.7 |

*The use of ZBG or glass plates typically introduces a positive sample height displacement and results in small (0.05° to 0.2°) offset in 2θ values. The highest peak (intensity 100%) is set in bold letters.

Single Crystal Structure

Figure 38:
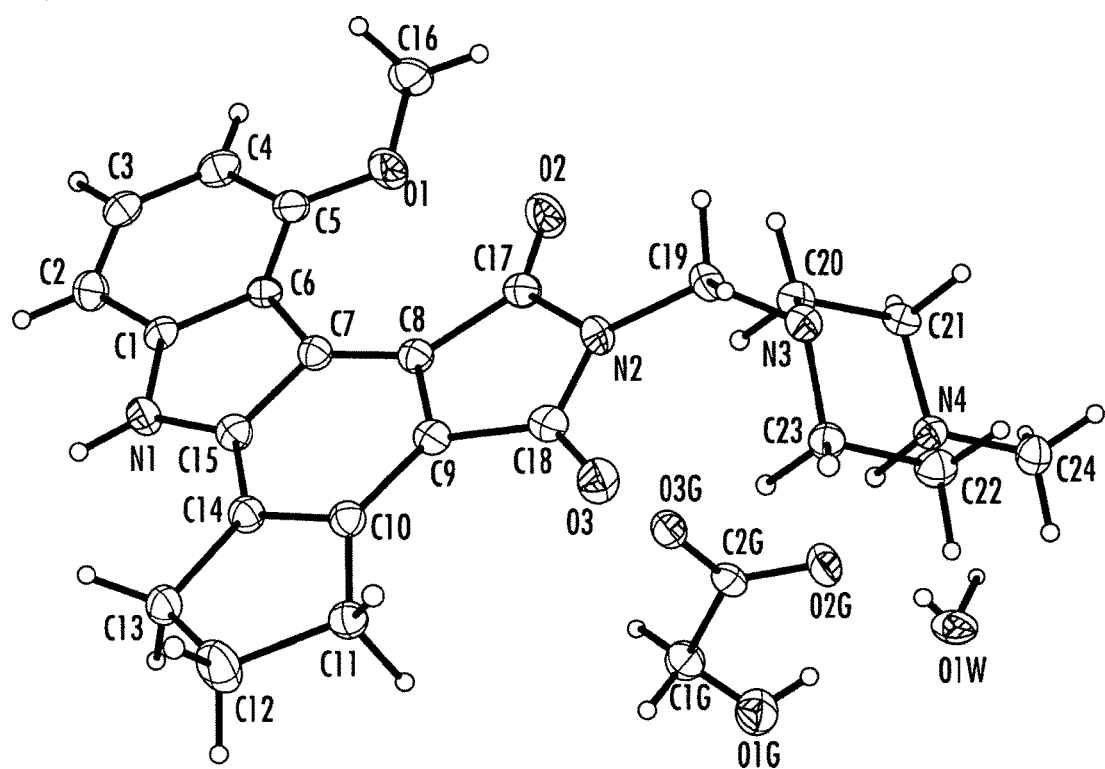
FIG. 38 shows the single crystal structure of Compound A, glycolate hydrate salt.

The single crystal X-ray structure confirmed the presence of the glycolate anion and showed that the piperazine nitrogen atom carries the hydrogen atom. The molecule is shown in FIG. 38. The structure also shows a water molecule which is present at 60% occupancy, that is, the ratio of Compound A to water is 1:0.6. Structural details are given in the below table.

| Variable | Value | |
|---|---|---|
| System | Triclinic | |
| Space Group | P-1 | |
| Temperature (°K) | 90.0(2) | 298(3) |
| a, Å | 9.3613(2) | 9.3957(5) |
| b, Å | 11.8453(2) | 11.9911(8) |
| c, Å | 12.4918(2) | 12.6433(8) |
| α | 64.9920(1) | 65.2827(2) |
| β | 73.2080(1) | 73.0954(1) |
| γ | 88.2480(1) | 88.7671(1) |
| Volume, Å³ | 1195.08(4) | 1229.8 |
| Density, g/ml | 1.404 | |
| λ, Å | 1.54178 | |
| μ, mm⁻¹ | 0.846 | |
| Absorption Correction Method | multi-scan | |
| Absorption Correction Minimum | 0.781 | |
| Absorption Correction Maximum | 0.963 | |
| Reflections (total) | 16031 | |
| Reflections (Unique) | 4237 | |
| Reflections (Observed, >2σ) | 3388 | |
| $R_{merge}$ (internal agreement) | 0.043 | |
| R | 0.0409 | |
| wR | 0.1043 | |
| Minimum Residual Density, e⁻/mm³ | 0.31(5) | |
| Maximum Residual Density, e⁻/mm³ | −0.20(5) | |

Fractional coordinates and isotropic displacement parameters for nonhydrogen atoms of Compound A glycolate hydrate are below.

| Atom | x/a | y/b | z/c | Ueq or Uiso |
|---|---|---|---|---|
| N(1) | −257(2) | −899(1) | 12193(1) | 20(1) |
| N(2) | 5139(2) | 694(1) | 7829(1) | 20(1) |
| N(3) | 6756(2) | 2109(1) | 5718(1) | 19(1) |
| N(4) | 6028(2) | 3909(1) | 3603(1) | 20(1) |
| O(1) | 3205(2) | 2569(1) | 10538(1) | 28(1) |
| O(2) | 4938(2) | 2063(1) | 8709(1) | 29(1) |
| O(3) | 4772(1) | −997(1) | 7440(1) | 24(1) |
| C(1) | 125(2) | 99(2) | 12375(2) | 19(1) |
| C(2) | −591(2) | 359(2) | 13379(2) | 24(1) |
| C(3) | 17(2) | 1385(2) | 13408(2) | 26(1) |
| C(4) | 1276(2) | 2140(2) | 12470(2) | 25(1) |
| C(5) | 1979(2) | 1871(2) | 11474(2) | 21(1) |
| C(6) | 1426(2) | 814(2) | 11409(2) | 18(1) |
| C(7) | 1877(2) | 171(2) | 10607(2) | 18(1) |
| C(8) | 3033(2) | 251(2) | 9554(2) | 18(1) |
| C(9) | 3028(2) | −663(2) | 9123(2) | 18(1) |
| C(10) | 1928(2) | −1682(2) | 9680(2) | 18(1) |
| C(11) | 1733(2) | −2727(2) | 9343(2) | 21(1) |
| C(12) | 438(2) | −3632(2) | 10444(2) | 32(1) |
| C(13) | −315(2) | −2918(2) | 11209(2) | 22(1) |
| C(14) | 786(2) | −1790(2) | 10718(2) | 18(1) |
| C(15) | 769(2) | −890(2) | 11162(2) | 18(1) |
| C(16) | 3936(2) | 3508(2) | 10681(2) | 29(1) |
| C(17) | 4427(2) | 1141(2) | 8708(2) | 20(1) |
| C(18) | 4362(2) | −404(2) | 8046(2) | 19(1) |
| C(19) | 6654(2) | 1170(2) | 6943(2) | 20(1) |
| C(20) | 6273(2) | 3305(2) | 5683(2) | 19(1) |
| C(21) | 6719(2) | 4290(2) | 4353(2) | 20(1) |
| C(22) | 6426(2) | 2644(2) | 3709(2) | 24(1) |
| C(23) | 6001(2) | 1698(2) | 5052(2) | 21(1) |
| C(24) | 6476(2) | 4852(2) | 2287(2) | 25(1) |
| C(1G) | 539(2) | 3469(2) | 4989(2) | 28(1) |
| O(1G) | 335(2) | 4218(1) | 3828(1) | 36(1) |
| C(2G) | 2165(2) | 3395(2) | 4961(2) | 22(1) |
| O(2G) | 3132(1) | 4059(1) | 3938(1) | 28(1) |
| O(3G) | 2455(1) | 2720(1) | 5939(1) | 26(1) |
| O(1W) | 2887(3) | 5938(2) | 1816(2) | 33(1) |

Fractional coordinates and isotropic displacement parameters for hydrogen atoms of Compound A glycolate hydrate are below.

| Atom | x/a | y/b | z/c | Ueq or Uiso |
|---|---|---|---|---|
| H(1N) | −1000(20) | −1530(20) | 12750(20) | 24 |
| H(4N) | 4940(30) | 3842(19) | 3953(19) | 23 |
| H(2) | −1457 | −148 | 14013 | 29 |
| H(3) | −433 | 1583 | 14085 | 31 |
| H(4) | 1659 | 2849 | 12512 | 30 |
| H(11A) | 2661 | −3146 | 9246 | 26 |
| H(11B) | 1469 | −2413 | 8561 | 26 |
| H(12A) | 830 | −4388 | 10960 | 38 |
| H(12B) | −296 | −3897 | 10139 | 38 |
| H(13A) | −1292 | −2670 | 11078 | 26 |
| H(13B) | −472 | −3436 | 12105 | 26 |
| H(16A) | 3290 | 4181 | 10650 | 44 |
| H(16B) | 4885 | 3850 | 10010 | 44 |
| H(16C) | 4137 | 3140 | 11482 | 44 |
| H(19A) | 7229 | 1522 | 7305 | 24 |
| H(19B) | 7157 | 450 | 6862 | 24 |
| H(20A) | 6749 | 3560 | 6170 | 23 |
| H(20B) | 5171 | 3219 | 6054 | 23 |
| H(21A) | 6384 | 5100 | 4325 | 24 |
| H(21B) | 7825 | 4402 | 3996 | 24 |
| H(22A) | 7518 | 2687 | 3319 | 28 |
| H(22B) | 5895 | 2376 | 3262 | 28 |
| H(23A) | 4900 | 1613 | 5432 | 25 |
| H(23B) | 6297 | 871 | 5108 | 25 |
| H(24A) | 6170 | 5666 | 2242 | 38 |
| H(24B) | 5986 | 4590 | 1822 | 38 |
| H(24C) | 7567 | 4923 | 1929 | 38 |
| H(1G1) | 58 | 2611 | 5299 | 33 |
| H(1G2) | 21 | 3808 | 5583 | 33 |
| H(1G) | 1112 | 4714 | 3360 | 53 |
| H(1W) | 3200(50) | 5350(40) | 2430(40) | 42(11) |
| H(2W) | 3340(60) | 6690(40) | 1640(40) | 70(16) |

Thermal Analysis

Figure 11:
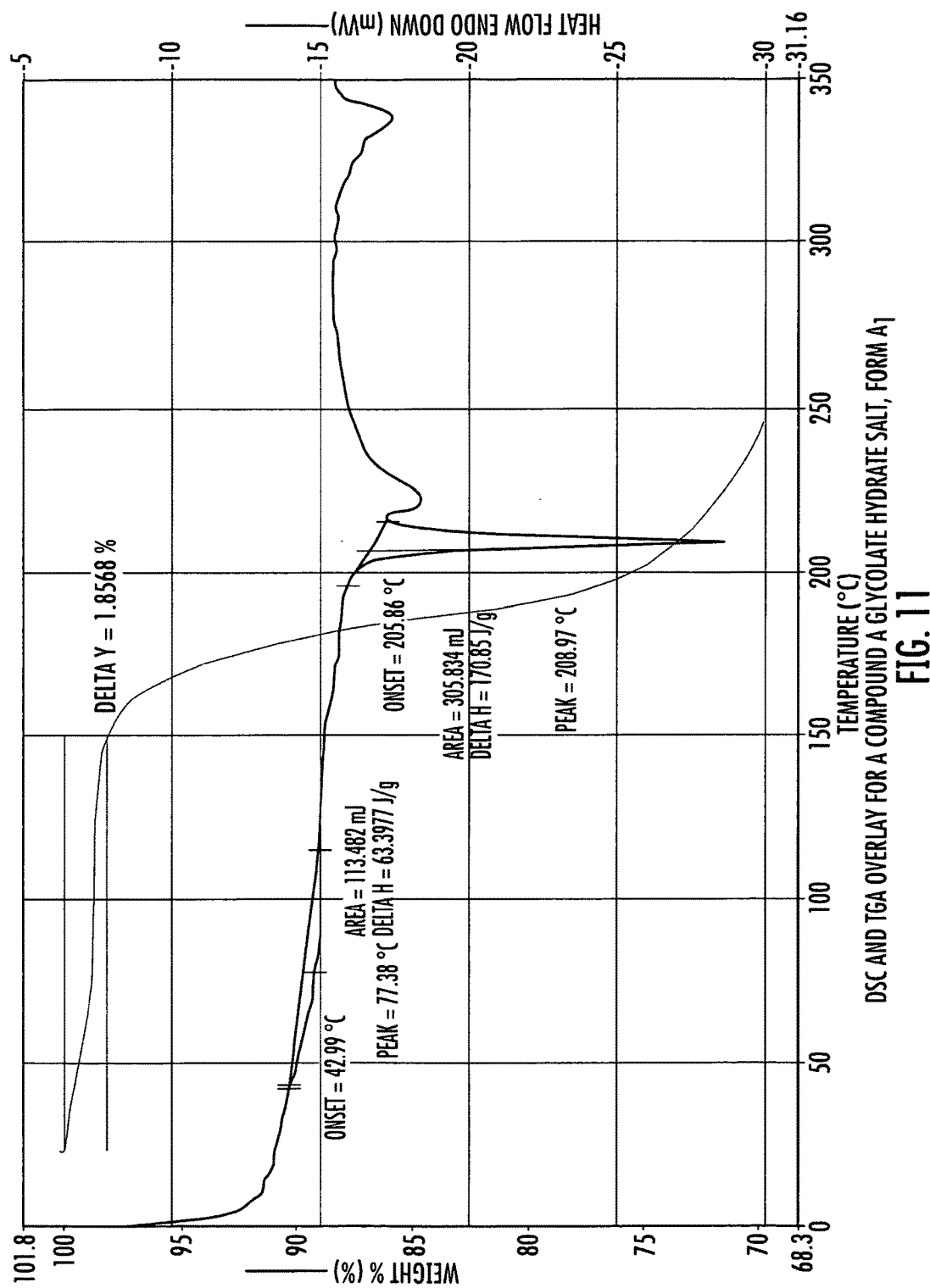
FIG. 11 shows a DSC and TGA Overlay of Compound A Glycolate Salt Hydrate, Form $A_1$.

The DSC curve of the glycolate hydrate salt, Form $A_1$, shows the presence of two different endothermic peaks; one at 77.4° C. having a $\Delta H_{Fus}$ of 63.4 J/g and a second peak at 209.0° C. and a $\Delta H_{Fus}$ of 170.9 J/g (FIG. 11). The glycolate hydrate salt had a weight loss of 1.9% between 25 and 150° C.

Water Sorption

Figure 12:
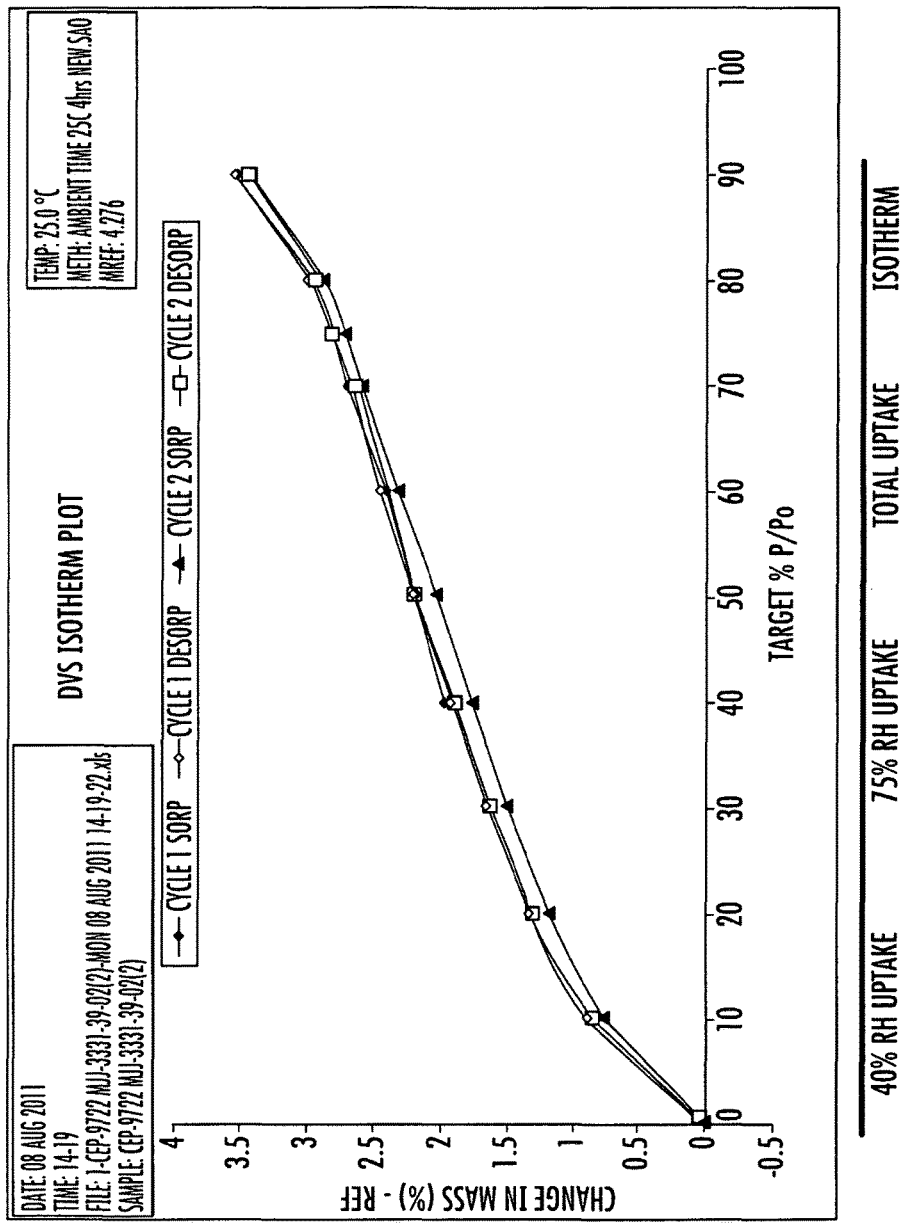
FIG. 12 shows a DVS Overlay of Compound A Glycolate Salt Hydrate, Form $A_1$.

The DVS plot in FIG. 12 indicated that there was surface adsorption with limited bulk absorption throughout the entire RH range. The total uptake in moisture at 90% RH is ~3.5%.

¹H-NMR Spectroscopy

The spectrum gives all of the peaks necessary for Compound A. After normalization of the integration to one proton in the aromatic region at about 7.5 ppm for Compound A, there is a two proton singlet at about 3.9 ppm for the two protons associated with the methylene group of glycolic acid. This indicated a 1:1 mole ratio of Compound A to glycolic acid in the salt.

Stability

The data given in Table 10 indicate that this salt is fairly stable to the test conditions. A modest increase in Compound B is noted after 28 days. A monoglycolate salt, as the ¹H-NMR indicated, should have a Compound A Assay of 84.5% Compound A. Increasing loss in TGA suggests increasing water content, for example, 3.5% loss would be expected for a water to Compound A ratio of 1:1.

TABLE 10

Stability at 40° C. and 75% RH of Glycolate Salt Hydrate, Form $A_1$

| Day | XRPD | DSC, ° C. | TGA, % | COMPOUND A Assay, % | COMPOUND B Assay, % | HPLC Purity, % |
|---|---|---|---|---|---|---|
| 0 | A1 | 69.7, 207.9 | 2.1 | 69.9 | 0.1 | 99.8 |
| 7 | No change | 208.3 | 2.3 | 68.4 | 0.1 | 99.6 |
| 14 | No change | 68.8, 207.3 | 2.6 | 73.2 | 0.2 | 99.7 |
| 28 | No change | 207.4 | 3.5 | 66.8 | 0.6 | 99.5 |

Optical Microscopy

Figure 13:
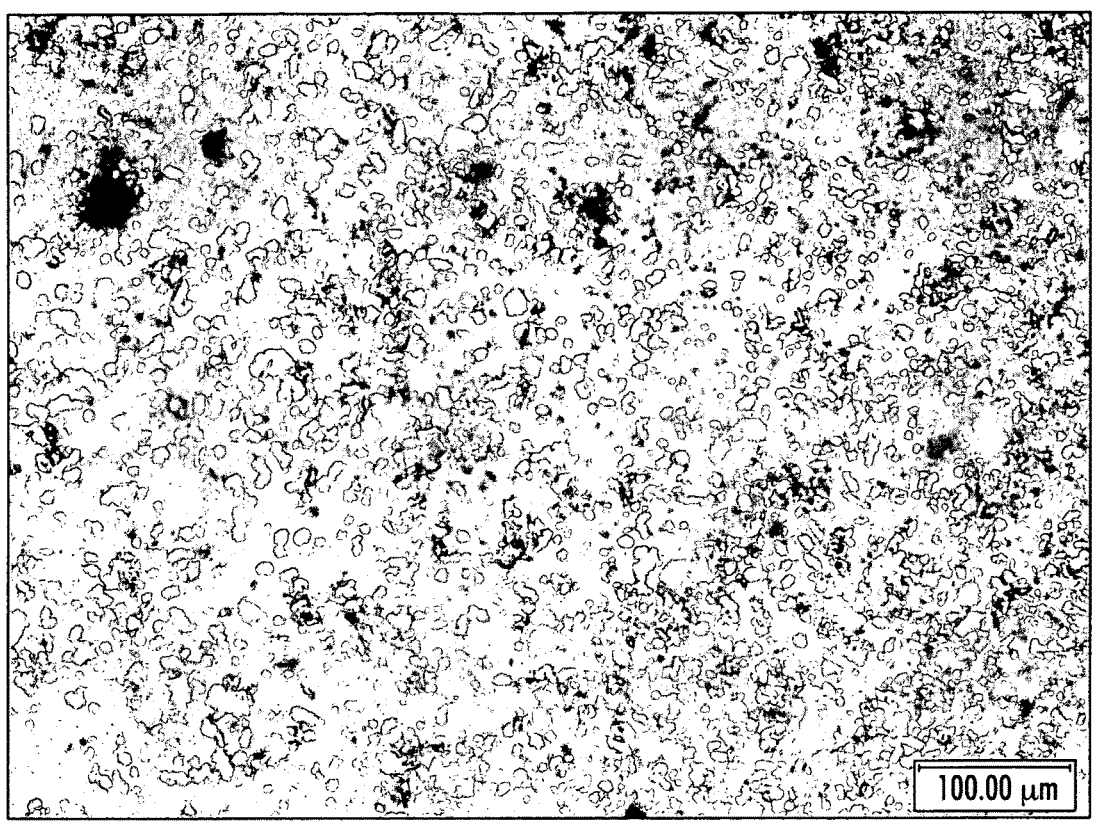
FIG. 13 shows a photomicrograph of Compound A Glycolate Salt Hydrate, Form $A_1$.

In FIG. 13, the sample presented individual and agglomerates of crystals. The sample showed birefringence under plane polarized light.

Compound A, L-Malate Salt, Form $A_1$

Preparation

The salt was prepared according to Example 1.

XRPD

Figure 15:
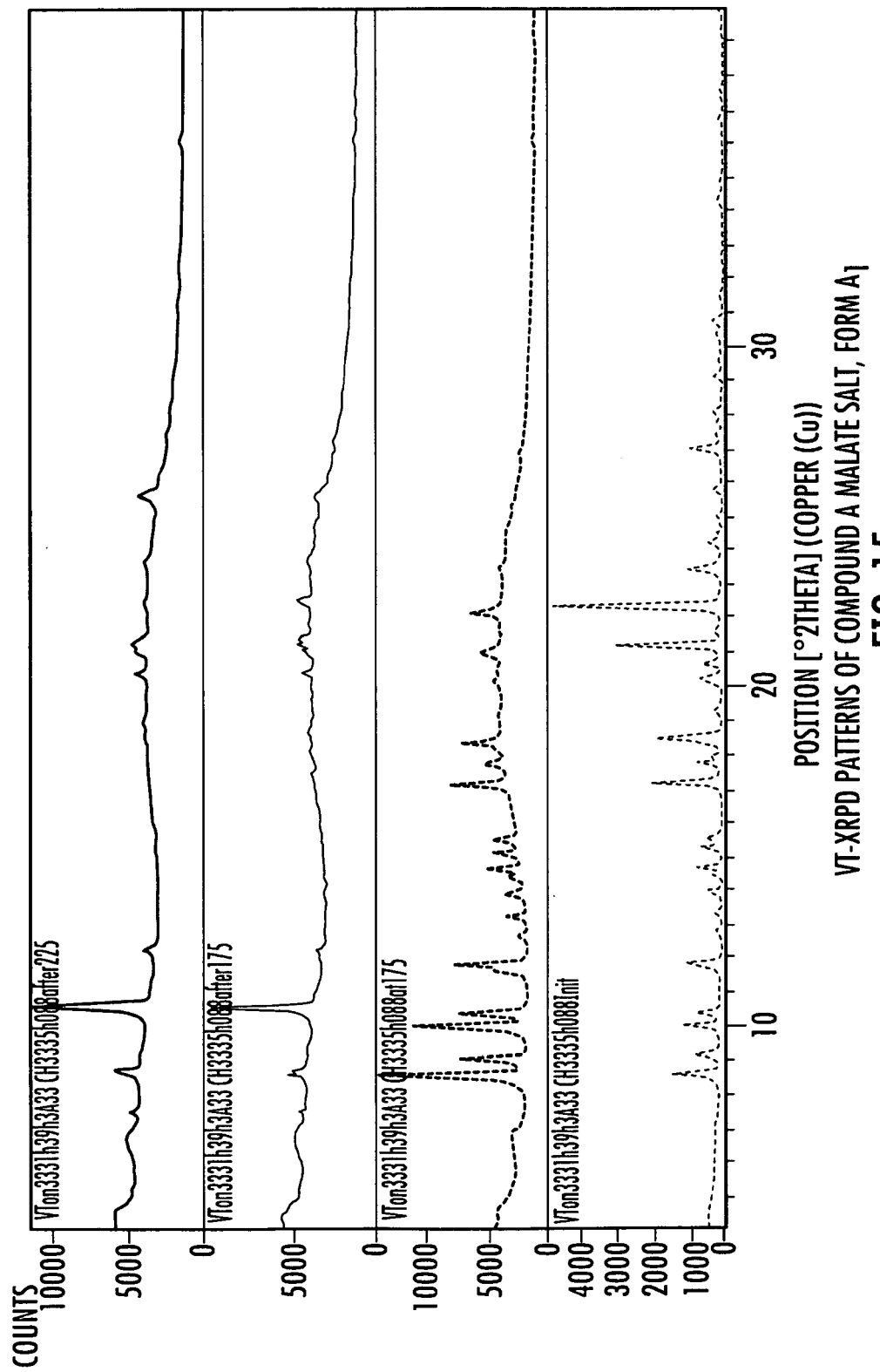
FIG. 15 shows VT-XRPD Patterns of Compound A Malate Salt, Form $A_1$.

The X-ray diffraction data for the malate salt, Form $A_1$, is given in FIG. 14 and Table 11. Overlaid slow scans for a VT-XRPD study are shown in FIG. 15.

The initial XRPD pattern is as expected. There is no change in form on exposure to a dry N2 atmosphere (FIG. 15). There is a change when the sample is held at 175° C. for an hour. The fast scan measured when 175° C. was first reached compares to the starting pattern. The crystallinity is almost completely gone in the fast scan measured after 175° C. The slow scan pattern observed for this sample after heating to 175° C. and cooling to 25° C. partially compares to the pattern for Compound B. This observation is consistent with thermal decomposition to Compound B.

TABLE 11

XRPD Peaks for Malate Salt, Form $A_1$

| No. | Pos. [2θ°]* | d-spacing [Å] | Rel. Int.[%] |
|---|---|---|---|
| 1 | 8.60 | 10.269 | 51 |
| 2 | 9.18 | 9.631 | 25 |
| 3 | 10.06 | 8.789 | 36 |
| 4 | 10.40 | 8.496 | 25 |
| 5 | 11.74 | 7.529 | 14 |
| 6 | 11.87 | 7.450 | 27 |
| 7 | 12.85 | 6.885 | 3 |
| 8 | 13.33 | 6.635 | 6 |
| 9 | 13.97 | 6.334 | 5 |
| 10 | 14.46 | 6.120 | 6 |
| 11 | 14.70 | 6.021 | 18 |
| 12 | 15.27 | 5.797 | 12 |
| 13 | 15.56 | 5.690 | 9 |
| 14 | 17.19 | 5.156 | 47 |
| 15 | 17.76 | 4.991 | 17 |
| 16 | 17.98 | 4.930 | 5 |
| 17 | 18.54 | 4.781 | 28 |
| 18 | 19.29 | 4.597 | 5 |
| 19 | 20.27 | 4.376 | 14 |
| 20 | 20.65 | 4.297 | 9 |
| 21 | 21.22 | 4.184 | 53 |
| 22 | 21.59 | 4.112 | 3 |
| 23 | 22.36 | 3.972 | 100 |
| 24 | 23.45 | 3.791 | 17 |
| 25 | 24.08 | 3.692 | 2 |
| 26 | 24.27 | 3.664 | 10 |
| 27 | 24.52 | 3.627 | 3 |
| 28 | 24.99 | 3.560 | 2 |
| 29 | 25.76 | 3.455 | 3 |
| 30 | 25.87 | 3.442 | 3 |
| 31 | 26.99 | 3.301 | 15 |
| 32 | 27.38 | 3.254 | 3 |
| 33 | 27.79 | 3.208 | 3 |
| 34 | 27.96 | 3.188 | 4 |
| 35 | 28.12 | 3.171 | 2 |
| 36 | 29.11 | 3.066 | 4 |
| 37 | 29.60 | 3.016 | 2 |
| 38 | 30.22 | 2.955 | 2 |
| 39 | 30.42 | 2.936 | 3 |
| 40 | 30.75 | 2.905 | 5 |

*The use of ZBG or glass plates typically introduces a positive sample height displacement and results in small (0.05° to 0.2°) offset in 2θ values. The highest peak (intensity 100%) is set in bold letters.

Thermal Analysis

Figure 16:
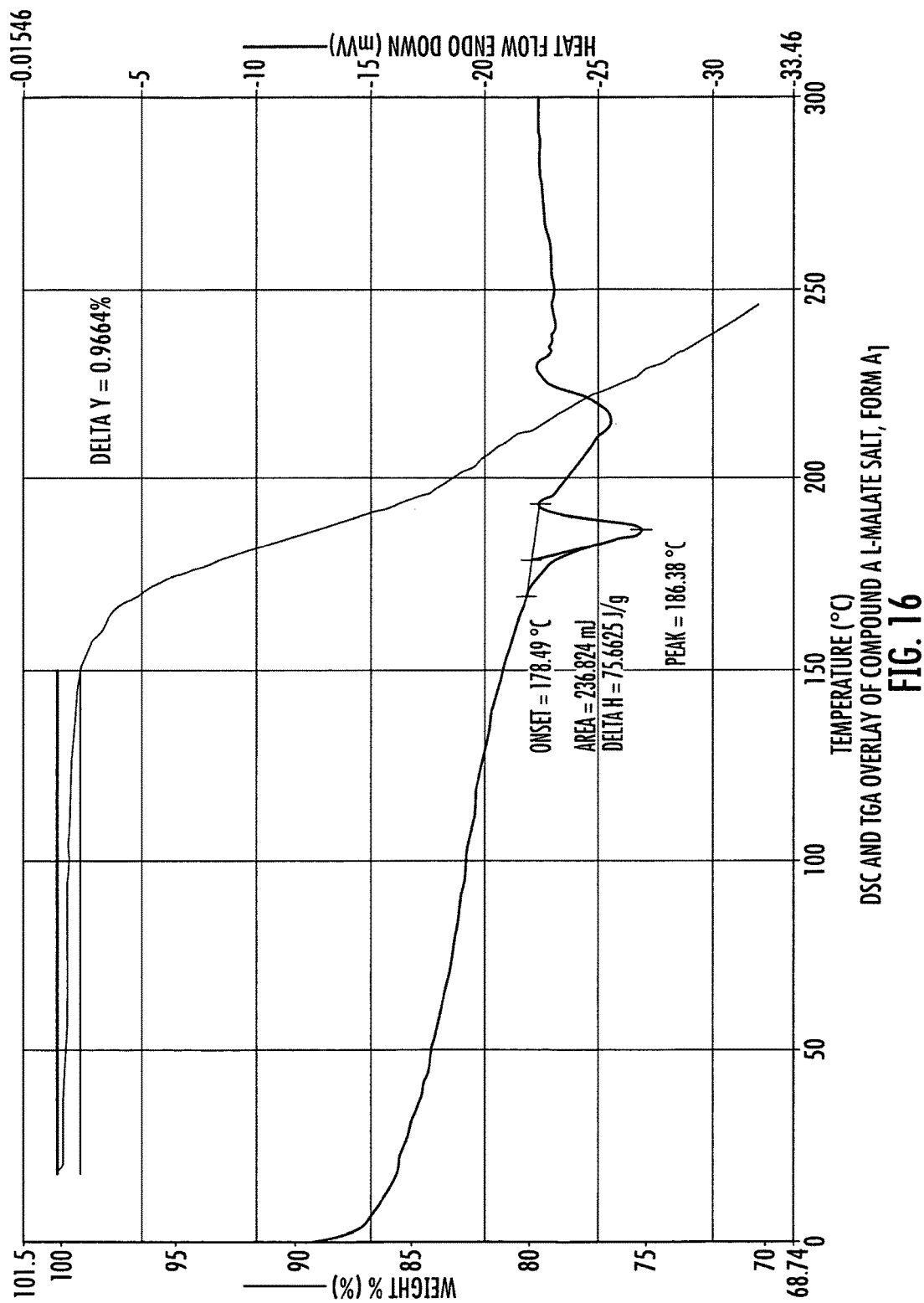
FIG. 16 shows a DSC and TGA Overlay of Compound A L-Malate Salt, Form $A_1$.

The DSC curve of the malate salt, Form $A_1$ shows the presence of one endothermic peak; at 186.4° C. having a $\Delta H_{Fus}$ of 75.7 J/g (FIG. 16). The malate salt had a weight loss of 1.0% between 25 and 150° C.

Water Sorption

The DVS plot in (FIG. 17) indicated there was very little water absorption during the first cycle from 40% RH to 70% RH. Only surface adsorption is occurring. At 80% RH is an increase in water uptake. The large hysteresis gap is due to bulk absorption. The total uptake is ~2%. The isotherm is irreversible.

$^1$H-NMR Spectroscopy

All of the peaks expected for Compound A are present. After normalization of the one aromatic proton at 7.5 ppm, there is a one proton triplet at about 4.05 ppm that is consistent with L-malic acid. This established the 1:1 stoichiometry for the Compound A L-malic acid salt in Form $A_1$.

Stability

The data in Table 12 show that the L-malate salt is stable to the test conditions with a constant XRPD, DSC, TGA and HPLC Purity values (MJJ3331-49). An increase in Compound B is observed after 28 days. As with the glycolate hydrate salt, the L-malate Assay value for Compound A is lower than the 75.8% value expected.

TABLE 12

Stability at 40° C. and 75% RH of the L-Malate Salt, Form $A_1$

| Day | XRPD | DSC | TGA | COMPOUND A Assay | COMPOUND B Assay | HPLC Purity |
|---|---|---|---|---|---|---|
| 0 | $A_1$ | 193.0° C. | 0.1% | 69.9% | 0.2% | 99.5% |
| 7 | No change | 192.0° C. | 0.2% | 71.8% | 0.4% | 99.3% |
| 14 | No change | 191.4° C. | 0.8% | 72.0% | 0.5% | 98.8% |
| 28 | No change | 191.1° C. | 0.3% | 71.7% | 0.8% | 98.4% |

Optical Microscopy

Figure 18:
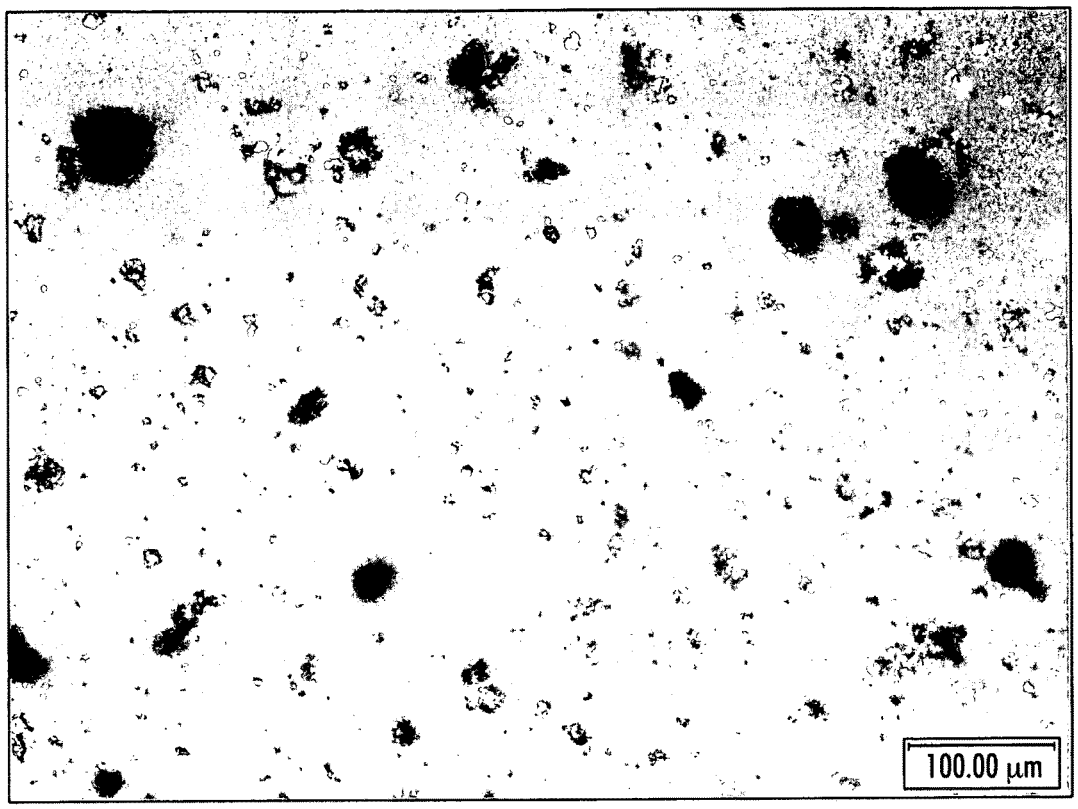
FIG. 18 shows a photomicrograph of Compound A L-Malate Salt, Form $A_1$.

In FIG. 18, the sample showed individual crystals and agglomerates of irregular shaped crystals. The sample showed birefringence under plane polarized light.

Compound A, L-Malate Salt, Form $A_{1.5}$

Preparation

The salt was prepared according to Example 2.

XRPD

The X-ray diffraction data for the malate salt, Form $A_{1.5}$, is given in FIG. 19 and Table 13.

TABLE 13

XRPD Peaks for Malate Salt, Form A$_{1.5}$

| No. | Pos. [2θ°]* | d-spacing [Å] | Rel. Int.[%] |
|---|---|---|---|
| 1 | 5.53 | 15.978 | 63 |
| 2 | 6.80 | 12.985 | 53 |
| 3 | 7.97 | 11.085 | 26 |
| 4 | 8.43 | 10.478 | 100 |
| 5 | 8.76 | 10.084 | 35 |
| 6 | 9.23 | 9.577 | 23 |
| 7 | 11.79 | 7.500 | 28 |
| 8 | 12.44 | 7.108 | 10 |
| 9 | 12.78 | 6.923 | 17 |
| 10 | 13.05 | 6.778 | 17 |
| 11 | 13.64 | 6.489 | 15 |
| 12 | 13.92 | 6.355 | 11 |
| 13 | 14.44 | 6.131 | 61 |
| 14 | 15.99 | 5.538 | 44 |
| 15 | 16.66 | 5.316 | 72 |
| 16 | 17.12 | 5.175 | 7 |
| 17 | 18.12 | 4.891 | 31 |
| 18 | 18.46 | 4.802 | 40 |
| 19 | 18.79 | 4.720 | 7 |
| 20 | 19.44 | 4.562 | 17 |
| 21 | 20.16 | 4.401 | 16 |
| 22 | 20.53 | 4.322 | 15 |
| 23 | 21.13 | 4.201 | 20 |
| 24 | 21.37 | 4.154 | 11 |
| 25 | 21.86 | 4.063 | 20 |
| 26 | 22.84 | 3.890 | 10 |
| 27 | 23.14 | 3.841 | 24 |
| 28 | 23.63 | 3.762 | 14 |
| 29 | 24.04 | 3.698 | 10 |
| 30 | 24.60 | 3.615 | 29 |
| 31 | 25.16 | 3.536 | 13 |
| 32 | 25.66 | 3.469 | 9 |
| 33 | 28.20 | 3.162 | 7 |
| 34 | 29.00 | 3.076 | 3 |
| 35 | 30.05 | 2.971 | 5 |
| 36 | 30.43 | 2.936 | 6 |
| 37 | 32.25 | 2.774 | 2 |
| 38 | 33.11 | 2.704 | 2 |
| 39 | 36.66 | 2.449 | 3 |
| 40 | 39.38 | 2.286 | 3 |

*The use of ZBG or glass plates typically introduces a positive sample height displacement and results in small (0.05° to 0.2°) offset in 2θ values. The highest peak (intensity 100%) is set in bold letters.

Thermal Analysis

Figure 20:
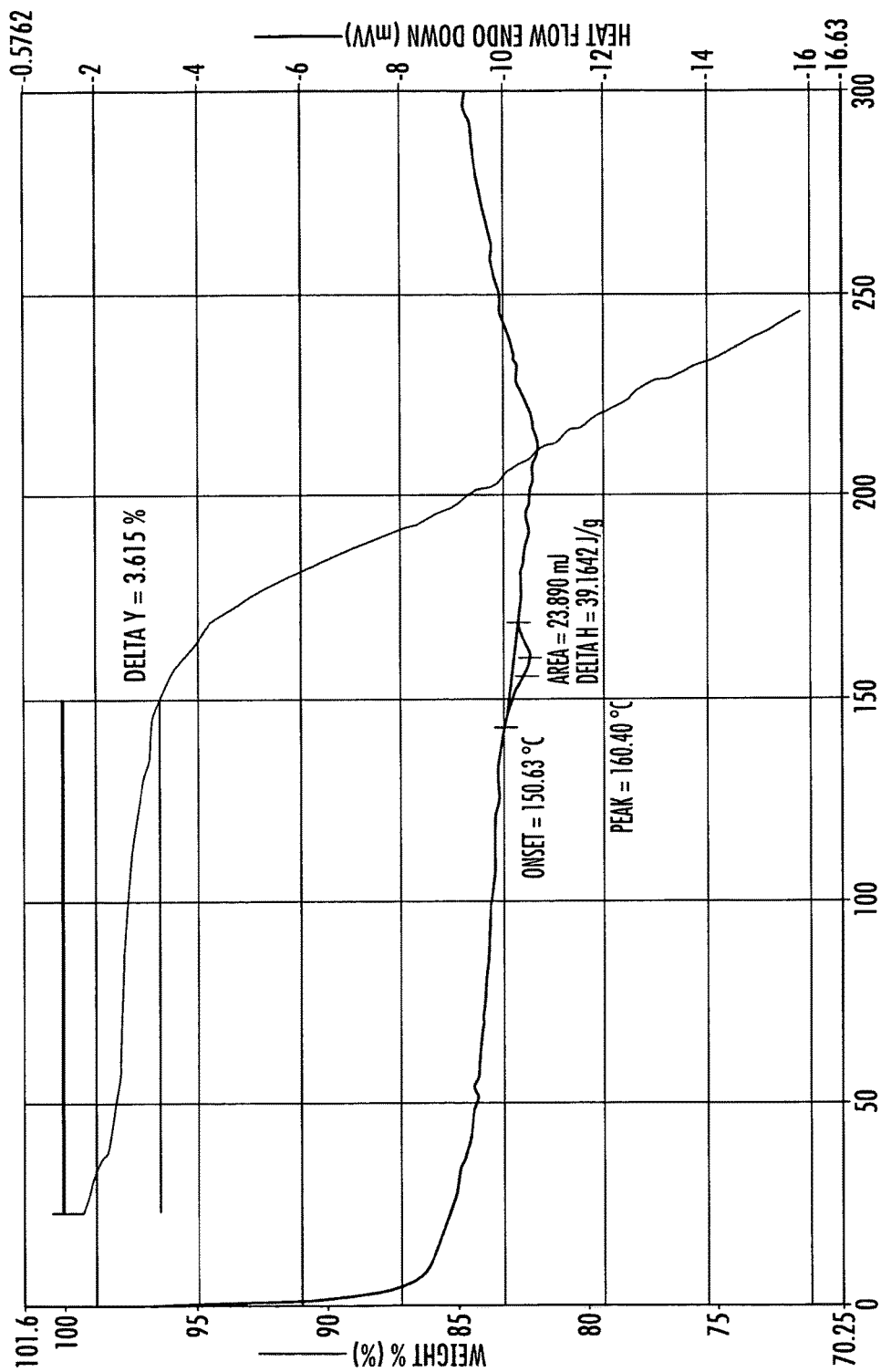
FIG. 20 shows a DSC and TGA Overlay of Compound A L-Malate Salt, Form $A_{1.5}$.

The DSC curve of the L-malate salt, Form A$_{15}$, shows the presence of one endothermic peak; at 160.4° C. having a $\Delta H_{Fus}$ of 39.2 J/g (FIG. 20). The L-malate salt had a weight loss of 3.6% between 25 and 150° C. This Form melts at a much lower temperature and has a larger weight loss than the malate salt, Form A$_1$.

¹H-NMR Spectroscopy

The ¹H-NMR spectrum of the L-malate salt, Form A$_{1.5}$ showed all of the peaks were present for Compound A and the normalized integration showed about 3 moles of L-malic acid for two moles of Compound A. This preparation represented a new form for Compound A L-malate salt.

Compound A, L-Pyroglutamate Salt, Form A$_1$

Preparation

The salt was prepared according to Example 3.

XRPD

The X-ray diffraction data for the L-pyroglutamate salt, Form A$_1$ is given in Table 14 and FIG. 21. The XRPD pattern showed a highly crystalline solid.

Figure 22:
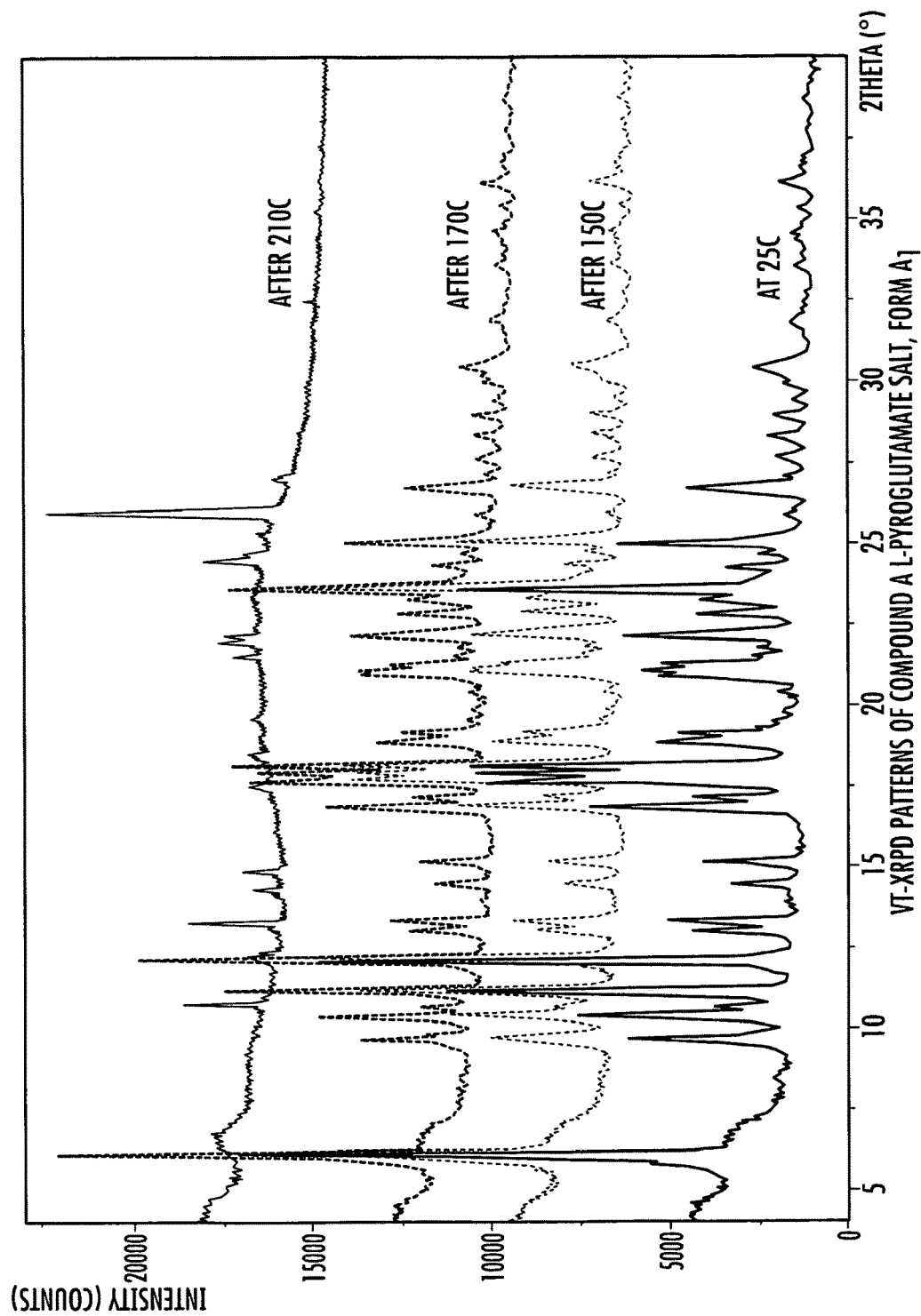
FIG. 22 shows VT-XRPD Patterns of Compound A L-Pyroglutamate Salt, Form $A_1$.

Variable temperature XRPD measurements are shown in FIG. 22. The initial XRPD pattern is as expected. There is no change in form on heating to 175° C. At the end of the experiment a black glass was left on the ZBG plate. Comparison of the expected pattern for Compound B and the sample after heating to 210° C. shows small differences. This suggests conversion of Compound A to Compound B and a possible second component.

TABLE 14

XRPD Peaks for L-Pyroglutamate Salt, Form A$_1$

| No. | Pos. [2θ°]* | d-spacing [Å] | Rel. Int.[%] |
|---|---|---|---|
| 1 | 6.02 | 14.669 | 74 |
| 2 | 9.56 | 9.242 | 43 |
| 3 | 10.31 | 8.573 | 61 |
| 4 | 10.54 | 8.391 | 25 |
| 5 | 11.03 | 8.017 | 96 |
| 6 | 12.01 | 7.364 | 100 |
| 7 | 12.89 | 6.864 | 21 |
| 8 | 13.22 | 6.693 | 33 |
| 9 | 14.32 | 6.180 | 12 |
| 10 | 15.00 | 5.900 | 24 |
| 11 | 16.71 | 5.301 | 36 |
| 12 | 17.02 | 5.206 | 22 |
| 13 | 17.51 | 5.061 | 59 |
| 14 | 17.79 | 4.983 | 68 |
| 15 | 18.02 | 4.919 | 78 |
| 16 | 18.68 | 4.747 | 19 |
| 17 | 18.98 | 4.672 | 29 |
| 18 | 19.37 | 4.578 | 7 |
| 19 | 20.22 | 4.388 | 7 |
| 20 | 20.76 | 4.276 | 35 |
| 21 | 20.98 | 4.231 | 34 |
| 22 | 21.14 | 4.199 | 29 |
| 23 | 21.36 | 4.156 | 9 |
| 24 | 21.67 | 4.097 | 10 |
| 25 | 21.96 | 4.045 | 33 |
| 26 | 22.11 | 4.017 | 23 |
| 27 | 22.70 | 3.914 | 21 |
| 28 | 23.13 | 3.842 | 23 |
| 29 | 23.39 | 3.800 | 84 |
| 30 | 23.51 | 3.781 | 56 |
| 31 | 24.11 | 3.689 | 14 |
| 32 | 24.53 | 3.626 | 8 |
| 33 | 24.84 | 3.582 | 54 |
| 34 | 25.08 | 3.547 | 9 |
| 35 | 26.56 | 3.353 | 33 |
| 36 | 27.57 | 3.232 | 8 |
| 37 | 28.15 | 3.168 | 13 |
| 38 | 28.78 | 3.099 | 9 |
| 39 | 30.22 | 2.955 | 11 |
| 40 | 30.43 | 2.935 | 9 |

*The use of ZBG or glass plates typically introduces a positive sample height displacement and results in small (0.05° to 0.2°) offset in 2θ values. The highest peak (intensity 100%) is set in bold letters.

Thermal Analysis

Figure 23:
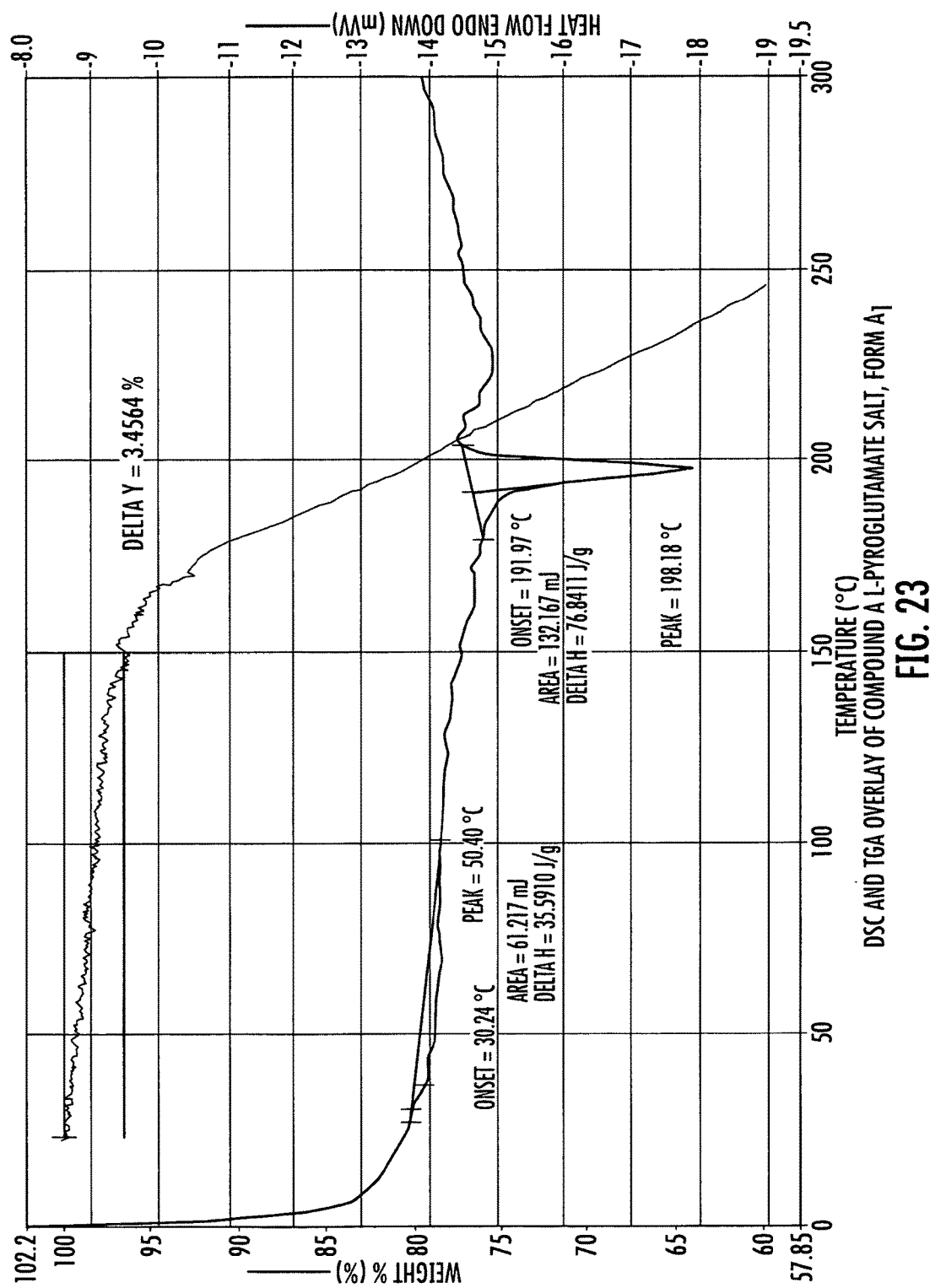
FIG. 23 shows a DSC and TGA Overlay of Compound A L-Pyroglutamate Salt, Form $A_1$.

The DSC curve of the L-pyroglutamate salt, Form A$_1$, shows the presence of two endothermic peaks; at 50.4° C. having a $\Delta H_{Fus}$ of 35.6 J/g and 198.2° C. having a $\Delta H_{Fu}$ of 76.8 J/g (FIG. 23). The pyroglutamate salt had a weight loss of 3.5% between 25 and 150° C.

Water Sorption

In the DVS Plot (FIG. 24) indicated that during the first cycle there is very little water absorption over the RH range of 40-75% (~2%). Only surface adsorption is occurring. At 80% RH there is a massive uptake in moisture. The large hysteresis gap at 50-90% RH is due to bulk absorption with a possible hydrate formation. The total uptake is ~27%.

¹H-NMR Spectroscopy

All of the peaks are present for Compound A. After normalization of the integration for one proton for the aromatic peak in Compound A at about 7.5 ppm, there is an additional one proton singlet at about 7.85 ppm for the hydrogen atom on the amide nitrogen in pyroglutamic acid. In addition, there is an additional one proton multiplet at about 4.05 ppm from the one hydrogen atom attached to the carbon atom adjacent to the carboxylic acid group. This establishes this salt as a mono L-pyroglutamate salt of Compound A.

Stability

This salt was stable over a 28 day test period, except for a slow increase in Compound B content (Table 15).

TABLE 15

Stability at 40° C. and 75% RH of the L-Pyroglutamate Salt, Form $A_1$ (Prepared with Two Equivalents of Acid)

| Day | XRPD | DSC, | TGA, % | COMPOUND A Assay, % | COMPOUND B Assay, % | HPLC Purity, % |
|---|---|---|---|---|---|---|
| 0 | $A_1$ | 198.2 | 0.49 | 65.5 | 0.6 | 98.6 |
| 7 | No change | 199.0 | 0.54 | 71.4 | 0.6 | 98.7 |
| 14 | No change | 198.3 | 0.64 | 60.2 | 0.8 | 98.2 |
| 28 | No change | 198.4 | 0..11 | 64.0 | 1.2 | 97.2 |

Optical Microscopy

Figure 25:
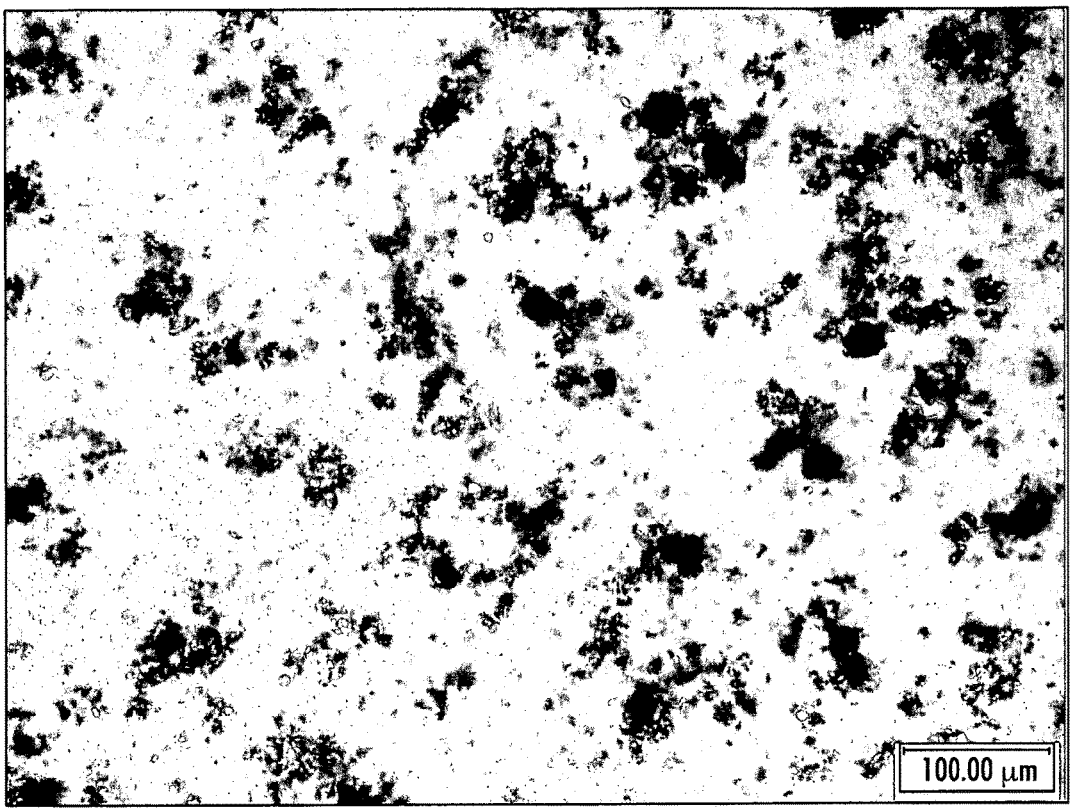
FIG. 25 shows a photomicrograph of Compound A L-Pyroglutamate Salt, Form $A_1$.

The sample presented agglomerates of irregular shaped crystals as shown in FIG. 25. The sample showed birefringence under plane polarized light.

Comparison of Salts

In Table 16, glycolate hydrate Form $A_1$, L-malate Form $A_1$ and the one and two equivalent preparations of L-pyroglutamate Form $A_1$ are compared. The glycolate hydrate salt, Form $A_1$, generated the least amount of Compound B during 40° C. and 75% RH stability testing. The glycolate hydrate exhibited a preference for water absorption since the TGA value increased to 3.5% during stability testing (Table 10).

TABLE 16

Comparison of Compound A Salts

| Property | Glycolate (2 Eq.) | L-malate (2 Eq.) | L-pyroglutamate (2 Eq.) | L-pyroglutamate (1 Eq.) |
|---|---|---|---|---|
| Crystallinity | Form $A_1$ | Form $A_1$ | Form $A_1$ | Form $A_1$ |
| DSC | 69.7, 207.9 | 193.0 | 198.2 | 201.7 |
| TGA | 2.1% | 0.1% | 0.5% | 0.2% |
| DVS | Reversible | Irreversible | Irreversible | Not measured |
| TGA After 40/75: | | | | |
| COMPOUND A Initial | 69.9% | 71.3% | 65.5% | 75.5% |
| COMPOUND B Initial | 0.1% | 0.2% | 0.6% | 0.5% |
| COMPOUND B After 40/75 | 0.6% | 1.2% | 1.2% | 1.3% |
| Est. Water Solubility | >100 mg/mL | >100 mg/mL | >100 mg/mL | >100 mg/mL |
| % Active in Salt | 85% | 76% | 76% | 76% |
| Desiccant Required | Yes | Yes | Yes | Yes |
| Acid Classification | Class 1 | Class 1 | Class 2 | Class 2 |

Compound A, Free Base, Form $C_0$

Preparation

The free base was prepared according to Example 4.

XRPD

Figure 26:
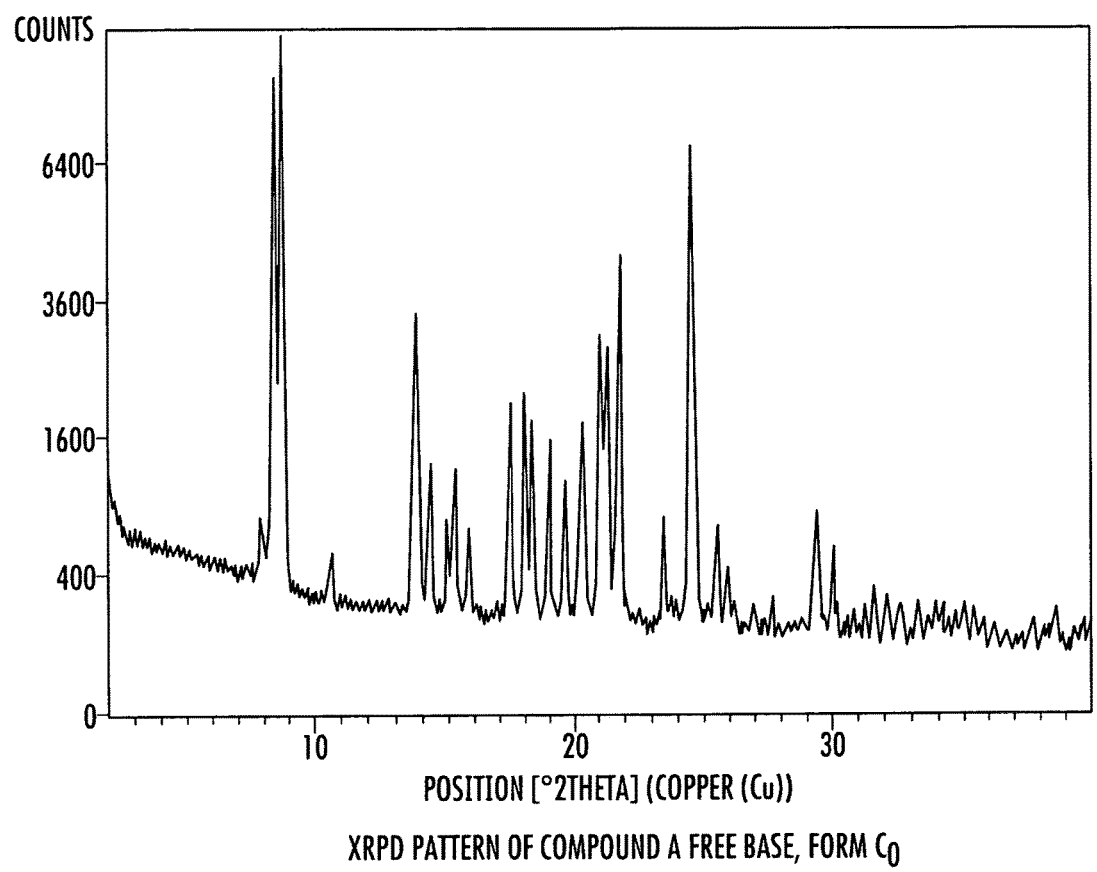
FIG. 26 shows an XRPD Pattern of Compound A Free Base, Form $C_0$.

The X-ray diffraction data for free base, Form $C_0$, is given in FIG. 26 and Table 17. The XRPD pattern showed a crystalline solid.

Variable temperature XRPD measurements are shown in FIG. 27. The initial XRPD pattern compares to the expected pattern for Form $C_0$. There is no change in form on exposure to a dry N2 atmosphere. There is no change in form after heating to 175° C. After heating to 235° C. the XRPD pattern is changed and is similar to, but not the same as, the pattern observed for Compound B. Similar patterns have been seen for other VT samples. There seem to be two components present in this decomposition product.

TABLE 17

XRPD Peaks for Free Base, Form $C_0$

| No. | Pos. [2θ°]* | d-spacing [Å] | Rel. Int.[%] |
|---|---|---|---|
| 1 | 2.03 | 43.473 | 5 |
| 2 | 7.96 | 11.104 | 4 |
| 3 | 8.49 | 10.411 | 86 |
| 4 | 8.77 | 10.078 | 100 |
| 5 | 10.66 | 8.293 | 2 |
| 6 | 13.92 | 6.358 | 33 |
| 7 | 14.44 | 6.130 | 12 |
| 8 | 15.15 | 5.845 | 6 |
| 9 | 15.39 | 5.752 | 11 |
| 10 | 15.93 | 5.560 | 5 |
| 11 | 17.56 | 5.045 | 19 |
| 12 | 18.13 | 4.890 | 20 |
| 13 | 18.47 | 4.801 | 18 |
| 14 | 19.15 | 4.632 | 14 |
| 15 | 19.74 | 4.493 | 10 |
| 16 | 20.27 | 4.377 | 8 |
| 17 | 20.42 | 4.346 | 17 |
| 18 | 21.10 | 4.208 | 30 |
| 19 | 21.36 | 4.157 | 27 |
| 20 | 21.86 | 4.063 | 45 |
| 21 | 23.56 | 3.773 | 6 |
| 22 | 24.59 | 3.618 | 67 |
| 23 | 25.64 | 3.471 | 5 |
| 24 | 26.02 | 3.422 | 2 |

TABLE 17-continued

XRPD Peaks for Free Base, Form $C_0$

| No. | Pos. [2θ°]* | d-spacing [Å] | Rel. Int.[%] |
|---|---|---|---|
| 25 | 27.01 | 3.299 | 1 |
| 26 | 27.75 | 3.212 | 2 |
| 27 | 29.40 | 3.036 | 7 |
| 28 | 30.07 | 2.969 | 5 |
| 29 | 31.26 | 2.859 | 1 |
| 30 | 31.63 | 2.826 | 2 |
| 31 | 32.13 | 2.784 | 2 |
| 32 | 32.63 | 2.742 | 1 |
| 33 | 33.37 | 2.683 | 1 |
| 34 | 34.06 | 2.630 | 2 |
| 35 | 34.32 | 2.611 | 1 |

TABLE 17-continued

XRPD Peaks for Free Base, Form $C_0$

| No. | Pos. [2θ°]* | d-spacing [Å] | Rel. Int.[%] |
|---|---|---|---|
| 36 | 34.88 | 2.570 | 1 |
| 37 | 35.12 | 2.553 | 1 |
| 38 | 35.44 | 2.531 | 1 |
| 39 | 35.88 | 2.501 | 1 |
| 40 | 38.64 | 2.329 | 1 |

Thermal Analysis

Figure 28:
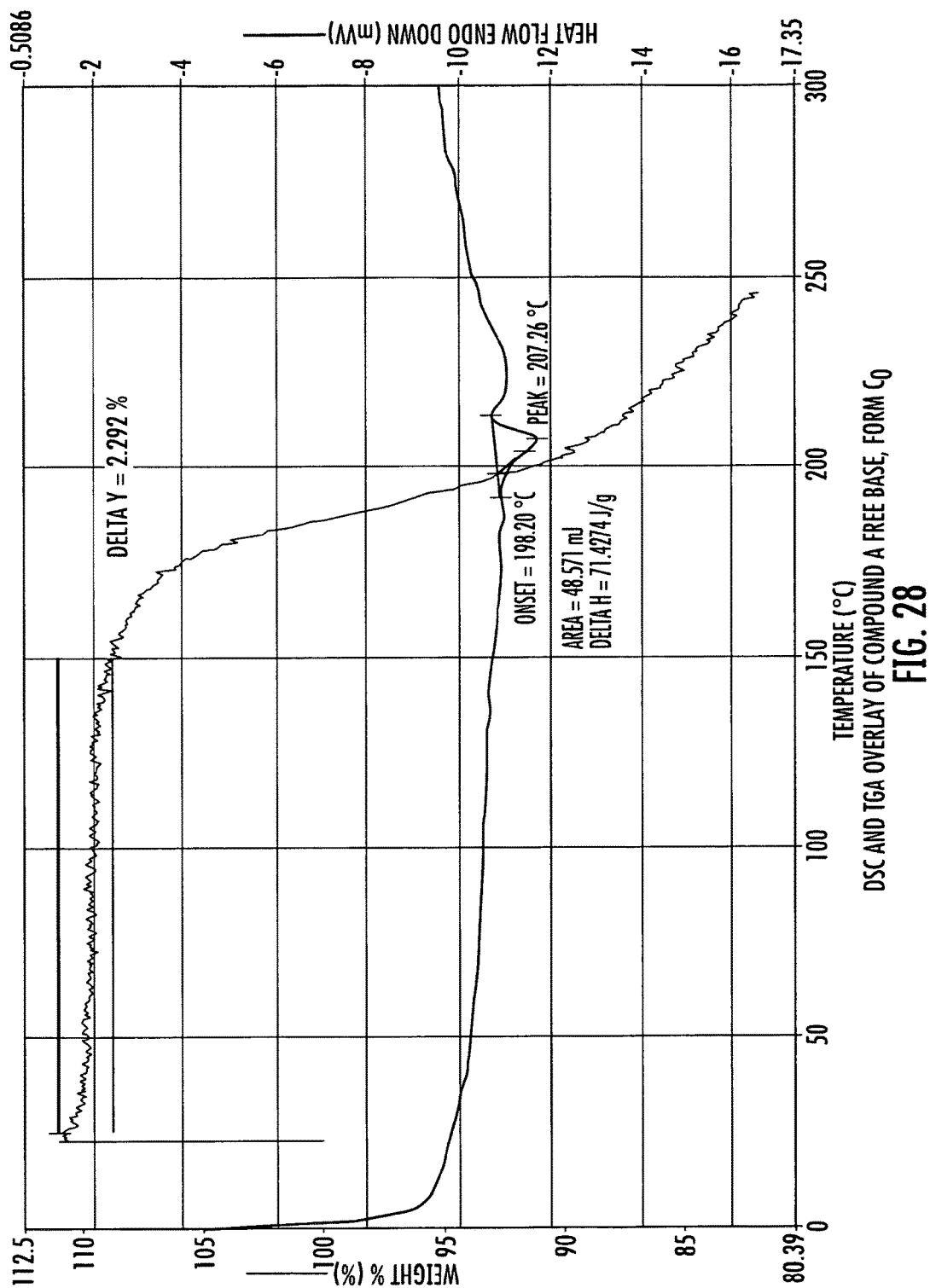
FIG. 28 shows a DSC and TGA Overlay of Compound A Free Base, Form $C_0$.

The DSC curve of the free base, Form $C_0$, shows the presence of one endothermic peak; at 207.3° C. having a $\Delta H_{Fus}$ of 71.4 J/g (FIG. 28). Form $C_0$ had a weight loss of 2.3% between 25 and 150° C.

Optical Microscopy

Figure 29:
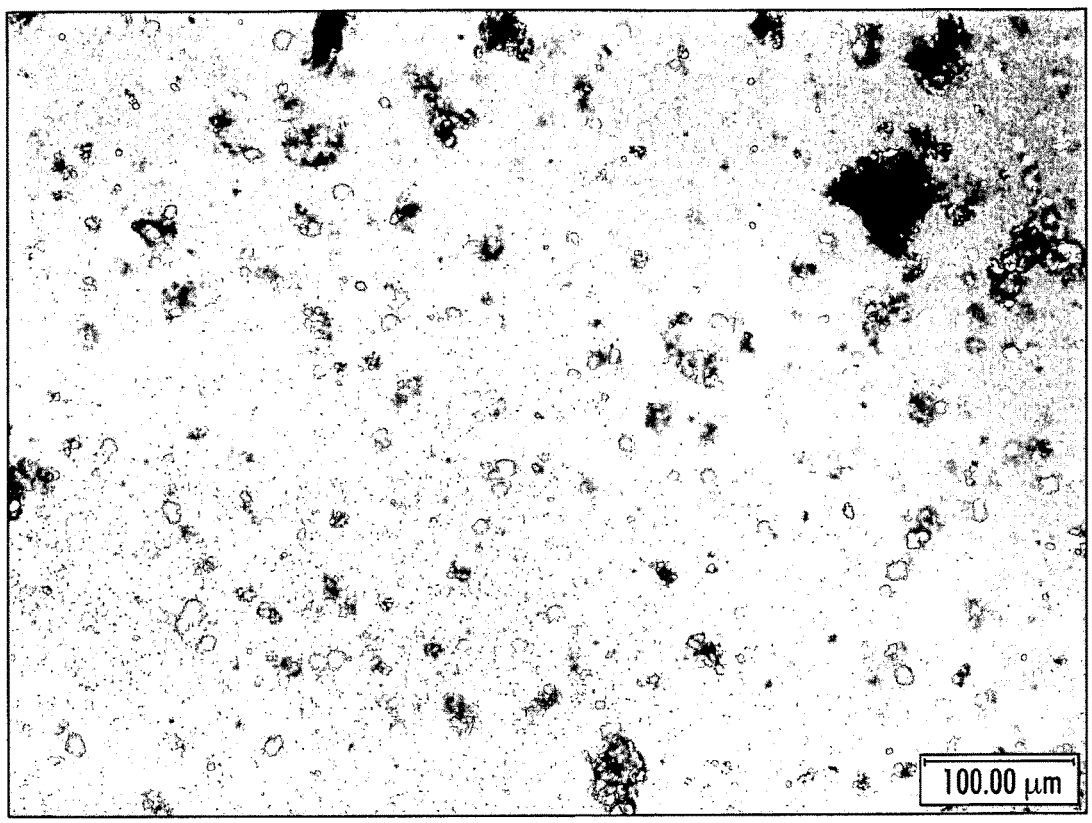
FIG. 29 shows a photomicrograph of Compound A A Free Base, Form $C_0$.

In FIG. 29, the sample presented agglomerates and individual irregular shaped crystals. The sample showed birefringence under plane polarized light.

Compound A, Hydrochloride Salt, Form A

Preparation

The salt was prepared according to Example 5.

XRPD

The X-ray diffraction data for the chloride salt, Form A, is given in FIG. 30 and Table 18.

TABLE 18

XRPD Peaks for the Hydrochloride Salt, Form A

| No. | Pos. [2θ°]* | d-spacing [Å] | Rel. Int.[%] |
|---|---|---|---|
| 1 | 6.13 | 14.403 | 2 |
| 2 | 7.45 | 11.863 | 100 |
| 3 | 7.95 | 11.108 | 3 |
| 4 | 8.55 | 10.337 | 25 |
| 5 | 10.51 | 8.409 | 1 |
| 6 | 12.20 | 7.248 | 42 |
| 7 | 12.94 | 6.837 | 4 |
| 8 | 13.55 | 6.532 | 0 |
| 9 | 14.94 | 5.926 | 2 |
| 10 | 15.90 | 5.569 | 1 |
| 11 | 16.21 | 5.463 | 2 |
| 12 | 17.12 | 5.175 | 16 |
| 13 | 17.95 | 4.937 | 2 |
| 14 | 18.34 | 4.833 | 1 |
| 15 | 18.83 | 4.710 | 37 |
| 16 | 18.87 | 4.700 | 29 |
| 17 | 19.26 | 4.606 | 4 |
| 18 | 20.24 | 4.383 | 1 |
| 19 | 21.27 | 4.174 | 1 |
| 20 | 22.30 | 3.983 | 12 |
| 21 | 23.58 | 3.770 | 0 |
| 22 | 24.49 | 3.631 | 9 |
| 23 | 24.88 | 3.576 | 3 |
| 24 | 25.57 | 3.481 | 8 |
| 25 | 26.08 | 3.414 | 8 |
| 26 | 27.14 | 3.283 | 0 |
| 27 | 27.75 | 3.213 | 3 |
| 28 | 28.34 | 3.147 | 3 |
| 29 | 30.81 | 2.900 | 3 |
| 30 | 31.06 | 2.877 | 3 |
| 31 | 31.80 | 2.812 | 2 |
| 32 | 33.46 | 2.676 | 4 |
| 33 | 34.13 | 2.625 | 4 |
| 34 | 34.89 | 2.570 | 2 |
| 35 | 36.22 | 2.478 | 1 |
| 36 | 37.44 | 2.400 | 1 |
| 37 | 39.42 | 2.284 | 1 |
| 38 | | | |

*The use of ZBG or glass plates typically introduces a positive sample height displacement and results in small (0.05° to 0.2°) offset in 2θ values. The highest peak (intensity 100%) is set in bold letters.

Thermal Analysis

Figure 31:
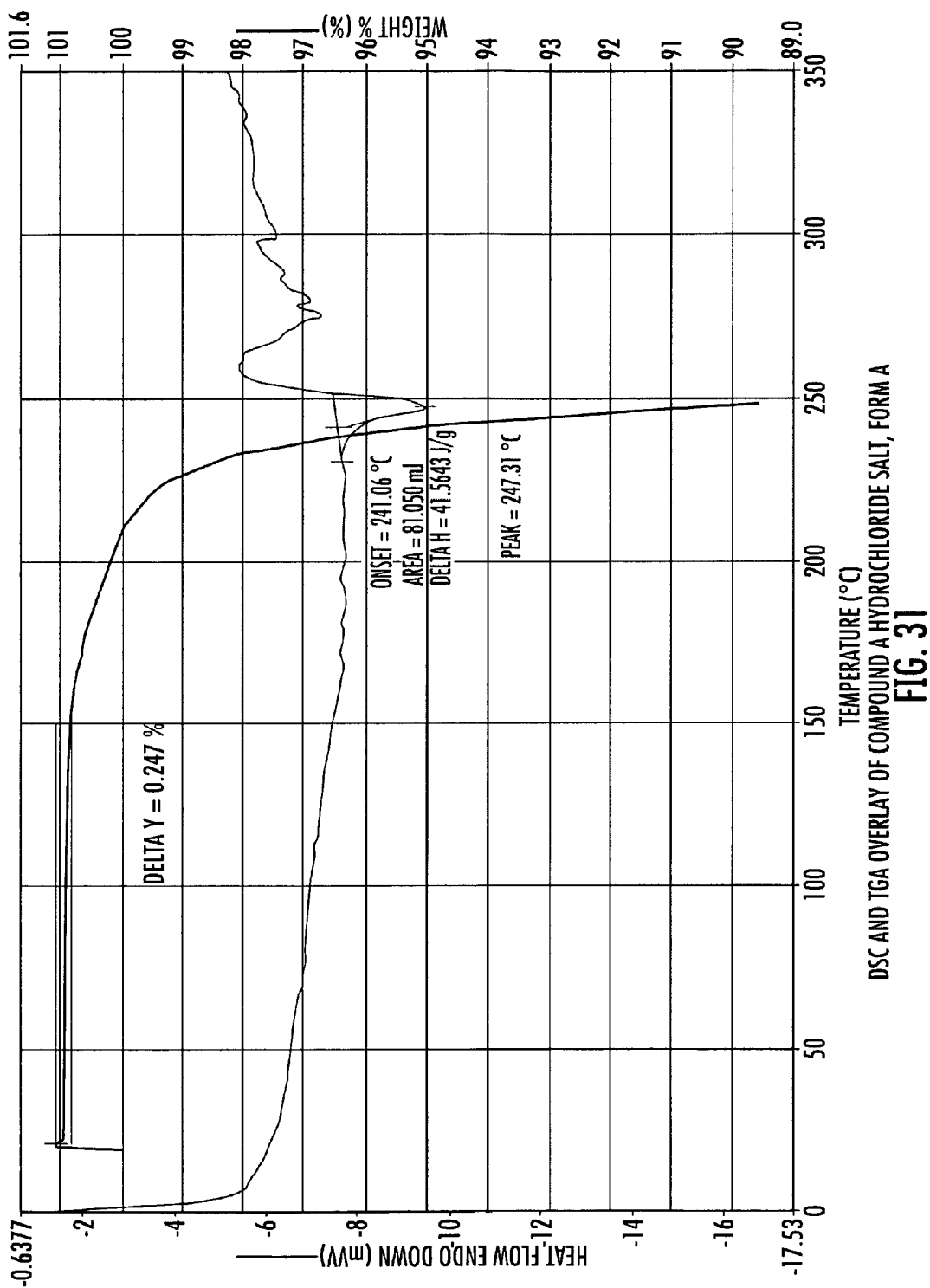
FIG. 31 shows a DSC and TGA Overlay of Compound A Hydrochloride Salt, Form A.

The DSC curve of the hydrochloride salt, Form A, shows one endothermic peak at 247.3° C. having a $\Delta H_{Fus}$ of 41.6 J/g (FIG. 31). The hydrochloride salt, Form A, had a weight loss of 0.2% between 25 and 150° C.

Water Sorption

Figure 32:
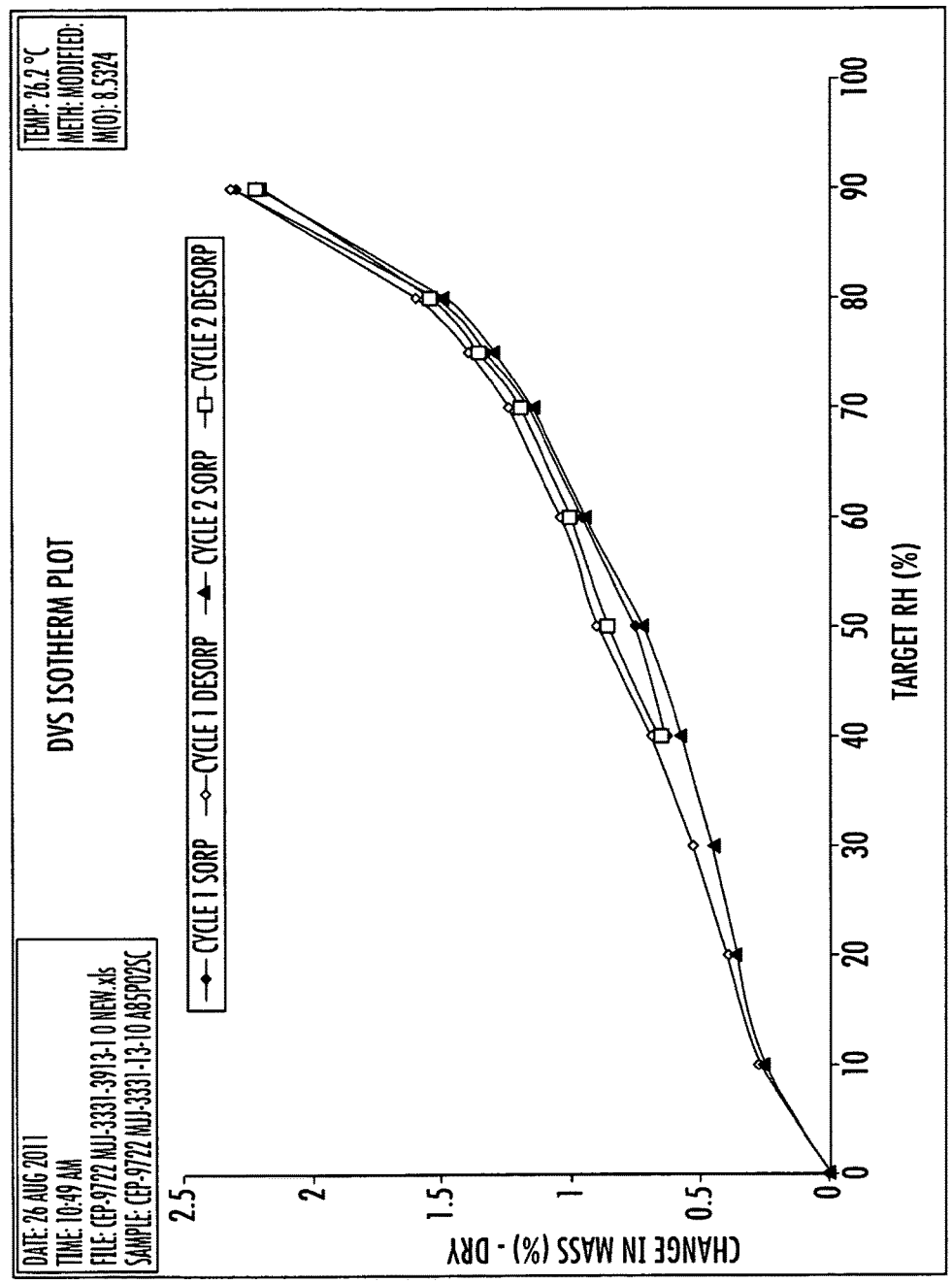
FIG. 32 shows a DVS of Compound A Hydrochloride Salt, Form A.

The DVS Plot (FIG. 32) indicated there is surface adsorption with limited bulk absorption throughout the entire RH range. The total uptake in moisture is ~2.25%.

Stability

The data in Table 19 show a relatively constant XRPD pattern and DSC value with modest changes in TGA value. The HPLC values are quite different with Assay value decreasing to nearly half after 28 days of testing. Also noted was a steady decline in HPLC purity and an increase in Compound B content to 1.5%. The theoretical value for Compound A content in a Compound A monohydrochloride salt is 92.0%.

TABLE 19

Stability at 40° C. and 75% RH of the Hydrochloride Form A

| Day | XRPD | DSC ° C. | TGA % | COMPOUND A Assay | COMPOUND B Assay | HPLC Purity |
|---|---|---|---|---|---|---|
| 0 | A | 244.8 | 0.1 | 39.9 | 0.3 | 99.1 |
| 7 | No change | 247.6 | 1.5 | 22.3 | 0.7 | 96.3 |
| 14 | No change | 245.9 | 1.1 | 21.6 | 1.1 | 94.0 |
| 28 | No change | 245.5 | 0.9 | 19.6 | 1.5 | 91.1 |

Compound A, Fumarate Salt, Form A

Preparation

The salt was prepared according to Example 5.

XRPD

The X-ray diffraction data for Compound A Fumarate Salt, Form A, is given in FIG. 33 and Table 20.

TABLE 20

XRPD Peaks for the Fumarate Salt, Form A

| No. | Pos. [2θ°]* | d-spacing [Å] | Rel. Int.[%] |
|---|---|---|---|
| 1 | 8.98 | 9.842 | 100 |
| 2 | 10.54 | 8.388 | 26 |
| 3 | 11.06 | 7.994 | 11 |
| 4 | 12.94 | 6.835 | 4 |
| 5 | 14.86 | 5.958 | 20 |
| 6 | 15.44 | 5.734 | 2 |
| 7 | 15.55 | 5.694 | 5 |
| 8 | 16.19 | 5.469 | 5 |
| 9 | 17.07 | 5.190 | 37 |
| 10 | 17.69 | 5.008 | 20 |
| 11 | 18.20 | 4.871 | 3 |
| 12 | 18.74 | 4.732 | 4 |
| 13 | 19.04 | 4.657 | 3 |
| 14 | 19.13 | 4.637 | 7 |
| 15 | 19.34 | 4.585 | 24 |
| 16 | 19.68 | 4.508 | 5 |
| 17 | 20.72 | 4.284 | 4 |
| 18 | 21.09 | 4.209 | 24 |
| 19 | 21.80 | 4.074 | 2 |
| 20 | 22.32 | 3.980 | 8 |
| 21 | 22.88 | 3.884 | 8 |
| 22 | 23.50 | 3.783 | 16 |
| 23 | 24.04 | 3.699 | 22 |
| 24 | 24.19 | 3.677 | 15 |
| 25 | 25.36 | 3.509 | 4 |
| 26 | 25.45 | 3.497 | 2 |
| 27 | 25.59 | 3.479 | 2 |
| 28 | 25.71 | 3.463 | 8 |
| 29 | 25.90 | 3.437 | 8 |
| 30 | 26.08 | 3.415 | 4 |
| 31 | 26.24 | 3.393 | 4 |

TABLE 20-continued

XRPD Peaks for the Fumarate Salt, Form A

| No. | Pos. [2θ]* | d-spacing [Å] | Rel. Int.[%] |
|---|---|---|---|
| 32 | 26.51 | 3.360 | 2 |
| 33 | 26.75 | 3.329 | 4 |
| 34 | 27.29 | 3.266 | 7 |
| 35 | 28.95 | 3.082 | 11 |
| 36 | 29.92 | 2.984 | 4 |
| 37 | 30.78 | 2.902 | 3 |
| 38 | 30.99 | 2.884 | 3 |
| 39 | 31.09 | 2.874 | 6 |
| 40 | 36.83 | 2.438 | 2 |

*The use of ZBG or glass plates typically introduces a positive sample height displacement and results in small (0.05° to 0.2°) offset in 2θ values. The highest peak (intensity 100%) is set in bold letters.

Thermal Analysis

Figure 34:
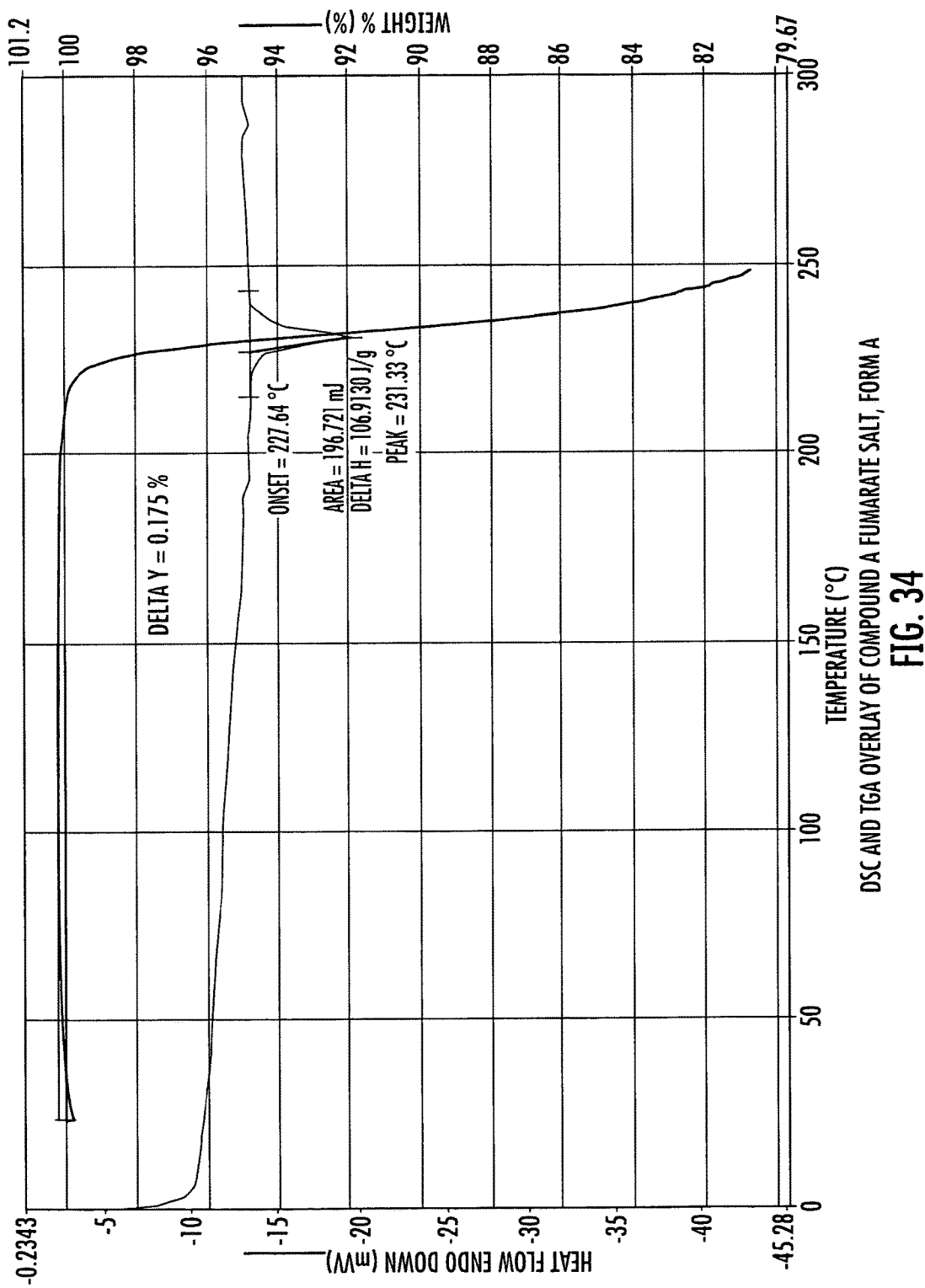
FIG. 34 shows a DSC and TGA Overlay of Compound A Fumarate Salt, Form A.

The DSC curve of the fumarate salt, Form A, showed the presence of one endothermic peak; at 231.3° C. having a $\Delta H_{Fus}$ of 106.9 J/g (FIG. 34). Form A had a weight loss of 0.2% between 25 and 150° C.

Compound A, p-Toluenesulfonate Salt, Form A

Preparation

The salt was prepared according to Example 5.

XRPD

Characterization of the p-Toluenesulfonate Salt, Form A is depicted in FIG. 35 and Table 21.

TABLE 21

XRPD Peaks for the p-Toluenesulfonate Salt, Form A

| No. | Pos. [2θ]* | d-spacing [Å] | Rel. Int.[%] |
|---|---|---|---|
| 1 | 6.02 | 14.669 | 74 |
| 2 | 9.56 | 9.242 | 43 |
| 3 | 10.31 | 8.573 | 61 |
| 4 | 10.54 | 8.391 | 25 |
| 5 | 11.03 | 8.017 | 96 |
| 6 | 12.01 | 7.364 | 100 |
| 7 | 12.89 | 6.864 | 21 |
| 8 | 13.22 | 6.693 | 33 |
| 9 | 14.32 | 6.180 | 12 |
| 10 | 15.00 | 5.900 | 24 |
| 11 | 16.71 | 5.301 | 36 |
| 12 | 17.02 | 5.206 | 22 |
| 13 | 17.51 | 5.061 | 59 |
| 14 | 17.79 | 4.983 | 68 |
| 15 | 18.02 | 4.919 | 78 |
| 16 | 18.68 | 4.747 | 19 |
| 17 | 18.98 | 4.672 | 29 |
| 18 | 19.37 | 4.578 | 7 |
| 19 | 20.22 | 4.388 | 7 |
| 20 | 20.76 | 4.276 | 35 |
| 21 | 20.98 | 4.231 | 34 |
| 22 | 21.14 | 4.199 | 29 |
| 23 | 21.36 | 4.156 | 9 |
| 24 | 21.67 | 4.097 | 10 |
| 25 | 21.96 | 4.045 | 33 |
| 26 | 22.11 | 4.017 | 23 |
| 27 | 22.70 | 3.914 | 21 |
| 28 | 23.13 | 3.842 | 23 |
| 29 | 23.39 | 3.800 | 84 |
| 30 | 23.51 | 3.781 | 56 |
| 31 | 24.11 | 3.689 | 14 |
| 32 | 24.53 | 3.626 | 8 |
| 33 | 24.84 | 3.582 | 54 |
| 34 | 25.08 | 3.547 | 9 |
| 35 | 26.56 | 3.353 | 33 |
| 36 | 27.57 | 3.232 | 8 |
| 37 | 28.15 | 3.168 | 13 |
| 38 | 28.78 | 3.099 | 9 |
| 39 | 30.22 | 2.955 | 11 |
| 40 | 30.43 | 2.935 | 9 |

*The use of ZBG or glass plates typically introduces a positive sample height displacement and results in small (0.05° to 0.2°) offset in 2θ values. The highest peak (intensity 100%) is set in bold letters.

Thermal Analysis

Figure 36:
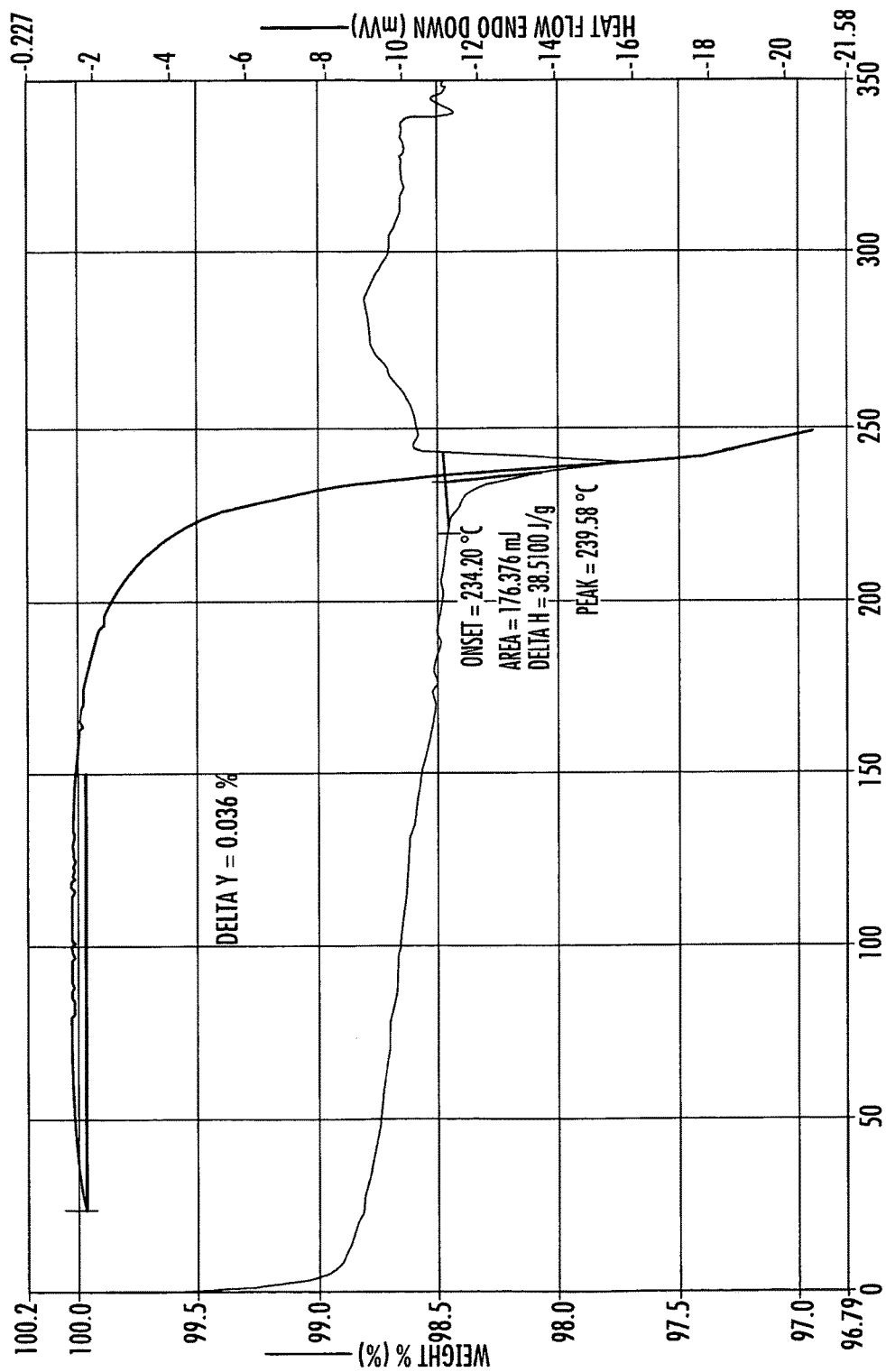
FIG. 36 shows a DSC and TGA Overlay of Compound A p-Toluenesulfonate Salt, Form A.
Figure 37:
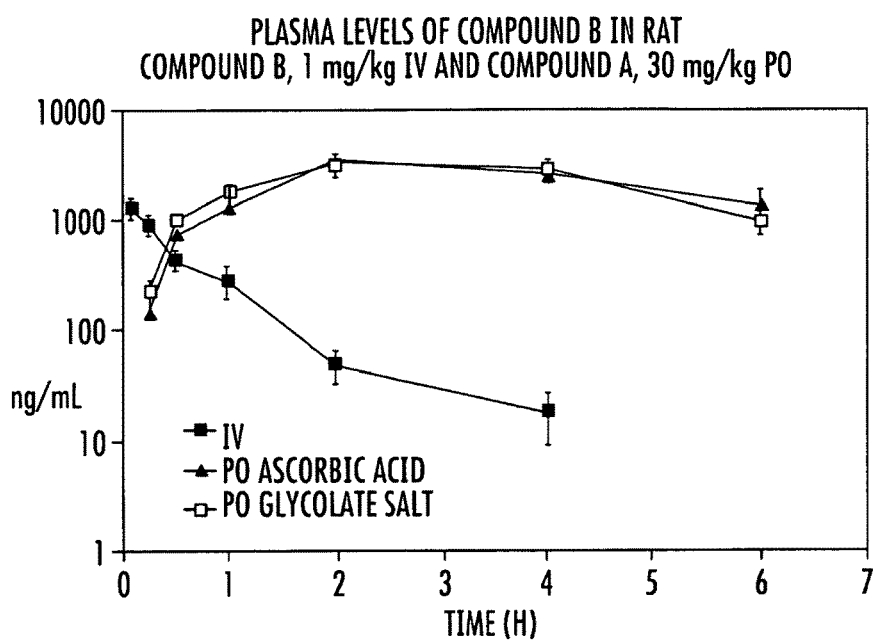
FIG. 37 shows plasma levels of Compound B, 1 mg/kg intravenous, Compound A, ascorbic acid salt, 30 mg/kg oral, and Compound A, glycolate hydrate salt, 30 mg/kg oral in rat.

The DSC curve of the p-toluenesulfonate salt, Form A, shows the presence of one endothermic peak; at 239.6° C. having a $\Delta H_{Fus}$ of 38.5 J/g (FIG. 36). Form A had a weight loss of 0.04% between 25 and 150° C.

What is claimed:

1. A crystalline form of 4,5,6,7-tetrahydro-11-methoxy-2-[(4-methyl-1-piperazinyl)methyl]-1H-cyclopenta[a]pyrrolo[3,4-c]carbazole-1,3(2H)-dione (Compound A)

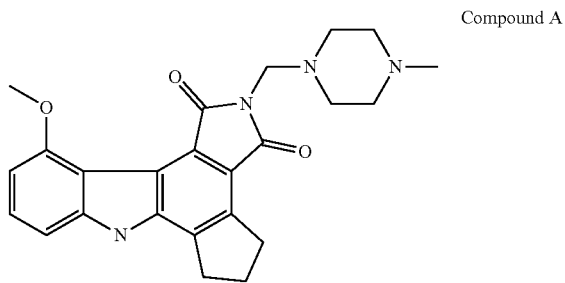 [SMILES: COc1cccc2[nH]c3c4c(c5c(c3c12)C(=O)N(CN1CCN(C)CC1)C5=O)CCC4]

Compound A that is
Compound A, glycolate salt hydrate Form $A_1$;
Compound A, L-malate salt Form $A_1$; or
Compound A, L-pyroglutamate salt Form $A_1$.

2. The crystalline form of claim 1 that is Compound A, glycolate salt hydrate Form $A_1$.

3. The crystalline form of claim 2, characterized by an X-ray powder diffraction pattern having at least three peaks selected from the group consisting of 8.2, 8.7, 13.8, 14.9, 16.4, 17.5, 18.2, 18.5, 20.2, 20.6, 21.2, 21.4, 23.0, 24.6, 27.8, 29.9, 30.1, and 30.5 degrees two theta±0.2 degrees 2-theta.

4. The crystalline form of claim 2, further characterized by an X-ray powder diffraction pattern substantially as depicted in FIG. 9 or FIG. 10.

5. The crystalline form of claim 2, further characterized by a DSC substantially as depicted in FIG. 11.

6. The crystalline form of claim 2, further characterized by a DVS substantially as depicted in FIG. 12.

7. The crystalline form of claim 1 that is Compound A, L-malate salt Form $A_1$.

8. The crystalline form of claim 7, characterized by an X-ray powder diffraction pattern having at least three peaks selected from the group consisting of 8.6, 9.2, 10.1, 10.4, 11.7, 11.9, 14.7, 15.3, 15.6, 17.2, 17.8, 18.5, 20.3, 20.7, 21.2, 22.4, 23.5, 24.3, and 27.0±0.2 degrees 2-theta.

9. The crystalline form of claim 7, further characterized by an X-ray powder diffraction pattern substantially as depicted in FIG. 14 or FIG. 15.

10. The crystalline form of claim 5, further characterized by a DSC substantially as depicted in FIG. 16.

Figure 17:
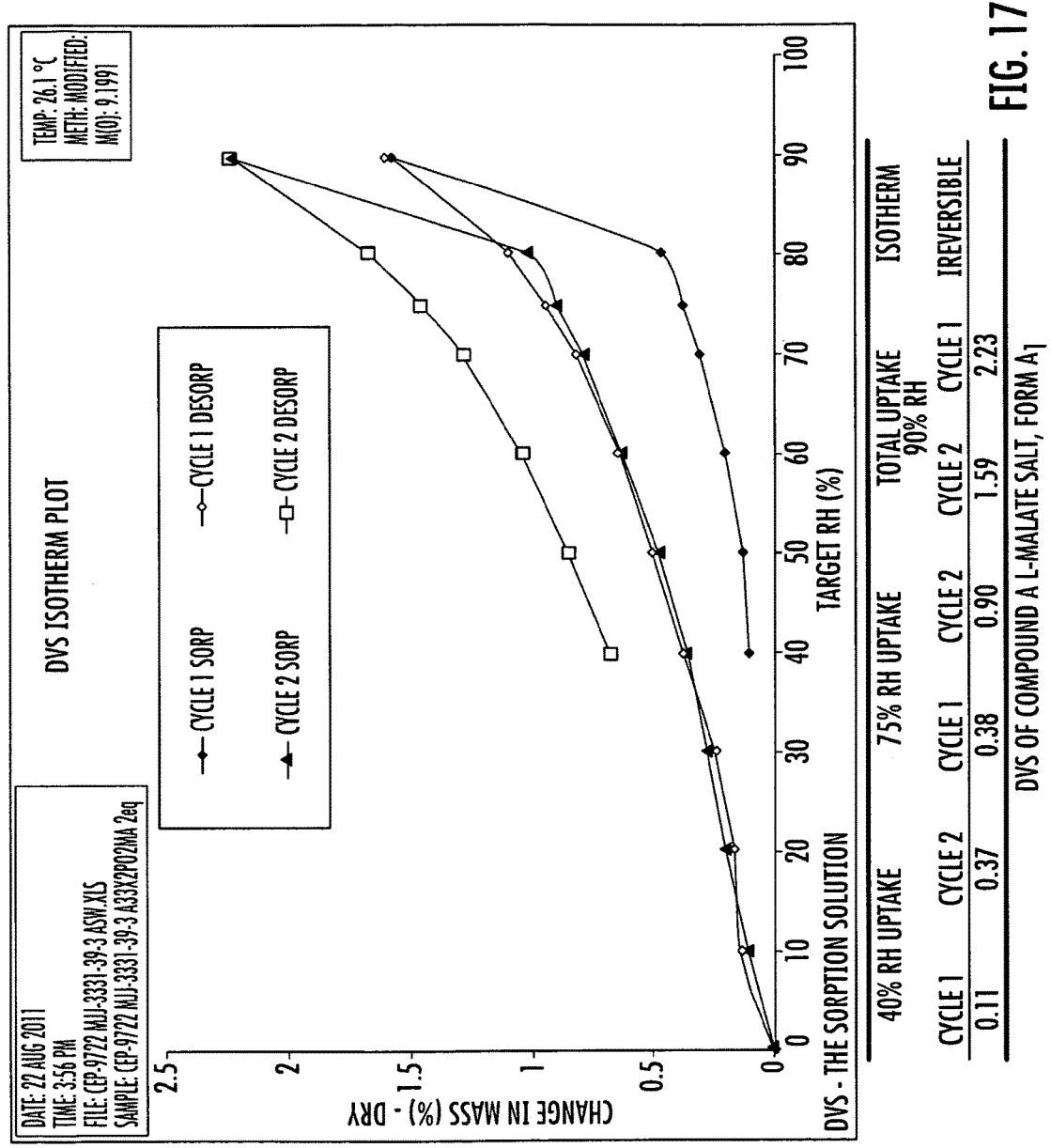
FIG. 17 shows a DVS of Compound A L-Malate Salt, Form $A_1$.

11. The crystalline form of claim 7, further characterized by a DVS substantially as depicted in FIG. 17.

12. The crystalline form of claim 1 that is Compound A, L-pyroglutamate salt Form $A_1$.

13. The crystalline form of claim 12, characterized by an X-ray powder diffraction pattern having at least three peaks selected from the group consisting of 6.0, 9.6, 10.3, 10.5, 11.0, 12.0, 13.2, 15.0, 16.7, 17.5, 17.8, 18.0, 19.0, 20.8, 21.0, 21.1, 22.0, 22.1, 23.1, 23.4, 23.5, 24.8, and 26.6±0.2 degrees 2-theta.

14. The crystalline form of claim 12, further characterized by an X-ray powder diffraction pattern substantially as depicted in FIG. 21 or FIG. 22.

15. The crystalline form of claim 12, further characterized by a DSC substantially as depicted in FIG. 23.

Figure 24:
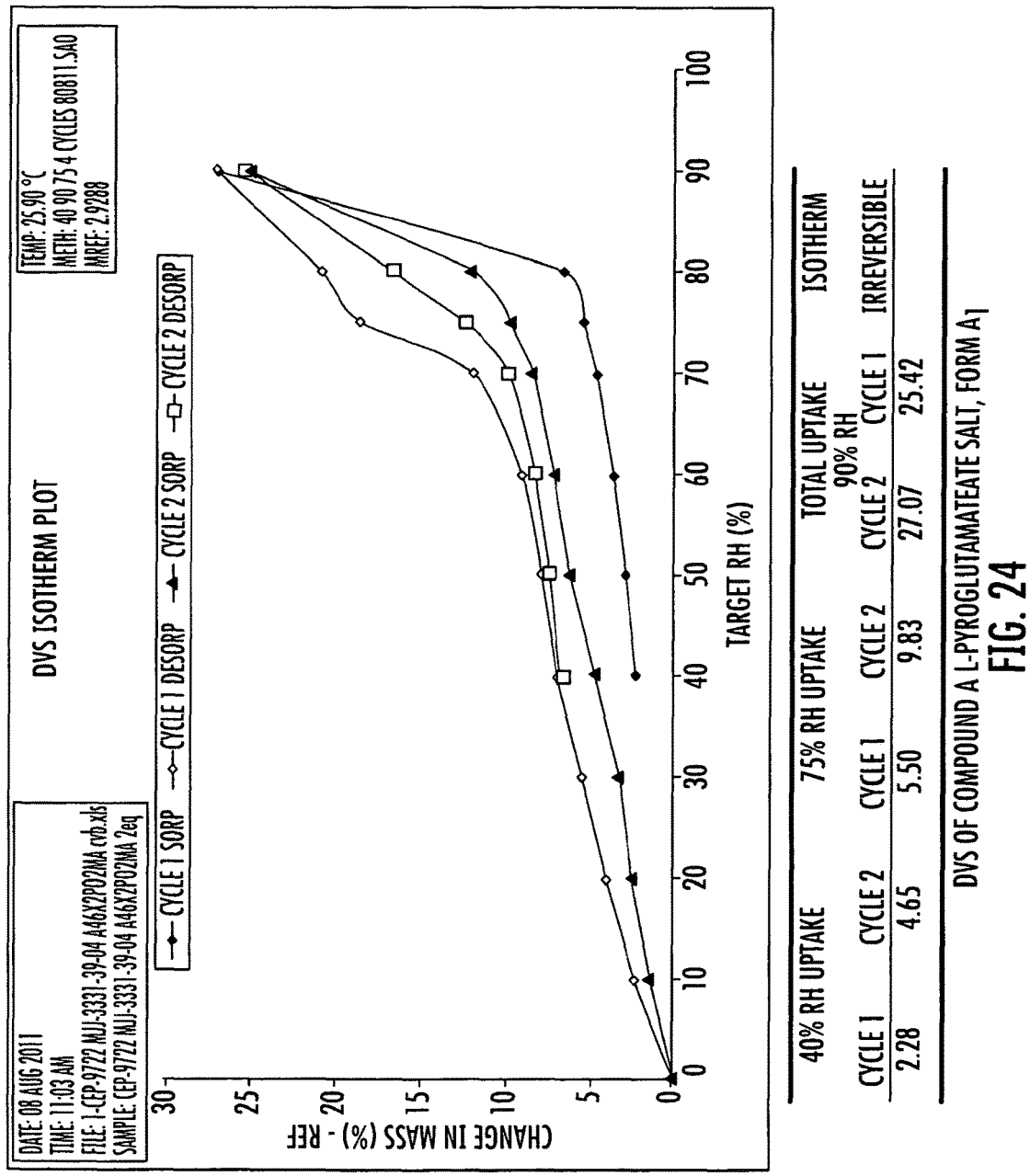
FIG. 24 shows a DVS of Compound A L-Pyroglutamate Salt, Form $A_1$.

16. The crystalline form of claim 12, further characterized by a DVS substantially as depicted in FIG. 24.

17. A pharmaceutical composition comprising the crystalline form of claim 1, and at least one pharmaceutically acceptable excipient.

18. A method of treating cancer in a patient comprising administering to the patient a crystalline form of 4,5,6,7-tetrahydro-11-methoxy-2-[(4-methyl-1-pyrrolo[3,4-c]carbazole-1,3(2H)-dione (Compound A) according to claim 1, wherein the cancer is breast cancer or ovarian cancer.

* * * * *